(12) United States Patent
Aikins et al.

(10) Patent No.: US 6,639,107 B1
(45) Date of Patent: Oct. 28, 2003

(54) CYCLOPENTYL SULFONAMIDE DERIVATIVES

(75) Inventors: James Abraham Aikins, Pendleton, IN (US); Edward C R Smith, Fishers, IN (US); Timothy Alan Shepherd, Indianapolis, IN (US); Dennis Michael Zimmerman, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/130,156

(22) PCT Filed: Nov. 3, 2000

(86) PCT No.: PCT/US00/28878

§ 371 (c)(1),
(2), (4) Date: May 14, 2002

(87) PCT Pub. No.: WO01/42203

PCT Pub. Date: Jun. 14, 2001

Related U.S. Application Data

(60) Provisional application No. 60/169,684, filed on Dec. 8, 1999.

(51) Int. Cl.⁷ .............................................. C07C 303/00
(52) U.S. Cl. .......................................... 564/84; 564/79
(58) Field of Search ...................... 564/84, 79; 514/393

(56) References Cited

U.S. PATENT DOCUMENTS

| | | | |
|---|---|---|---|
| 4,350,685 A | * | 9/1982 | Ali et al. ...................... 424/45 |
| 5,958,960 A | | 9/1999 | Massey et al. ............... 514/393 |

FOREIGN PATENT DOCUMENTS

| | | |
|---|---|---|
| EP | 0 937 708 | 2/1998 |
| WO | WO 98/33496 | 2/1997 |
| WO | WO 99/43285 | 2/1998 |
| WO | WO 00/06148 | 7/1998 |
| WO | WO 00/06156 | 7/1998 |
| WO | WO 00/06158 | 7/1998 |
| WO | WO 00/06159 | 7/1998 |
| WO | WO 00/66546 | 4/1999 |
| WO | WO 01/96289 | 6/2000 |
| WO | WO 02/32858 | 10/2000 |

OTHER PUBLICATIONS

U.S. patent application Ser. No. 60/294,428, Cantrell et al., filed May 30, 2001.

U.S. patent application Ser. No. 60/296,008, Davison et al., filed Jun. 5, 2001.

* cited by examiner

*Primary Examiner*—Alan L. Rotman
*Assistant Examiner*—Héctor M Reyes
(74) *Attorney, Agent, or Firm*—Nelsen L. Lentz

(57) ABSTRACT

The present invention provides certain cyclopentyl sulfonamide derivatives of formula (I): useful for potentiating glutamate receptor function in a mammal. It also relates to novel cyclopentyl sulfonamide derivatives, to processes for their preparation and to pharmaceutical compositions containing them.

29 Claims, No Drawings

CYCLOPENTYL SULFONAMIDE DERIVATIVES

This is a 371 of PCT/US00/28878 filed Nov. 3, 2000 which claims priority to U.S. Provisional Application No. 60/169,684 filed Dec. 8, 1999.

The present invention relates to the potentiation of glutamate receptor function using certain cyclopentyl sulfonamide derivatives. It also relates to cyclopentyl sulfonamide novel derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are not fully understood.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, Neurobiology, and Arai et al., *The Journal of Pharmacology and Experimental Therapeutics*, 278: 627–638, 1996.

In addition, certain sulfonamide derivatives which potentiate glutamate receptor function in a mammal have been disclosed in International Patent Application Publication WO 98/33496 published Aug. 6, 1998 and International Patent Application Publication WO 99/43285 published Sep. 2, 1999.

It has now been found that cyclopentyl derivatives of the present invention are surprisingly potent potentiators of glutamate receptor function.

The present invention provides compounds of formula I:

formula I

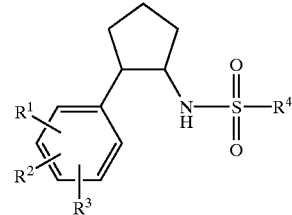

wherein
$R^1$, $R^2$, and $R^3$ each independently represent hydrogen, halogen, $CF_3$, $OCF_3$, CN, $NO_2$, $NH_2$, (1–6C)alkyl, (1–6C)alkoxy, —$(CH_2)_n NHSO_2 R^5$, —$(CH_2)_n NNHC(=O)R^5$, —$SO_2R^5$, —$C(=O)R^6$, —CH=$CHCO_2R^7$, heterocycle, or phenyl which is unsubstituted or substituted by one, two, or three substituents selected from the group consisting of halogen, $CF_3$, $OCF_3$, CN, $NO_2$, $NH_2$, (1–6C)alkyl, (1–6C)alkoxy, —$(CH_2)_n NHSO_2 R^5$, —$(CH_2)_n NHC(=O)R^5$, —$SO_2R^5$, —$C(=O)R^6$, —$C(=O)NR^{10}R^{11}$, —$SO_2NR^{10}R^{11}$, or —CH=$CHCO_2R^7$;

$R^4$ represents (1–6C)alkyl, (2–6C)alkenyl, or $NR^8R^9$;

$R^5$ represents (1–6C)alkyl, $CF_3$, or phenyl which is unsubstituted or substituted by one, two, or three substituents selected from the group consisting of halogen, $CF_3$, CN, $NO_2$, $NH_2$, (1–6C)alkyl, or (1–6C)alkoxy;

$R^6$ represents (1–4C)alkyl or phenyl;

$R^7$ represents hydrogen or (1–4C)alkyl;

$R^8$ and $R^9$ each independently represent hydrogen or (1–4C)alkyl;

$R^{10}$ and $R^{11}$ each independently represent hydrogen or (1–4C)alkyl; and n is 0, 1, 2, 3, or 4;

or a pharmaceutically acceptable salt thereof.

The present invention further provides a method of potentiating glutamate receptor function in a patient requiring such treatment, which comprises administering to said patient an effective amount of a compound of formula I.

In addition, the present invention provides the use of a compound of formula I or a pharmaceutically acceptable salt thereof for potentiating glutamate receptor function.

The invention further provides pharmaceutical compositions comprising, a compound of formula I and a pharmaceutically acceptable diluent or carrier.

According to another aspect, the present invention provides the use of a compound of formula I, or a pharmaceutically acceptable salt thereof for the manufacture of a medicament for potentiating glutamate receptor function.

The present invention provides a method of treating cognitive disorders in a patient, which comprises administering to said patient an effective amount of a compound of formula I.

In addition, the present invention further provides a method of treating cognitive deficits associated with psychosis in a patient, which comprises administering to said patient an effective amount of a compound of formula I.

This invention also encompasses novel intermediates, and processes for the synthesis of the compounds of formula I.

In this specification, the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by compounds of formula I and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, and Parkinson's disease; reversal of drug-induced states (such as cocaine, amphetamines, alcohol-induced states); depression; attention deficit disorder; attention deficit hyperactivity disorder; psychosis; cognitive deficits associated with psychosis, drug-induced psychosis, stroke, and sexual dysfunction. Compounds of formula I may also be useful for improving memory (both short term and long term) and learning ability. The present invention provides the use of compounds of formula I for the treatment of each of these conditions.

It is understood that the trans and cis compounds of formulas I' and I" as represented below are included within the scope of the present invention, including the individual enantiomers thereof:

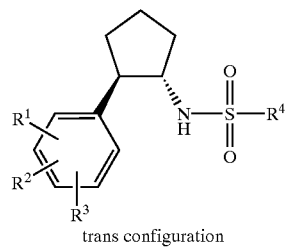

formula I' trans configuration

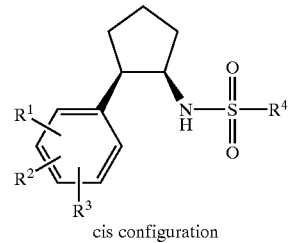

formula I"

cis configuration

As used herein the term "heterocycle" refers to a stable 5- to 7-membered monocyclic or 7- to 10-membered bicyclic heterocyclic ring which is saturated or unsaturated, and consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

Examples of such heterocycles include piperidinyl, piperazinyl, azepinyl, pyrrolyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinyl-sulfone, oxadiazolyl, triazolyl, tetrahydroquinolinyl, tetrahydrisoquinolinyl, and the like.

As used herein, the terms "halogen", "halo", "halide" or "Hal" refers to a chlorine, bromine, iodine or fluorine atom, unless otherwise specified.

As used herein the term "(1–6C)alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "(1–6C)alkyl" includes within its definition the term "(1–4C)alkyl".

As used herein the term "(2–6C)alkenyl" refers to a straight or branched, monovalent, unsaturated aliphatic chain having from two to six carbon atoms. Typical (2–6C) alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like. The term "(2–6C) alkenyl" includes within its definition the term "(2–4C) alkenyl".

As used herein the term "(1–6C)alkoxy" refers to a straight or branched alkyl chain having from one to six carbon atoms attached to an oxygen atom. Typical (1–6C) alkoxy groups include methoxy, ethoxy, propoxy, isopropoxy, butoxy, t-butoxy, pentoxy and the like. The term "(1–6C)alkoxy" includes within its definition the term "(1–4C)alkoxy".

As used herein, the term "Me" refers to a methyl group, the term "Et" refers to an ethyl group, the term "Pr" refers to a propyl group, the term "iPr" refers to an isopropyl group and the term "Ph" refers to a phenyl group.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt. The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, a-hydroxybutyrate, glycolate, tartrate, benzenesulfonate, methanesulfonate, ethanesulfonate, propanesulfonate, hydroxyethanesulfonate, naphthalene-1-sulfonate, napththalene-2-sulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred.

Enantiomeric enrichment is readily determined by one of ordinary skill in the art using standard techniques and procedures, such as gas or high performance liquid chromatography with a chiral column. In addition, separation and isolation of the compounds of the present invention into the individual enantiomers is similarly performed by one of ordinary skill in the art using standard techniques and procedures, such as gas or high performance liquid chromatography with a chiral column, or other standard resolving techniques. Choice of the appropriate chiral column, eluent and conditions necessary to effect separation of the enantiomeric pair is well within the knowledge of one of ordinary skill in the art. In addition, the enantiomers of compounds of the present invention can be resolved using standard techniques such as those described by J. Jacques, et al., *"Enantiomers, Racemates, and Resolutions"*, John Wiley and Sons, Inc., 1981, and E. L. Eliel and S. H. Wilen," *Stereochemistry of Organic Compounds"*, (Wiley-Interscience 1994), and European Patent Application No. EP-A-838448, published Apr. 29, 1998.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The designation "◀" refers to a bond that protrudes forward out of the plane of the page.

The designation "⊪⊩" refers to a bond that protrudes backward out of the plane of the page.

The designation "∿" refers to a bond wherein the stereochemistry is not defined.

The compounds of structures (4) and (6) can be prepared following the procedures set forth in Scheme I below. The reagents and starting materials are readily available to one of ordinary skill in the art. All substituents, unless otherwise specified are as previously defined.

Scheme I

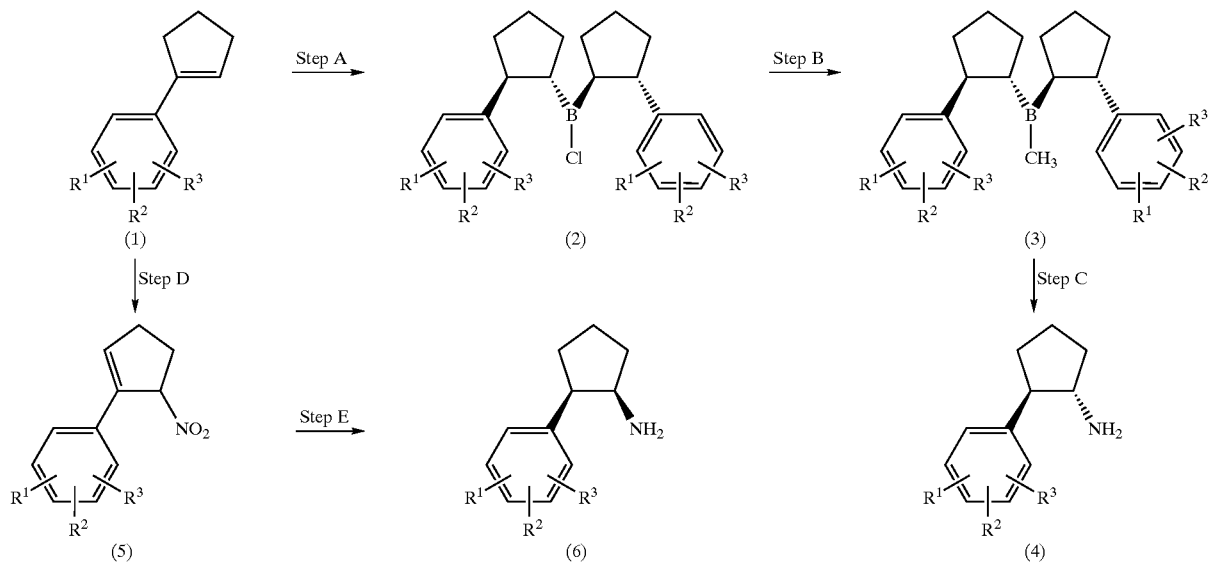

In Scheme I, step A, the cyclopentene of structure (1) is converted to the borane of structure (2) under standard conditions. For example, cyclopentene (1) is dissolved in a suitable organic solvent, such as dry methylene chloride under an atmosphere of nitrogen and cooled to about 0° C. The solution is treated with about 0.5 equivalents of monochloroborane-methyl sulfide. The reaction mixture is allowed to warm to room temperature and stirred for about 8 to 16 hours. The solvent is removed under vacuum under a nitrogen atmosphere to provide borane (2).

In Scheme I, step B, borane (2) is methylated to provide the methylborane of structure (3). For example borane (2) is dissolved in a suitable organic solvent, such as dry hexanes under an atmosphere of nitrogen. The solution is cooled to about 0° C. and treated with about 0.3 equivalents of trimethylaluminum in hexanes. The reaction mixture is allowed to warm to room temperature and stirred for about 1.5 hours. A precipitate results and the supernatant is transferred via cannula to a nitrogen flushed separatory funnel containing saturated aqueous ammonium chloride. The organic phase is then transferred via cannula to a flask containing anhydrous sodium sulfate. The organic solution is then transferred via cannula to a dry, nitrogen flushed flask and the solvent is removed under vacuum in the presence of a nitrogen atmosphere to provide the methylated borane (3).

In Scheme I, step C, the methylated borane (3) is hydrolyzed to the trans-cyclopentylamine of structure (4). For example, methylated borane (3) is dissolved in a suitable organic solvent, such as dry tetrahydrofuran and cautiously treated in small portions with a slight excess of hydroxylamine-O-sulfonic acid (referred to herein as "HAS") dissolved in tetrahydrofuran. The reaction is exothermic. After addition is complete, the reaction mixture is stirred for about 24 hours and then filtered. The filtrate is concentrated under vacuum and the residue is treated with concentrated HCl:methanol:water:diethyl ether (30:15:20:60, by volume). The mixture is stirred at room temperature for about 30 minutes. The layers are separated, the organic phase is washed with water and the water wash is combined with the aqueous phase. The aqueous phase is cooled to about 0° C., diethyl ether is added and the aqueous is made basic with sodium hydroxide. The organic phase is separated and the aqueous phase is extracted with diethyl ether and ethyl acetate. The organic phase and organic extracts are combined, dried over anhydrous sodium sulfate, filtered and concentrated under vacuum to provide the cyclopentylamine (4).

In Scheme I, step D, the cyclopentene of structure (1) is nitrated under standard conditions to provide the compound of structure (5). For example, see the procedure disclosed by F. G. Bordwell, et al., *J. Org. Chem.*, 1765.

In Scheme I, step E, the nitrated compound of structure (5) is reduced under standard conditions to provide the amine of structure (6). For example, compound (5) is dissolved in a suitable organic solvent, such as ethanol, treated with a suitable hydrogenation catalyst, such as palladium on carbon, the solution is placed under hydrogen at about 413.69 kPa (60 psi). After about 8 to 16 hours, the reaction mixture is filtered and the filtrate is concentrated under vacuum to provide the compound (6).

The compound of structure (6) can be prepared by the alternative procedures set forth in Schemes IA and IB below. The reagents and starting materials are readily available to one of ordinary skill in the art. All substituents, unless otherwise specified are as previously defined.

Scheme IA

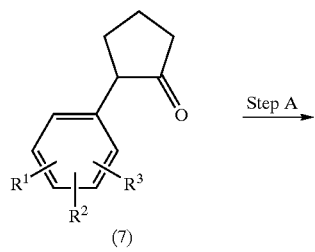

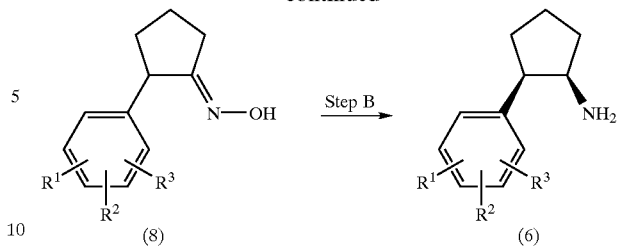

In Scheme IA, step A, the cyclopentanone of structure (7) is converted to the corresponding oxime of structure (8) under conditions well known in the art. For example, cyclopentanone (7) is dissolved in a suitable organic solvent, such as ethanol, treated with about 2 equivalents of aqueous sodium hydroxide and about 1.5 equivalents of hydroxylamine hydrochloride. The reaction mixture is stirred for about 8 to 16 hours at room temperature. It is then diluted with water and the precipitated oxime (8) is collected by filtration and dried under vacuum at about 35° C.

In Scheme IA, step B, oxime (8) is hydrogenated under standard conditions to provide the amine of structure (6). For example, oxime (8) is dissolved in a suitable organic solvent, such as ethanol, treated with a suitable catalyst, such as palladium on carbon, and placed under hydrogen at about 413.69 kPa (60 psi). The hydrogenation is carried out at about 40° C. for about 8 to 16 hours. The reaction mixture is then filtered and the filtrate concentrated under vacuum to provide the amine (8).

Scheme IB

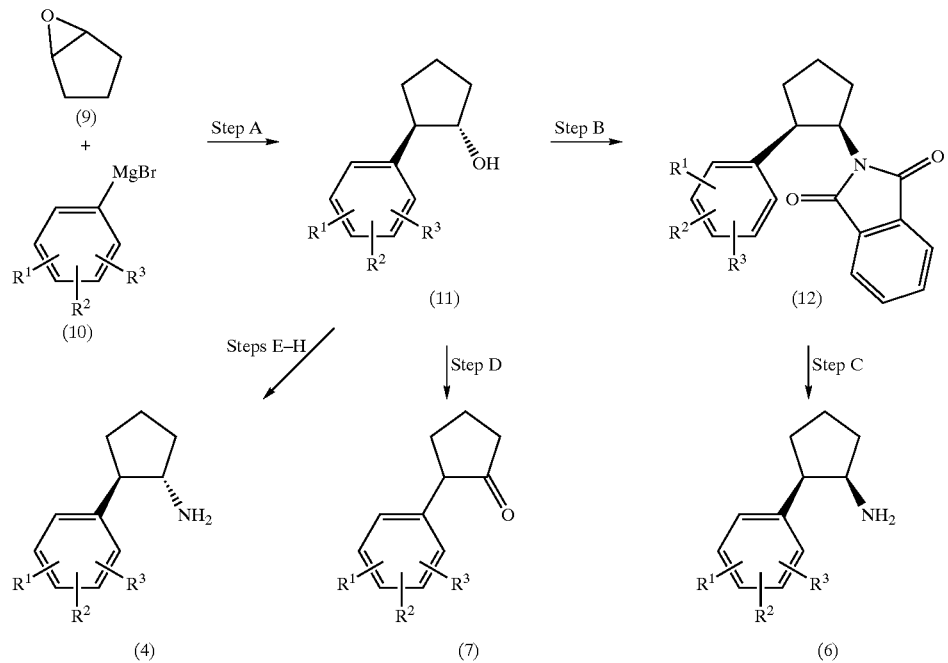

In Scheme IB, step A, the epoxide (9) is coupled with the Grignard reagent to provide the alcohol (11). For example, Grignard (10) is dissolved in a suitable organic solvent, such as tetrahydrofuran and treated with a catalytic amount of copper iodide. To this solution is slowly added the epoxide (9) dissolved in tetrahydrofuran. The reaction is exothermic. The reaction is stirred until the temperature reaches room temperature and it is quenched with aqueous ammonium chloride. The quenched reaction is extracted with a suitable organic solvent, such as diethyl ether. The organic extracts are combined, washed with aqueous ammonium chloride, dried over anhydrous magnesium sulfate, filtered, and concentrated under vacuum to provide alcohol (11).

In Scheme IB, step B, alcohol (11) is converted to the compound of structure (12) under standard conditions well known in the art. For example, about one equivalent of triphenylphosphine is dissolved in a suitable organic solvent, such as tetrahydrofuran. The solution is cooled to about 0° C. and a solution of about one equivalent of diisopropyl azodicarboxylate in tetrahydrofuran is added dropwise to the solution with stirring. To this reaction mixture is added about one equivalent of phthalimide followed by addition of about one equivalent of alcohol (11) dissolved in tetrahydrofuran maintaining the temperature between about 5° C. and 0° C. The reaction is then stirred at about 0° C. for about 4 hours, warmed to room temperature, and stirred for 4 to 12 hours. The reaction is then quenched with water and extracted with a suitable organic solvent, such as chloroform. The organic extracts are combined, washed with water, dried over anhydrous magnesium sulfate, filtered, and concentrated under vacuum to provide compound (12).

In Scheme IB, step C, compound (12) is converted to compound (6) in an exchange reaction well known in the art. For example, compound (12) is dissolved in a suitable organic solvent, such as toluene, and an excess of anhydrous hydrazine is added dropwise over about 15 minutes with stirring. The reaction mixture is stirred for about one hour at room temperature and then heated at about 90–95° C. for about 6 hours. The reaction mixture is then cooled to room temperature, filtered, the precipitate rinsed with toluene, the filtrates combined, concentrated under vacuum to provide compound (6).

Alternatively, compound (12) is dissolved in 2-aminoethanol and heated at about 80–90° C. for about 1 to 2 hours. The reaction is then diluted with diethyl ether, washed with dilute sodium hydroxide, brine, dried over anhydrous sodium sulfate, filtered, and concentrated to provide compound (6).

In Scheme IB, step D, compound (11) oxidized to the ketone of structure (7) under standard conditions well known in the art. For example, compound (11) is added dropwise to a suspension of an excess of pyridinium chlorochromate in a suitable organic solvent, such as methylene chloride. The reaction is stirred for about 8 to 48 hours at room temperature. It is then diluted with a diethyl ether, filtered through a pad of silica gel and the filtrate concentrated under vacuum to provide crude compound (7). This material can be purified by standard techniques, such as flash chromatography on silica gel with a suitable eluent, such as ethyl acetate/hexane.

In Scheme IB, steps E through H, compound (11) is converted to the amine (4) using standard techniques and reactions well known in the art. For example, in step E, compound (11) is subjected to Mitsunobu conditions to provide the cis-benzoate derivative. More specifically, compound (11) is dissolved in a suitable organic solvent, such as THF and combined with about 1.05 equivalents of diethyl azodicarboxylate (referred to herein as "DEAD"), about 1.2 equivalents of benzoic acid and about 1.2 equivalents of triphenylphosphine at about 0° C. The reaction is stirred for about 2 hours, allowed to warm to room temperature and then concentrated under vacuum. The crude residue can be purified by chromatography on silica gel with a suitable eluent, such as hexanes/methylene chloride to provide the cis-benzoate derivative.

In Scheme IB, step F, the cis-benzoate is hydrolyzed under standard conditions to provide the cis-alcohol. For example, the cis-benzoate is combined with 5% NaOH/methanol and stirred at room temperature for about 3 hours. The reaction mixture is then concentrated under vacuum, the residue dissolved in a suitable organic solvent, such as diethyl ether, which is washed with water. The organic phase is then dried over potassium carbonate, filtered, and concentrated under vacuum. The residue can be purified by chromatography on silica gel with a suitable eluent, such as hexanes/methylene chloride to provide the cis-alcohol.

In Scheme IB, step G, the cis-alcohol is converted to the phthalimide derivative in a manner analogous to the procedure described above in Scheme IB, step B.

In Scheme IB, step H, the phthalimide derivative is converted to the trans-amine (4) in a manner analogous to the procedure described above in Scheme IB, step C.

Scheme IC

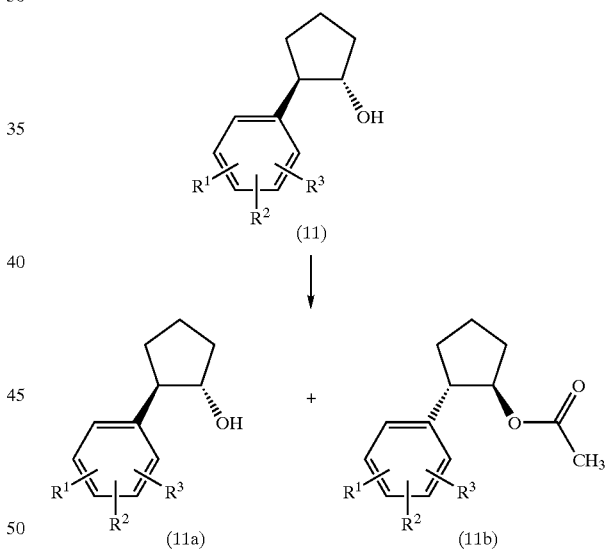

In Scheme IC, the compound (11) is subjected to an enzymatic resolution to provide the unreacted optically active alcohol (11a) and the optically active acetate (11b). For example, see the procedure described by Seemayer and Schneider, Recl. Trav. Chim. Pays-Bas, 110, 171–174 (1991), "Enzymatic Hydrolysis and Esterification. Routes to Optically Pure Cyclopentanols". More specifically, the alcohol (11) is dissolved in a suitable organic solvent, such as tert-butyl methyl ether and combined with a suitable enzyme, such as Candida antartctica B lipase. With stirring, about 0.5 to about 0.6 equivalents of vinyl acetate is added and the reaction is stirred at room temperature for about 2 to 4 hours. The reaction mixture is then filtered and the filtrated is concentrated under vacuum to provide a mixture of the optically active alcohol (11a) and optically active acetate (11b). These compounds are then readily separated from each other using standard techniques well known in the art, such as flash chromatography on silica gel with a suitable eluent, such as ethyl acetate/hexane.

The compounds of formulas I, Ia, Ia', Ia", and Ib can be prepared following the procedures set forth in Schemes II and IIA below. The reagents and starting materials are readily available to one of ordinary skill in the art. All substituents, unless otherwise specified are as previously defined.

crude material can be purified by standard techniques, such as flash chromatography or radial chromatography on silica gel with a suitable eluent, such as methylene chloride/ethyl acetate.

In Scheme II, step B, the compound of formula I wherein $R^1$, $R^2$ and $R^3$ represent hydrogen, can be converted to the compound of formula Ia wherein Y represents iodine. For example, compound of formula I is dissolved in a suitable solvent, such as glacial acetic acid. To this solution is added concentrated sulfuric acid followed by about 0.5 equivalents

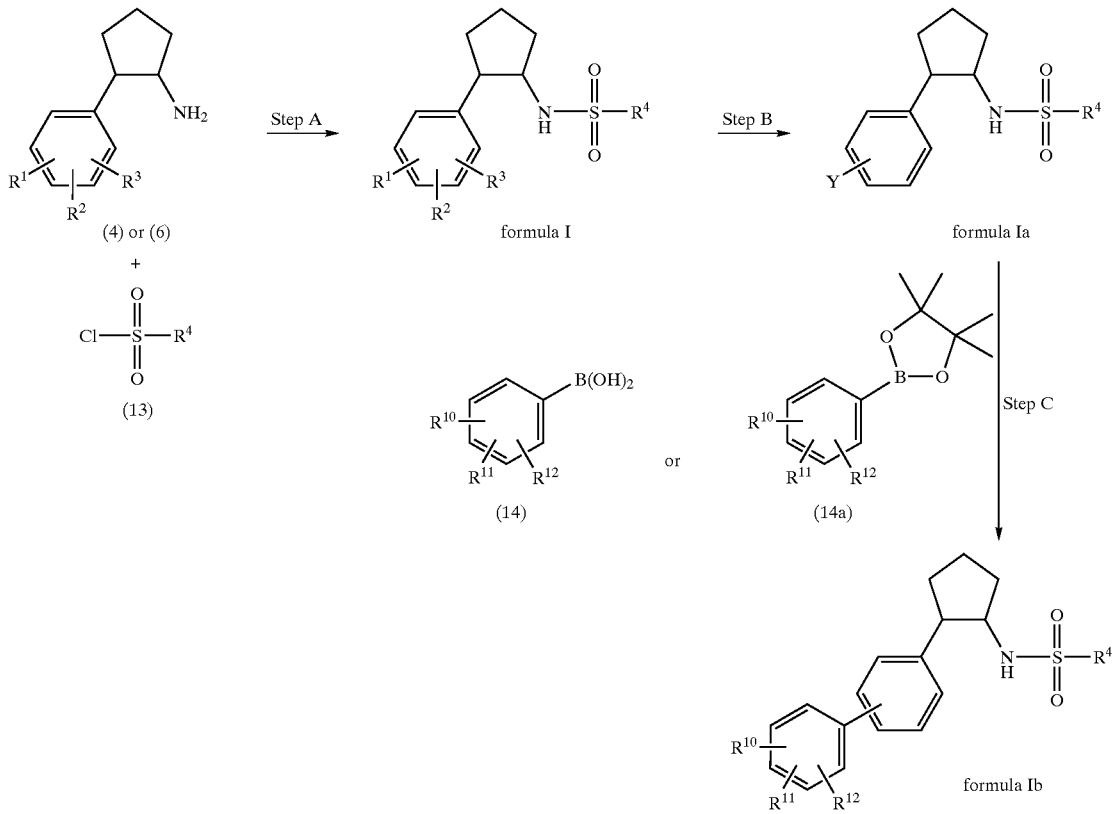

Scheme II

Y represents Br or I.

In Scheme II, step A, compound (4) or (6) is sulfonylated with sulfonyl chloride (13) under conditions well known in the art to provide the sulfonamide of formula (Ia). For example, compound (4) or (6) is dissolved in a suitable organic solvent, such as methylene chloride and cooled to about 0° C. under an atmosphere of nitrogen. About 1.1 equivalents of 1,8-diazabicyclo[5.4.0]undec-7-ene (DBU) are added followed by dropwise addition of about 1.1 equivalents of a sulfonyl chloride (13). The reaction mixture is then allowed to warm to room temperature and stirred for about 8 to 24 hours. Additional small amounts of DBU and sulfonyl chloride (9) may optionally be added in equivalent amounts as necessary in order to drive the reaction to completion. The reaction may be stirred for an additional 8 to 48 hours after additional amounts of DBU and sulfonyl chloride (13) are added. The reaction mixture is then diluted with a suitable organic solvent, such as methylene chloride and washed with 1N HCl. The organic phase is dried over anhydrous sodium sulfate, filtered and concentrated under vacuum to provide the crude compound of formula I. This of iodine and about 0.4 equivalents of diiodine pentoxide. The reaction mixture is protected from light and heated at about 90° C. for about 22 hours. The reaction mixture is then treated slowly with 10% aqueous sodium bisulfite, cooled to 0° C. for about one hour and the precipitate collected by filtration. The precipitate is dissolved in a suitable organic solvent, such as warm diethyl ether and then washed with water, saturated sodium bicarbonate, dried over anhydrous sodium sulfate, filtered and concentrated under vacuum to provide the iodo compound of formula Ia. Alternatively, one of $R^1$, $R^2$ or $R^3$ may represent Br in Scheme II, step A. In Scheme II, step C, the compounds of formula Ia, wherein Y represents Br or I, may be converted into compounds of formula Ib under conditions well known in the art, such as by reaction with an appropriate boronic acid (14) or boronic ester (14a) wherein $R^{10}$, $R^{11}$ and $R^{12}$ each individually represent hydrogen, halogen, $CF_3$, CN, $NO_2$, $NH_2$, (1–6C) alkyl, (1–6C)alkoxy, —$(CH_2)_n$$NHSO_2R^5$, —$(CH_2)_n$NHC(=O)$R^5$, or —$SO_2R^5$. See for example, International Publication Number WO 98/33496, published Aug. 6, 1998, the disclosure of which is hereby incorporated by reference. In addition, see Suzuki, A., *Journal of Organometallic Chemistry*, 576, 147–168 (1999), and Miyaura and Suzuki, *Chemical Reviews*, 95, 2457–2483 (1995) for examples of Suzuki-type coupling reactions and conditions. More specifically, the reaction is conveniently performed in the presence of a tetrakis (triarylphosphine)palladium(0) catalyst, such as tetrakis (triphenylphosphine)palladium(0) and a base such as potassium carbonate. Suitable solvents for the reaction include aromatic hydrocarbons, such as toluene. The temperature at which the reaction is conducted is conveniently in the range of from 0 to 150° C., preferably 75 to 120° C. Alternatively, the coupling reaction may be carried out using palladium diacetate with a suitable organic solvent, such as n-propanol or acetone. See for example, *Organic Synthesis* 1998, 75, 61; Goodson, F. E.; Wallow, T. I.; Novak, B. M. and *Organic Synthesis* 1998, 75, 53; Huff, B. E.; Koenig, T. M.; Mitchell, D.; Staszak, M. A. wherein analogous coupling conditions are employed.

More specifically, for example, a compound of formula Ia and about 1.2 equivalents of boronic acid (14) or boronic ester (14a) are dissolved in a suitable organic solvent, such as n-propanol. About 1.2 equivalents of potassium carbonate in water is added, followed by a catalytic amount of palladium acetate. The reaction mixture is heated at reflux for about 4 hours, filtered and the solid rinsed with ethyl acetate. The filtrates are combined, diluted with additional ethyl acetate, and washed with saturated sodium bicarbonate and brine. The organic phase is then dried over anhydrous sodium sulfate, filtered, and concentrated under vacuum to provide the crude compound of formula Ib. This crude material can then be purified by techniques well known in the art, such as flash chromatography or radial chromatography on silica gel with a suitable eluent, such as methylene chloride/ethyl acetate or reverse phase chromatography on a C18 column with a suitable eluent, such as aqueous acetonitrile.

Alternatively, compounds of formula Ia'

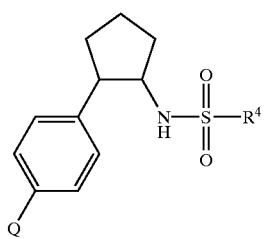

formula Ia' wherein Q represents a bromo or triflate group may be coupled to boronic acid (14) in a manner analogous to the procedures set forth above in Scheme II, step C.

The boronic acid (14) used as a starting material may be prepared by reacting a trialkyl borate, such as triisopropyl borate with an appropriate organolithium compound at reduced temperature. For example, 2-fluoro-benzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate. This is followed by hydrolysis with aqueous HCl.

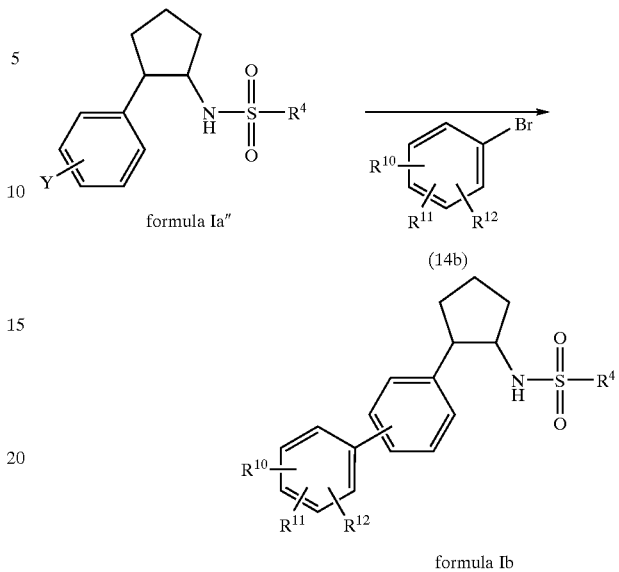

Scheme IIA formula Ia''

(14b)

formula Ib

Alternatively, compounds of formula Ib can be prepared under Suzuki-type reaction conditions as appreciated by one of ordinary skill in the art, from a compound of formula Ia'' and a compound of structure (14b). For example, the compound of formula Ia'' is dissolved in a suitable organic solvent, such as DMSO and treated with about 3 equivalents of potassium acetate. The reaction mixture is degassed and treated with about 1.1 equivalents of bis(pinacolato)diboron followed by addition of a catalytic amount of a suitable palladium catalyst, such as [1,1'-bis(diphenylphosphino)-ferrocene] dichloropalladium (II), complex with dichloromethane 1:1. The reaction mixture is then heated at about 80° C. under nitrogen with stirring for about 1 to about 4 hours. The reaction mixture is then cooled to room temperature and about one equivalent of the compound (14b) is added followed by addition of about 3 equivalents of sodium carbonate, water, and a catalytic amount of a suitable palladium catalyst, such as [1,1'-bis(diphenylphosphino)-ferrocene] dichloropalladium (II), complex with dichloromethane 1:1. The reaction mixture is then heat at about 105° C. for about 10 to about 20 hours. It is then allowed to cool and is diluted with a suitable organic solvent, such as methylene chloride. The mixture is washed with water, brine, dried over anhydrous magnesium sulfate, filtered and concentrated under vacuum to provide the crude compound formula Ib. This crude material can then be purified by techniques well known in the art, such as chromatography on silica gel with a suitable eluent, such as 1% methanol/methylene chloride to provide the purified compound of formula Ib.

The compounds of formulas Ic and Id can be prepared following the procedures set forth in Scheme III below. The reagents and starting materials are readily available to one of ordinary skill in the art. All substituents, unless otherwise specified are as previously defined.

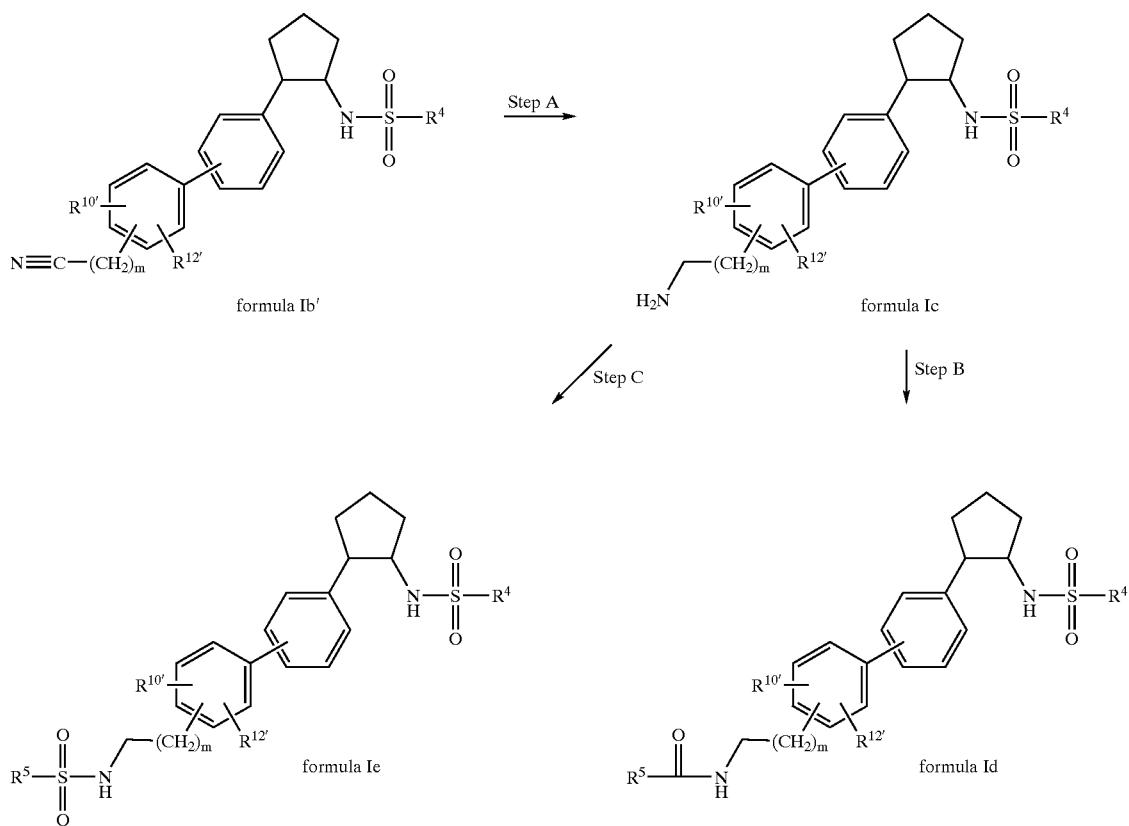

Scheme III

In Scheme III, step A compound of formula Ib' wherein $R^{10'}$ and $R^{12'}$ each independently represent hydrogen, halogen, $CF_3$, (1–6C)alkyl, or (1–6C)alkoxy and m is 0, 1, 2, or 3, is reduced under conditions well known in the art to provide the amine of formula Ic. For example, compound of formula Ib' is dissolved in a suitable organic solvent, such as dry tetrahydrofuran and treated with a suitable reducing agent, such as borane dimethyl sulfide. The reaction is heated at reflux for about 4 hours and then concentrated under vacuum. The residue is treated with diethyl ether:concentrated HCl:water:methanol (6:3:2:1)and stirred for about 30 minutes. The aqueous layer is then separated and the organic layer washed with water. The aqueous phases are combined, cooled to about 0° C., made basic with a suitable base, such as sodium hydroxide, and extracted with a suitable organic solvent, such as diethyl ether or ethyl acetate. The organic extracts are combined, dried over anhydrous sodium sulfate, filtered, and concentrated under vacuum to provide the amine of formula Ic.

In Scheme III, step B, the amine of formula Ic is converted to the amide of formula Id under standard coupling conditions as is well known in the art of peptide chemistry. For example, the amine of formula Ic is dissolved in a suitable organic solvent, such as dry methylene chloride. A slight excess of a suitable organic base, such as triethylamine is added followed by addition of about one equivalent of acetyl chloride. The reaction is stirred at room temperature for about 8 to 72 hours and then concentrated under vacuum to provide the crude amide of formula Id. This crude material is then purified by standard techniques, such as flash chromatography or radial chromatography on silica gel with a suitable eluent, such as methylene chloride:methanol.

In Scheme III, step C, the amine of formula Ic is readily converted to the sulfonamide of formula Ie under standard conditions well known in the art, for example in a manner analogous to the procedure previously described in Scheme II, step A.

The compounds of formulas Ig, Ih, Ij and Ik can be prepared following the procedures set forth in Scheme IV below. The reagents and starting materials are readily available to one of ordinary skill in the art. All substituents, unless otherwise specified are as previously defined.

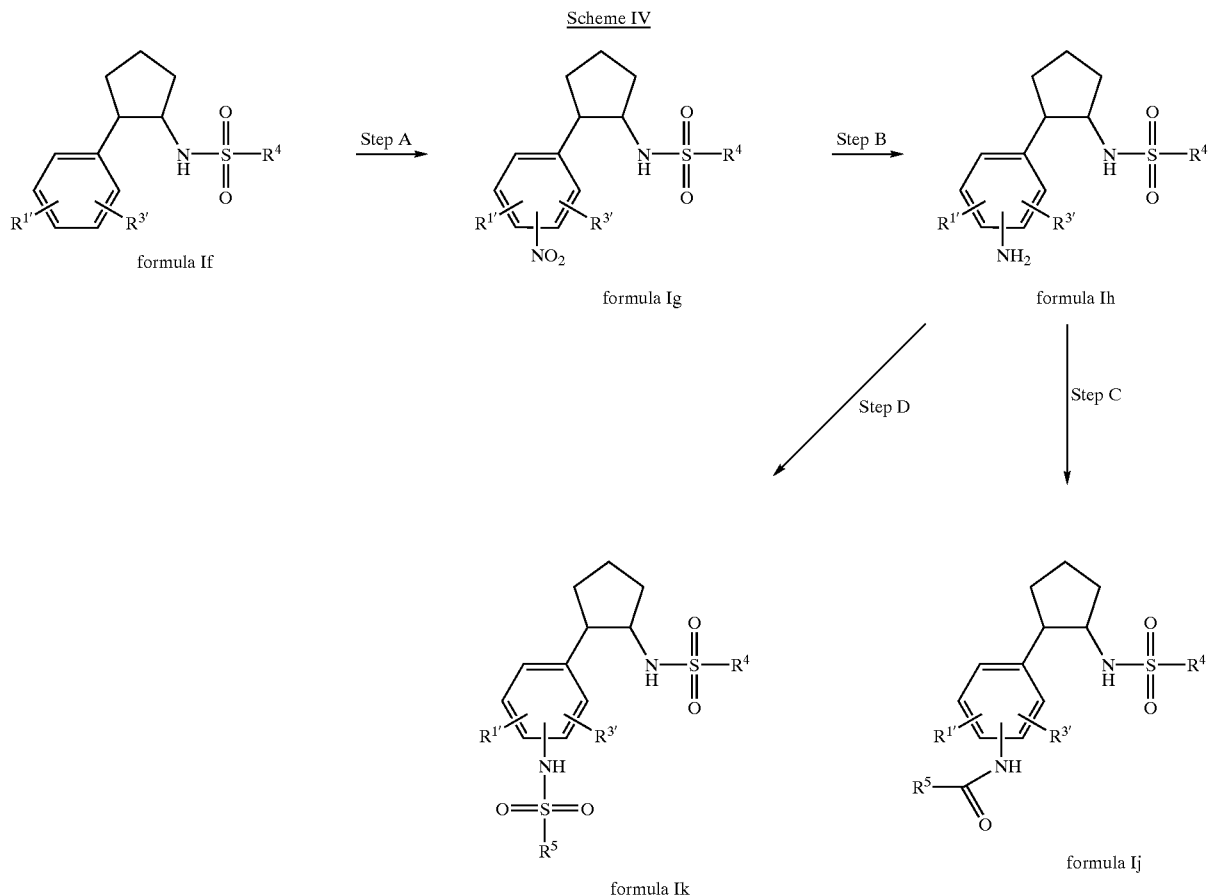

Scheme IV

In Scheme IV, step A, the compound of formula If, wherein $R^{1'}$ and $R^{3'}$ each independently represent hydogen, halogen, $CF_3$, (1–6C)alkyl, or (1–6C)alkoxy, is nitrated under standard conditions to provide the nitro compound of formula Ig. For example, compound of formula If is dissolved in a suitable acid, such as trifluoroacetic acid and an excess of sodium nitrate is added. The reaction mixture is stirred for about 5 hours at room temperature. It is then diluted with a suitable organic solvent, such as methylene chloride, washed with water, dilute sodium bicarbonate, dried over anhydrous sodium sulfate, filtered and concentrated under vacuum to provide the crude nitro compound of formula Ig. The crude material can then be purified using standard techniques such as flash chromatography or radial chromatography on silica gel with a suitable eluent, such as methylene chloride:ethyl acetate.

In Scheme IV, step B, the compound of formula Ig is reduced to the amine of formula Ih under conditions well known in the art. For example, the compound of formula Ig is dissolved in a suitable organic solvent, such as ethanol, treated with a suitable hydrogenation catalyst, such as palladium on carbon and placed under hydrogen at about 413.69 kPa (60 psi). The reaction mixture is hydrogenated at room temperature for about 4 to 12 hours, filtered, and concentrated under vacuum to provide the amine of formula Ih.

In Scheme IV, step C the amine of formula Ih is converted to the amide of formula Ij under standard coupling conditions as is well known in the art of peptide chemistry in a manner analogous to the procedure previously described in Scheme III, step B.

In Scheme IV, step D the amine of formula Ih is converted to the sulfonamide of formula Ik under standard conditions well known in the art, for example in a manner analogous to the procedure previously described in Scheme II, step A.

The compounds of formulas Im, In, Ip and Iq can be prepared following the procedures set forth in Scheme V below. The reagents and starting materials are readily available to one of ordinary skill in the art. All substituents, unless otherwise specified are as previously defined.

Scheme V

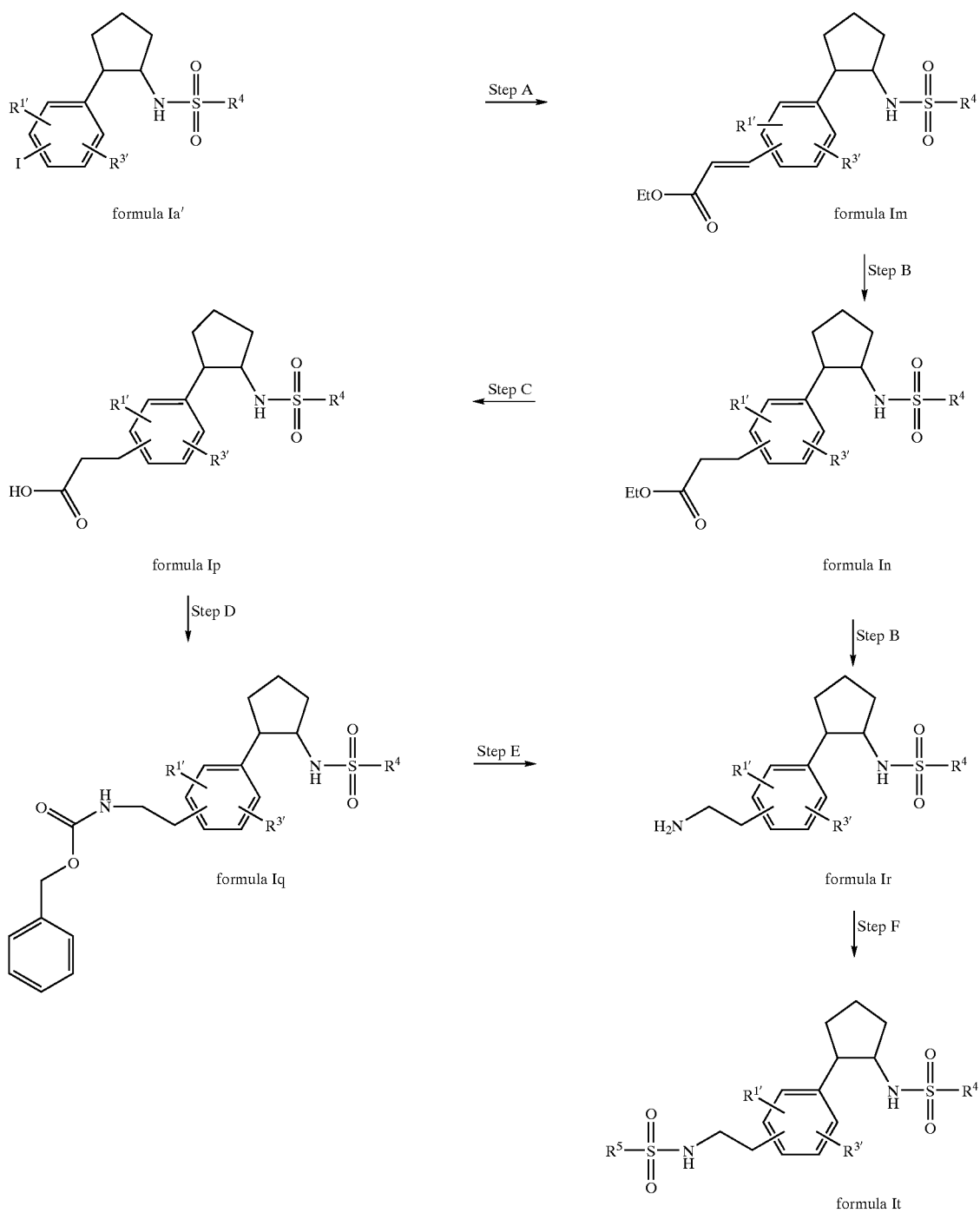

In Scheme V, step A, the compound of formula Ia' is converted to the compound of formula Im under standard conditions. For example, compound of formula Ia' is dissolved in a suitable organic solvent, such as DMF. It is then treated with an excess of ethyl acrylate and an excess of a suitable organic base, such as triethylamine followed by a catalytic amount of palladium acetate and triphenylphosphine. The reaction is then heated at about 80° C. under nitrogen for about 8 to 16 hours. The reaction is then allowed to cool and diluted with 75 mL of 10% aqueous sodium bisulfate. The quenched reaction mixture is then extracted with a suitable organic solvent, such as methylene chloride, the organic extracts dried over anhydrous sodium sulfate, filtered and concentrated under vacuum to provide the compound of formula Im. The crude product can be purified by radial chromatography on silica gel with a suitable eluent, such as methanol/methylene chloride.

In Scheme V, step B, the compound of formula Im is reduced under conditions well known in the art to provide the compound of formula In. For example, the compound of formula Im is placed in a Parr bottle and dissolved in a suitable organic solvent, such as ethyl acetate. It is treated with a catalytic amount of 10% palladium on carbon and the mixture is placed under hydrogen at about 275.80 kPa (40 psi) to about 413.69 kPa (60 psi) for about 4 to 16 hours at room temperature. The reaction is then filtered through diatomaceous earth and the filtrate is concentrated under vacuum to provide the compound of formula In. This material can be further purified, if necessary, for example by flash chromatography on silica gel with a suitable eluent, such as ethyl acetate/hexanes.

In Scheme V, step C, the compound of formula In is hydrolyzed to the acid of formula Ip under standard conditions. For example, the compound of formula In is dissolved in a suitable organic solvent, such as methanol with water added. The solution is treated with a suitable base, such as sodium hydroxide and the reaction is allowed to stir for about one to two days. The reaction mixture is then washed with a suitable organic solvent, such as ethyl acetate. The aqueous is cooled with an ice-water bath and made acidic with concentrated HCl. The acidified aqueous is then extracted with ethyl acetate, the organic extracts are combined, washed with water, dried over anhydrous sodium sulfate, filtered, and concentrated under vacuum to provide the acid of formula Ip.

In Scheme V, step D, the acid of formula Ip is converted to the carbamate of formula Iq under standard conditions. For example, the acid of formula Ip is dissolved in a suitable organic solvent, such as benzene and is treated with one equivalent of diphenylphosphoryl azide and one equivalent of triethylamine under nitrogen. The reaction is heated at reflux for about 4 hours, cooled to room temperature and stirred for about 8 to 16 hours. An equivalent of a suitable alcohol, such as methanol or benzyl alcohol is then added to the reaction, and the reaction is heated at reflux for about 8 hours. The reaction is then cooled to room temperature and stirred for about 8 to 16 hours. The reaction is then concentrated under vacuum and the residue purified by flash or radial chromatography on silica gel with a suitable eluent, such as ethyl acetate/hexanes.

In Scheme V, step E, the carbamate of formula Iq is deprotected under conditions well known in the art such as those conditions described by T. W. Green "Protective Groups in Organic Synthesis," John Wiley & Sons, 1981, pages 239–241, to provide the amine of formula Ir. For example, the carbamate of formula Iq is dissolved in a suitable organic solvent, such as methylene chloride and treated with trifluoroacetic acid. The reaction mixture is allowed to stir at room temperature for about 4 to 16 hours and then the solution is made basic with 2N sodium hydroxide. The reaction mixture is then extracted with a suitable organic solvent, such as ethyl acetate, the organic extracts are combined, washed with water, dried over anhydrous sodium sulfate, filtered, and concentrated under vacuum to provide the amine of formula Ir. This material may be further purified by radial chromatography on silica gel with a suitable eluent, such as methanol/methylene chloride. Alternatively, the carbamate of formula Iq may be deprotected using hydrogenation conditions well known in the art to provide the amine of formula Ir.

In Scheme V, step F, the amine of formula Ir is converted to the sulfonamide of formula It under standard conditions well known in the art, for example, in a manner analogous to the procedure described in Scheme II, step A above.

The following preparations and examples further illustrate the invention and represent typical syntheses of the compounds of formula I as described generally above. The reagents and starting materials are readily available to one of ordinary skill in the art. As used herein the term "Chromatotron®" (Harrison Research Inc., 840 Moana Court, Palo Alto Calif. 94306) is recognized by one of ordinary skill in the art as an instrument which is used to perform centrifugal thin-layer chromatography. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "kPa" refers to kilopascals; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to parts per million down-field from tetramethylsilane; "THF" refers to tetrahydrofuran; "PdCl$_2$(dppf)" refers to [1,1' bis (diphenylphosphino)-ferrocene] dichloropalladium (II); "MTBE" refers to tert-butyl methyl ether; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "DBU" refers to 1,8-diazabicyclo [5.4.0]undec-7-ene; "DEAD" refers to diethyl azodicarboxylate; and "RT" refers to room temperature.

PREPARATION 1

Chloro-bis-(2-phenyl-cyclopentyl)-borane

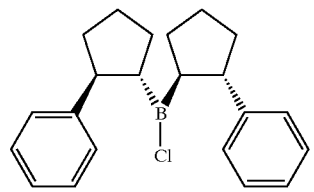

Scheme I, step A: Modification of H. C. Brown et. al., *Tetrahedron Asymmetry*, 7, 3527–3534 (1996). 1-Phenylcyclopentene (commercial 96%)(10.0 g, 69.4 mmol) was placed in an oven-dried flask under nitrogen and diluted with 60 mL of dry methylene chloride. The solution was cooled to 0° C. and monochloroborane-methyl sulfide complex (3.6 mL, 34.7 mmoL) was added dropwise via syringe. The solution was allowed to warm to room temperature and stirred overnight. The solvent is removed by aspirator vacuum under a nitrogen atmosphere to provide a crude colorless oil. This oil is used directly in the next step without further characterization.

PREPARATION 2

Methyl-bis-(2-phenyl-cyclopentyl)-borane

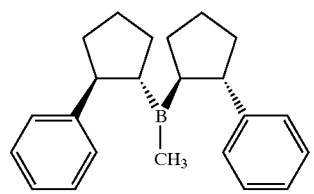

Scheme I, step B: Chloro-bis-(2-phenyl-cyclopentyl)-borane from preparation 1 was diluted with 60 mL of dry hexanes under nitrogen. The solution was cooled to 0° C. and a 2M solution of trimethylaluminum in hexanes (5.8 mL) was added dropwise causing the reaction to turn orange. The reaction was allowed to warm to room temperature and stirred for 1.5 hours. During this time a red-brown mass precipitated out of solution, leaving a yellow supernatant. The hexane supernatant was transferred via cannula to a nitrogen flushed separatory funnel containing 50 mL of saturated aqueous ammonium chloride. The organic phase becomes colorless and was transferred via cannula to a dry flask containing sodium sulfate for drying. The solution was then transferred via cannula to a dry, nitrogen-flushed flask and the solvent removed under aspirator vacuum and nitrogen. The clear oil was used directly without further characterization.

PREPARATION 3

(+,−) Trans-2-phenyl-cyclopentylamine

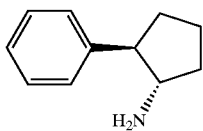

Scheme I, step C: Methyl-bis-(2-phenyl-cyclopentyl)-borane (theoretical 34.7 mmoL) from preparation 2 was diluted with 40 mL of dry tetrahydrofuran. 8.3 g (72.9 mmol) of hydroxylamine-O-sulphonic acid (HSA) was slurried in a separate dry flask in 60 mL of THF and small portions are transferred via cannula to control the exothermic reaction. The cloudy white solution was stirred at room temperature for 24 hours. The reaction mixture was filtered and the THF removed in vacuo. The residue was treated with 30 mL of concentrated HCl, 15 mL of methanol, 20 mL of water and 60 mL of diethyl ether and stirred at room temperature for 30 minutes. The aqueous phase was collected and the organic phase washed with water and combined with the aqueous phase. The aqueous phase was cooled to 0° C., layered with diethyl ether, and made strongly basic with sodium hydroxide pellets. The organic phase was separated and the aqueous phase extracted with diethyl ether (2x) and ethyl acetate (1x). The organic phases were combined and dried over sodium sulfate. The filtrate was concentrated to 5.96 (53%) of the title compound as a yellow oil.

Mass Spectrum (ES MS): M+1=162.

PREPARATION 4

(5-Nitro-cyclopent-1-enyl)-benzene

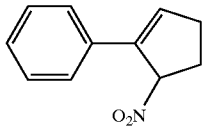

Scheme I, step D: (5-Nitro-cyclopent-1-enyl)-benzene was prepared according to the procedure of F. G. Bordwell et. al., J. Org. Chem., 1765–1769, 1963. The title compound was prepared by nitration of 1-phenylcyclopentene (3.0 g, 20.8 mmol) and purified by radial chromatography eluting with 85:15 hexanes:ethyl acetate to yield 0.63 g (12%) as a yellow oil. The NMR was consistent with the assigned structure.

PREPARATION 5

(+,−) Cis -2-phenyl-cyclopentylamine

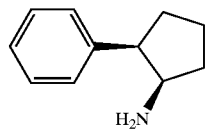

Scheme I, step E: (5-Nitro-cyclopent-1-enyl)-benzene (0.63 g, 3.3 mmol) from preparation 4 above, was hydrogenated in 25 mL of ethanol using 0.16 g of 5% Pd/C at room temperature overnight at 413.69 kPa (60 psi). The solution was filtered over celite and concentrated in vacuo to 230 mg (43%) of the title compound as a colorless oil. The NMR was consistent with the assigned structure. Mass Spectrum (ES MS): M+1=162.

PREPARATION 6

(+,−) 2-Phenyl-cyclopentanone Oxime

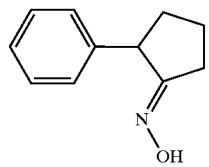

Scheme IA, step A: 2-Phenyl-cyclopentanone (prepared according to R. Sudha et. al. J. Org. Chem., 61, 1877–1879, 1996) (1.0 g, 6.2 mmol) was dissolved in 20 mL of absolute ethanol. To this solution was added sodium hydroxide (0.5 g, 12.5 mmol) dissolved in 10 mL water followed by hydroxylamine hydrochloride (0.65 g, 9.36 mmol) and stirred overnight at room temperature. The reaction was diluted with water and the precipitate collected by filtration. The white solid was vacuum oven-dried at 35° C. for 30 minutes to give 0.75 g (69%) of the title compound. The NMR was consistent with the assigned structure.

Analysis calculated for $C_{11}H_{13}NO$: % C, 75.40; % H, 7.48; % N, 7.99. Found: % C, 75.32; % H, 7.22; % N, 7.92. Mass Spectrum (ES MS): M+1=176.

PREPARATION 7

Alternative Synthesis of (+,−) Cis -2-Phenyl-cyclopentylamine

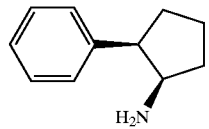

Scheme IA, step B: (+,−) 2-Phenyl-cyclopentanone oxime from preparation 6 above was dissolved in 35 mL of ethanol and hydrogenated using 90 mg of 5% Pd/C at 40° C. overnight at 413.69 kPa (60 psi). The solution was filtered and concentrated in vacuo to give 0.43 g (62%) of a colorless oil. Some dimeric material resulted by this procedure according to the mass spec. The cis:trans ratio was estimated to be 4:1. The amine was used directly without further purification. The NMR was consistent with the assigned structure.

Mass Spectrum (ES MS): M+1=306, 162.

PREPARATION 8

Alternative Synthesis of (+,−) Cis-2-Phenyl-cyclopentylamine

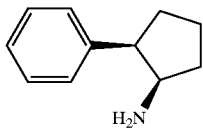

Scheme IB, step A: A one liter three necked round bottom flask equipped with a mechanical stirrer, addition funnel, thermometer is charged with 1M THF solution of phenyl-magnesium bromide (300 mL, 300.0 mmol) and copper iodide (3.8 g, 20.0 mmol). To this reaction mixture was then added cyclopentene oxide (25.23 g, 300.0 mmol) dissolved in THF (50.0 mL) dropwise over a period of 60 minutes (reaction was quite exothermic, reaching THF reflux by the end of addition). The reaction mixture was then stirred to room temperature and quenched with 25% solution of ammonium chloride (200.0 mL). Added ether (80.0 mL) and separated upper organic layer. Washed organic layer with 25% ammonium chloride solution, dried with anhydrous magnesium sulfate, filtered and concentrated filtrate to provide (+,−) trans-2-phenyl-cyclopentanol as a brown oil (mass =47.7 g);

$^1$H nmr (CDCl$_3$) δ 1.6–1.8 (m, 4H), 2.0–2.2 (m, 2H), 2.8–2.88 (m, 1H), 4.13–4.16 (m, 1H), 7.2–7.4 (aromatic, 5H); $^{13}$C (CDCl$_3$) δ 22.46, 32.57, 34.64, 55.13, 81.11, 127.10, 128.11, 129.25, 144.05).

Scheme IB, step B: A 500 mL three necked round bottom flask equipped with a mechanical stirrer, thermometer, reflux condenser, addition funnel and a nitrogen blanket is charged with triphenylphosphine (16.19 g, 61.73 mmol) and THF (200 mL). To the solution at 0° C. was added dropwise, a solution of diisopropyl azodicarboxylate (12.15 mL, 61.73 mmol) dissolved in THF (30 mL) over a period of 10 minutes. A massive precipitate formed immediately after addition. To the slurry was then added solid phthalimide (9.08 g, 61.73 mmol), followed by a solution of 5-phenylcyclopentane-1-ol (10.0 g, 61.73 mmol) dissolved in THF (30 mL) over a period of 20 minutes maintaining temperature at 0° C. to 5° C. (reaction mixture went into solution by the end of alcoholic substrate addition). Reaction was then stirred at 0° C. for 4.0 hours and brought to room temperature overnight for convenience. Quenched reaction with water (200 mL) and extracted organics with chloroform (200 mL). Washed the organic with water (100 mL) and dried with anhydrous magnesium sulfate. Subsequent filtration and concentration under reduced pressure afforded an oil which solidified on equilibrating to room temperature. To the precipitate was then added hexane (250.0 mL) with vigorous stirring. Filtered off triphenylphosphine oxide precipitate and concentrated filtrate to an oil. Silica gel plug filtration of the oil with 1:1 ethyl acetate:hexanes and subsequent concentration of product fractions afforded an off white precipitate of (+,−) Cis-2-(2-phenyl-cyclopentyl)-isoindole-1,3-dione (mass=12.5 g, 69.6%); 1H nmr (CDCl$_3$) δ 1.6–1.8 (m, 1H), 2.0–2.1 (m, 1H), 2.2–2.35 (m, 2H), 2.4–2.68 (m, 2H), 3.39–3.5 (m, 1H), 5.0–5.1 (m, 1H), 6.9–7.15 (aromatic, 5H), 7.52–7.64 (aromatic, 4H); $^{13}$C (CDCl$_3$) δ 25.4, 28.89, 30.56, 50.34, 54.60, 122.89, 126.44, 128.01, 128.41, 131.67, 139.68, 168.86).

Scheme IB, step C: A 1000 mL three necked flask equipped with a mechanical stirrer, thermometer, addition funnel and a reflux condenser is charged with (+,−) cis-2-(2-phenyl-cyclopentyl)-isoindole-1,3-dione (27.34 g, 93.91 mmol) and toluene (400.0 mL). To this solution was added anhydrous hydrazine (29.48 mL, 939.09 mmol) dropwise over a period of 15 minutes. Stirred reaction at room temperature for 60 minutes then heated it at 90° C.–95° C. for 6.0 hours. Cooled reaction to room temperature, filtered precipitates, washed cake with toluene (50.0 mL) and concentrated filtrate to provide the title compound as an oil (mass=15.13 g);

$^1$H nmr (CDCl$_3$) δ 0.6–0.8 (b, 1H), 1.5–1.6 (m, 1H), 1.63–1.69 (m, 1H), 1.9–2.0 (m, 2H), 2.0–2.1 (m, 2H), 3.05–3.1 (m, 1H), 3.4–3.7 (m, 1H), 7.19–7.35 (aromatic, 5H); $^{13}$C (CDCl$_3$) δ 23.05, 27.96, 34.98, 51.75, 56.68, 126.86, 128.96, 129.20, 142.00).

PREPARATION 9

(+,−) Cis-2-p-tolyl-cyclopentylamine

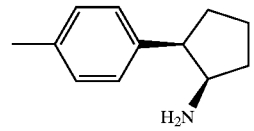

Preparation of (+,−) Trans-2-p-tolyl-cyclopentanol.

Scheme IB, step A: The title compound was prepared in a manner analogous to the procedure described in preparation 8, Scheme IB, step A, starting with 10.0 mL of a 1M ethereal solution of p-tolylphenylmagnesium bromide(100.0 mmol). The same workup gave 1.7 g of a crude yellow oil. The intermediate title compound was purified by radial chromatography eluting with 25:75 EtOAc:hexanes to give 1.48 g (84%) as a colorless oil.

$^1$H nmr (CDCl$_3$) δ 1.6–1.84 (m, 4H), 2.0–2.2 (m, 2H), 2.30 (s, 3H), 2.78–2.85 (m, 1H), 4.07–4.13 (m, 1H), 7.09–7.17 (aromatic, 4H).

Preparation of (+,−) Cis-2-(2-p-tolyl-cyclopentyl)-isoindole-1,3-dione.

Scheme IB, step B: The title compound was prepared in a manner analogous to the procedure described in preparation 8, Scheme IB, from (+,−) trans-2-p-tolyl-cyclopentanol (1.48 g, 8.4 mmol, prepared above). Following the same workup gave a crude yellow oil which was triturated with ethyl acetate and the triphenylphosphine oxide removed by filtration. The title compound was purified by radial chromatography eluting with ethyl acetate and then again eluting with methylene chloride to give 0.69 g (27%) of the intermediate title compound as an oil which solidified under vacuum.

$^1$H nmr (CDCl$_3$) δ 1.6–1.73 (m, 1H), 1.88–2.03 (m, 1H), 2.10 (s, 3H), 2.15–2.22 (m, 2H), 2.4–2.6 (m, 2H), 3.32–3.41 (m, 1H), 4.95–5.01 (m, 1H), 6.82 (d, 2H, J=9 Hz), 7.00 (d, 2H, J=9 Hz), 7.52–7.62 (m, 4H); Analysis calculated for $C_{20}H_{19}NO_2 \times 0.2$ $H_2O$: % C, 77.75; % H, 6.33; % N, 4.53. Found: % C, 77.93; % H, 6.18; % N, 4.57.

Preparation of the Final Title Compound.

Scheme IB, step C: To (+,−) cis-2-(2-p-tolyl-cyclopentyl)-isoindole-1,3-dione (582 mg, 1.91 mmol, prepared above) was added ethanolamine and the solution was heated to 80° C. and stirred for 30 minutes. ES-MS indicated the reaction was not complete and the reaction was heated to 90° C. for 30 minutes. The reaction was diluted with ethyl ether and washed with dilute sodium hydroxide, brine and the organic layer dried over sodium sulfate. The filtrate was concentrated to provide 313 mg (94%) of the final title compound, (+,−) cis-2-p-tolyl-cyclopentylamine, as a colorless oil.
Mass Spectrum (ES MS): M+1=176.

PREPARATION 10

(+,−) Cis-[2-(4-bromo-phenyl)-cyclopentylamine Oxalate

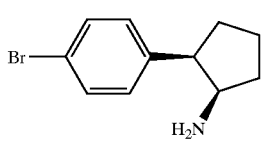 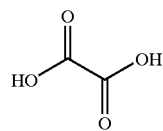

Scheme IB, Step A: A 500 mL three necked flask equipped with a mechanical stirrer, thermometer, addition funnel under a blanket of nitrogen was charged with 4-bromophenylmagnesium bromide (43.6 g, 167.57 mmol), anhydrous THF (120.0 mL) and catalytic copper iodide (1.59 g, 8.38 mmol) with vigorous stirring at room temperature for 10.0 minutes. To this mixture was then added dropwise a solution of cyclopentene oxide (14.62 mL, 167.57 mmol) dissolved in THF (20.0 mL) over a period of 20.0 minutes. Reaction was quite exothermic, reaching the reflux of THF by the end of addition. The reaction was brought to room temperature and stirred for 120.0 minutes, after which reaction was reversed quenched carefully into a 25% ammonium chloride solution (100.0 mL). Extracted with methylene chloride (150.0 mL), dried with anhydrous magnesium sulfate, filtered and concentrated at reduced pressure to give an oil (19.0 g). Silica gel plug filtration of the oil with 1:1 ethyl acetate and hexane, and subsequent concentration of fractions 2 and 3 afforded the bromophenylcyclopentyl carbinol as a light red oil (mass=13.61 g, 34% wt. Yield;

$^1$H NMR (CDCl$_3$) δ 1.60–2.20 (m, 6H), 2.80–2.90 (m, 1H), 4.10–4.20 (m, 1H), 7.10 (d, 2H), 7.40–7.50 (d, 2H); $^{13}$C NMR (CDCl$_3$) δ 22.38, 32.45, 54.40, 80.98, 121.00, 129.86, 132.25, 143.00.

Scheme IB, step B: A 500 mL three necked flask equipped with a mechanical stirrer, thermometer, addition funnel under a blanket of nitrogen was charged with triphenylphosphine (8.75 g, 32.68 mmol) and THF (200.0 mL). To this solution at 5° C. was added dropwise a solution of diisopropylazodicarboxylate (6.43 mL, 32.68 mmol) dissolved in THF (10.0 mL) over a period of 10.0 minutes (reaction exothermed to 35° C.). Stirred for 5.0 minutes then added phthalimide (4.80 g, 32.68 mmol) with vigorous stirring (a massive off yellow precipitate formed). To this mixture was then added a solution of bromophenylcyclopentyl carbinol (7.84 g, 32.68 mmol) dissolved in THF (40.0 mL) over a period of 30.0 minutes maintaining temperature at 5° C. (precipitate went into solution by the end of addition). Stirred reaction to room temperature overnight, then quenched with water (250.0 mL) and extracted with methylene chloride (250.0 mL). The organic solution was then dried with anhydrous magnesium sulfate, filtered, and concentrated filtrate to an oil. Added ethyl ether(60.0 mL) with stirring, filtered off triphenylphosphine oxide precipitates and concentrated filtrate to an oil. Silica gel plug filtration of the oil with 1:1 ethyl acetate and hexane and subsequent concentration of fractions 2 and 3 afforded the bromophenylcyclopentyl phthalimido as an oil which solidified on equilibrating to room temperature, mass=3.47 g, 29% wt. Yield;

$^1$H NMR (CDCl$_3$) δ 1.03–1.77 (m, 1H), 2.00–2.09 (m, 1H), 2.16–2.27 (m, 2H), 2.35–3.32 (m, 2H), 7.00 (d, 2H), 7.2. (d, 2H), 7.57–7.67 (m, 4H); $^{13}$C NMR (CDCl$_3$) δ 25.17, 28.93, 30.58, 49.59, 54.00, 119.96, 122.78, 129.83, 130.79, 131.23, 133.67, 138.48, 168.43.

Scheme IB, step C: A 250 mL three necked round bottom flask equipped with a mechanical stirrer, thermometer and an addition funnel was charged with bromophenylcyclopentyl phthalimido (3,47 g, 9.32 mmol), toluene (150 mL) and anhydrous hydrazine (5.0 mL) at room temperature. The reaction was stirred for 120 minutes, then heated at 90° C.–95° C. for 180 minutes (an off yellow precipitate was formed). Concentrated reaction mixture to a constant weight by removing organic solvents. Added fresh toluene (150.0 mL) with stirring, filtered off precipitates, then concentrated filtrate to provide the free base of the title compound as an oil, mass=1.75 g, 75.3% wt. Yield.

$^1$H NMR (CDCl$_3$) δ 0.86 (b, 2H), 1.50–1.60 (m, 1H), 1.60–1.79 (m, 1H), 1.80–2.00 (m, 4H), 3.00 (m, 1H), 3.5 (m, 1H), 7.10 (d, 2H), 7.4 (d, 2H); $^{13}$C NMR (CDCl$_3$) δ 21.3, 28.00, 31.00, 36.20, 120.00, 128.00, 131.00, 132.00, 141.00. The above free base of the title compound (1.59 g) was dissolved in ethyl acetate (50 mL) and treated with oxalic acid (0.59 g, 1.0 eq). The slurry was stirred for 60 minutes, concentrated to provide an off yellow solid, treated with ethyl acetate (80.0 mL) with stirring, filtered, and the precipitate was dried under house vacuum at 35° C. to provide the title compound (1.04 g).

$^1$H NMR (DMSO) δ 1.60–1.80 (m, 2H), 1.81–1.99 (m, 2H), 2.10–2.15 (m, 2H), 3.25–3.10 (m, 1H), 3.69–3.75 (m, 1H); $^{13}$C NMR (DMSO) δ 22.66, 28.29, 31.11, 48.00, 55.74, 121.45, 132.08, 132.54, 138.41, 165.53.

PREPARATION 11

(+,−) Cis-[2-(4-chloro-phenyl)-cyclopentylamine Oxalate

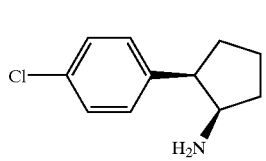 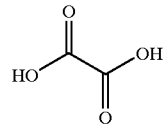

Scheme IB: The title compound was prepared from 4-chlorophenylmagnesium bromide and cyclopentene oxide in a manner analogous to the procedure described in preparation 10.

PREPARATION 12

(+,−) Cis-[2-(3,5-difluoro-phenyl)-cyclopentylamine

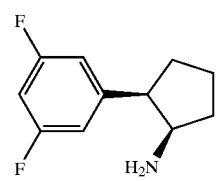

The title compound was prepared from 3,5-difluorophenylmagnesium bromide and cyclopentene oxide in a manner analogous to the procedure described in preparation 10.

PREPARATION 13

(+,−) Cis-[2-(4-fluoro-phenyl)-cyclopentylamine

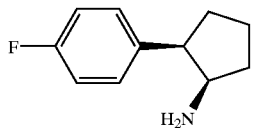

The title compound was prepared from 4-fluorophenylmagnesium bromide and cyclopentene oxide in a manner analogous to the procedure described in preparation 10.

PREPARATION 14

(+,−) Cis-[2-(3-fluoro-phenyl)-cyclopentylamine

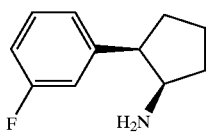

The title compound was prepared from 3-fluorophenylmagnesium bromide and cyclopentene oxide in a manner analogous to the procedure described in preparation 10.

PREPARATION 15

(+,−) Cis-[2-(3,4-difluoro-phenyl)-cyclopentylamine

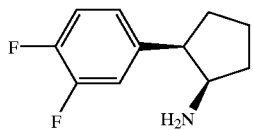

The title compound was prepared from 3,4-difluorophenylmagnesium bromide and cyclopentene oxide in a manner analogous to the procedure described in preparation 10.

PREPARATION 16

4-(4,4,5,5-Tetramethyl-[1,3,2]dioxaborolan-2-yl)-benzoic Acid

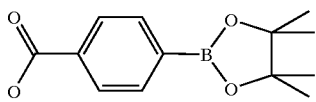

4-Carboxyphenylboronic acid (10.0 g, 60.3 mmol) was suspended in 100 mL of toluene and pinnacol added (7.1 g, 60.3 mmol). The reaction was heated to reflux with a Dean-Stark trap attached. The reaction became homogenous upon heating. After 2 h reflux the reaction was allowed to stand overnight and white needles were collected by filtration and rinsed with toluene. The title compound was vacuum dried to 12.2 g (81%).

Mass Spectrum (FD MS): M=248. Analysis calculated for $C_{13}H_{17}BO_4$: % C, 62.94; % H, 6.91; Found: % C, 62.71; % H, 6.91.

PREPARATION 17

N-Methyl-4-(4,4,5,5-tetramethyl-[1,3,2]dioxaborolan-2-yl)-benzamide

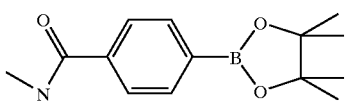

The acid from preparation 16 (6.0 g, 24.2 mmol) was suspended in 20 mL of thionyl chloride, 3 drops of DMF added and the reaction heated to reflux under nitrogen. The solid dissolved upon warming. After refluxing 2 h the reaction was concentrated in vacuo and dried to a white solid under vacuum. The acid chloride was dissolved in 30 mL of THF and cooled to 0° C. 40% aqueous methylamine (10.4 mL) was added dropwise. After the addition was complete the ice bath was removed and stirring continued for 30 min. The reaction was concentrated in vacuo (3×1:1 EtOAc:toluene) then extracted with ether/water. The organic layer was dried over sodium sulfate, filtered and concentrated to 5.2 g (83%) of the title compound as a white solid.

Mass Spectrum (FD MS): M=261. Analysis calculated for $C_{14}H_{20}BNO_3$: % C, 64.40; % H, 7.72; % N, 5.36. Found: % C, 64.09; % H, 7.70, % N, 5.28.

PREPARATION 18

(+,−) Cis Benzoic acid 2-(4-bromo-phenyl)-cyclopentyl Ester

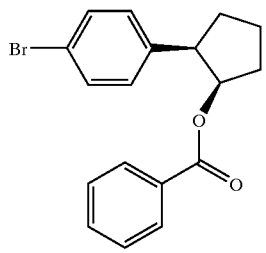

Scheme IB, step E: Into a 250 mL 3 neck flask fitted with a stirrer and thermometer was placed 5.00 g (24.7 mmol) of DEAD and 3.50 g (28.7 mmol) benzoic acid in THF (50 mL). 5.78 g (24.0 mmol) of the alcohol from preparation 10 and 7.50 g. (28.6 mmol) of triphenylphosphine in THF (50 mL) was added dropwise while stirring at 0° C. under a nitrogen atmosphere. After 2 hours at this temperature, TLC showed that the reaction was complete. Solution was let warm to room temperature and then concentrated under reduced vacuum to yield 9.14 g of an oil. This material was purified via silica gel chromatography employing the Water's prep. 2000 and eluting with an isocratic solvent of hexane/methylene chloride 1:1 to yield 3.74 g (45%) of title compound as a slowly crystallizing oil. Ion spray M.S. 344 (M*−1): Calculated for: $C_{18}H_{17}O_2Br$ Theory: C 62.62, H 4.96 Found: C 62.40, H 4.90.

PREPARATION 19

(+, −) Cis 2-(4-Bromo-phenyl)-cyclopentanol

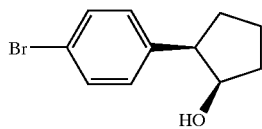

Scheme IB, step F: To the compound prepared in preparation 18, 3.70 g (10.7 mmol) was added 5% NaOH/MeOH (75 mL, excess) in a 250 mL single-neck flask and stirred at room temperature for 3 hours. The reaction mixture was then concentrated under reduced pressure to yield a semi-solid. This material was taken into ether and washed once with water, dried over potassium carbonate, and concentrated under reduced vacuum to yield 3.01 g of an oil. This material was purified via silica gel chromatography employing the Water's prep. 2000 and eluting with an isocratic solvent of hexane/methylene chloride 1:1 to yield 2.31 g (90%) of a clear oil. NMR was consistent with the proposed structure. Ion spray M.S. 241 (M*): Calculated for: $C_{11}H_{13}OBr$. Theory: C 54.79, H 5.43 Found: C 54.91, H 5.12.

PREPARATION 20

(+,−) Trans 2-[2-(4-Bromo-phenyl)-cyclopentyl]-isoindole-1,3-Dione

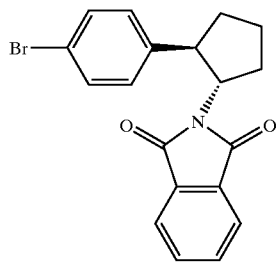

Scheme IB, step G: Into a 500 mL 3N flask fitted with a stirrer and thermometer, 8.49 g (42.0 mmol) of DEAD in THF (25 mL) was added dropwise to 10.37 g (42.0 mmol) of triphenylphosphine in THF (175 mL) while stirring at 0° C. under a nitrogen atmosphere. A white precipitate formed. At this same temperature, 6.18 g (42.0 mmol) of phthalimide in THF (25 mL) was added dropwise followed by 10.15 g (42.0 mmol) of the compound prepared in preparation 19 in THF (25 mL) added dropwise at 0° C. The reaction was then stirred at this temperature for 4 hours and then allowed to warm to room temperature. The mixture was poured into water and the desired material was extracted with ethyl acetate. The organic layer was washed once with water, dried over potassium carbonate, and concentrated under reduced vacuum to yield 27.31 g of a semi-solid. This material was extracted with 3–500 mL portions of hexane and filtered. The filtrate was concentrated under reduced vacuum to yield 14.71 g of a yellow solid. This material was purified via silica gel chromatography employing the Water's prep. 2000 and eluting with an isocratic solvent of hexane/ethyl acetate 9:1 to yield 5.20 g (34%) of a white solid. Ion spray M.S. 372.1 (M*+2):

Calculated for: $C_{19}H_{16}NO_2Br$; Theory: C 61.61, H 4.36, N 3.78; Found: C 61.41, H 4.24, N 3.81.

PREPARATION 21

(+,−) Trans 2-(4-Bromo-phenyl)-cyclopentylamine

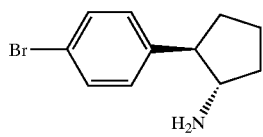

Scheme IB, step H: Into a 250 mL 3N flask fitted with a stirrer, thermometer, and condenser was placed 5.10 g (14 mmol) of (+,−) trans 2-[2-(4-bromo-phenyl)-cyclopentyl]-isoindole-1,3-dione in toluene (60 mL), prepared in preparation 20. To this mixture was added dropwise 4.50 g (140 mmol) of hydrazine in toluene (2 mL) while stirring at room temperature under a nitrogen atmosphere. The reaction was then heated at 95° C. for 6 hours. The reaction was cooled to room temperature and stirred overnight. In the morning, the precipitate that had formed was filtered and the filtrate was dried over potassium carbonate and then concentrated under reduced vacuum to yield 3.41 g of an oil. This material was purified via silica gel chromatography employing the Water's prep. 2000 and eluting with an isocratic solvent of methylene chloride/methanol 9:1 to yield (+,−) trans 2-(4-bromo-phenyl)-cyclopentylamine (3.30 g, 98%) as a light oil. Ion spray M.S. 239.1 (M*−1):

Calculated for: $C_{11}H_{14}NBr$; Theory: C 55.01, H 5.87, N 5.83; Found: C 53.18, H 5.50, N 5.39.

PREPARATION 22

4-Amino-benzoic Acid Ethyl Ester

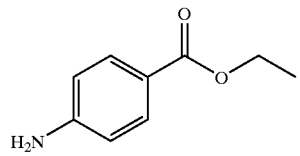

4-Aminobenzoic acid (5.0 g, 36.46 mmol) in 500 mL 3-neck round bottomed flask, fitted with a condenser, thermometer, addition funnel, stir bar, and nitrogen atmosphere, was dissolved in ethanol (100 mL). Next ethanol/HCl saturate (from bubbling concentrated HCl through ethanol) was added dropwise, by addition funnel. Then stirred at reflux for 1 h, cooled to room temperature, and stirred an additional 104 hours. Reaction mixture was then concentrated under reduced vacuum, and dissolved in ethyl acetate, and washed with water (2×50 mL), dried ($K_2CO_3$), filtered and concentrated under reduced vacuum, yielding 3.56 g of an off-white solid. This material was purified by silica gel chromatography, using a Waters HPLC Prep 2000, over one Prep-Pak, in a 1:1 hexanes:ethyl acetate solvent system, yielding the title compound as 2.35 g (39%) as a white solid.

Electrospray-MS 166.0 (M*+1).

PREPARATION 23

3-Amino-benzoic Acid Ethyl Ester

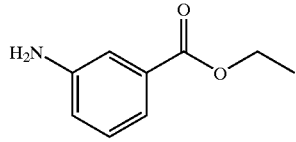

3-Aminobenzoic acid (5.0 g, 36.46 mmol) in 500 mL 3-neck round bottomed flask, fitted with a condenser, thermometer, addition funnel, stir bar, and nitrogen atmosphere, was dissolved in ethanol (100 mL). Next ethanol/HCl saturate (from bubbling concentrated HCl through ethanol) was added dropwise, by addition funnel. Then stirred at reflux for 1 h, cooled to room temperature, and stirred an additional 84 hours. Reaction mixture was then concentrated under reduced vacuum, and dissolved in ethyl acetate, and washed with water (2×50 mL), dried ($K_2CO_3$), filtered and concentrated under reduced vacuum, yielding 1.14 g of a brown oil. This material was purified by silica gel chromatography, using a Chromatotron® with a 6000 uM rotor, in a 1:1 hexanes:ethyl acetate solvent system, yielding the title compound as 1.24 g (21%) brown oil.

Electrospray-MS 166.0 (M*+1).

PREPARATION 24

Preparation of 4-tert-Butoxycarbonylamino-benzoic Acid Ethyl Ester

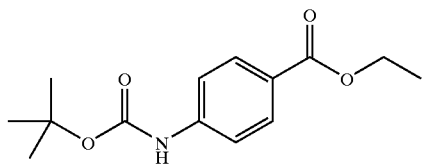

The amine prepared in preparation 22 (2.35 g, 14.23 mmol), di-tert-butyl dicarbonate (3.42 g, 15.65 mmol), and methylene chloride (100 mL) were combined into a 250 mL round bottomed flask, fitted with a stirbar, and under a nitrogen atmosphere, and stirred at room temperature for 15 minutes. Then added dimethylaminopyridine (610 mg, 0.35 mmol), and stirred for an additional hour. The reaction mixture was then quenched with water (100 mL), separated by separatory funnel, dried the organic layer ($MgSO_4$), filtered, and concentrated under reduced vacuum, yielding 3.66 g of a slow crystallizing yellow oil. This material was purified by silica gel chromatography, using a Waters HPLC Prep 2000 with one Prep-Pak, in a 1:1 hexanes:ethyl acetate solvent system, yielding the title compound as 1.3 g (34%) white crystals.

Electrospray-MS 266.0 (M*+1).

PREPARATION 25

3-tert-Butoxycarbonylamino-benzoic Acid Ethyl Ester

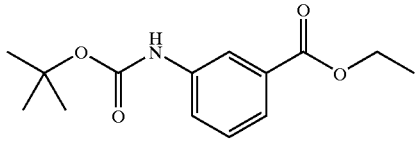

The amine prepared in preparation 23 (1.24 g, 7.51 mmol), di-tert-butyl dicarbonate (1.80 g, 8.26 mmol), and methylene chloride (50 mL) were combined into a 250 mL round bottomed flask, fitted with a stirbar, and under a nitrogen atmosphere, and stirred at room temperature for 15 minutes. Then added dimethylaminopyridine (610 mg, 0.35 mmol), and stirred for an additional hour. The reaction mixture was then quenched with water (100 mL), separated by separatory funnel, drying the organic layer ($MgSO_4$), filtered, and concentrated under reduced vacuum, yielding 2.06 g brown oil. This material was purified by silica gel chromatography, using a Waters HPLC Prep 2000 with one Prep-Pak, in a 1:1 hexanes:ethyl acetate solvent system, yielding the title compound as 750 mg (38%) brown oil.

Electrospray-MS 266.0 (M*+1).

PREPARATION 26

4-tert-Butoxycarbonylamino-benzoic Acid

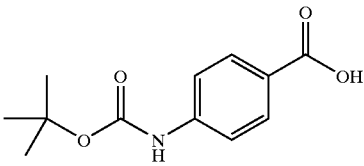

The ester prepared in preparation 24 (1.3 g, 4.90 mmol), lithium hydroxide (720 mg, 17.15 mmol), methanol (24.5 mL), water (24.5 mL), and tetrahydrofuran (73.5 mL), were combined in a 250 mL round bottomed flask, fitted with a stirbar, and under a nitrogen atmosphere. The mixture was stirred vigorously at room temperature for 16 hours, then concentrated under vacuum, dissolved in 1N HCl, and extracted with methylene chloride (100 mL×3). Organic layer was next dried ($MgSO_4$), filtered, and concentrated under vacuum, yielding 1.07 g of white solid. This material was purified by silica gel chromatography, using a Chromatotron® with a 6000 uM rotor, in a 1:1 hexanes:ethyl acetate solvent system, yielding the title compound as 440 mg (38%) white solid.

Electrospray-MS 238.0 (M*+1).

PREPARATION 27

3-tert-Butoxycarbonylamino-benzoic Acid

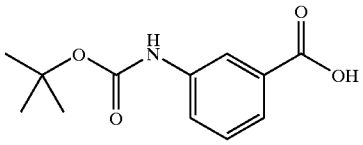

The ester prepared in preparation 25 (750 mg, 2.83 mmol), lithium hydroxide (415 mg, 9.89 mmol), methanol (15 mL), water (15 mL), and tetrahydrofuran (45 mL), were combined in a 250 mL round bottomed flask, fitted with a stirbar, and under a nitrogen atmosphere. The mixture was stirred vigorously at room temperature for 16 hours, then was concentrated under vacuum, dissolved in 1N HCl, and extracted with methylene chloride (100 mL×3). Organic layer was dried ($MgSO_4$), filtered, and concentrated under vacuum, yielding 600 mg of white solid. This material was purified by recrystallization in hexanes:ethyl acetate, yielding the title compound as 580 mg (86%) white solid.

Electrospray-MS 238.0 (M*+1).

PREPARATION 28

Enzymatic Resolution of (+,−)-2-(4-Bromophenyl)cyclopentanol

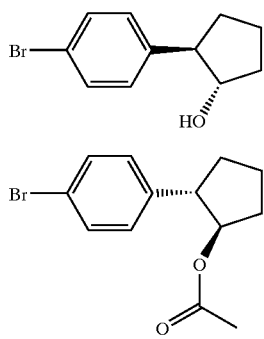

Scheme IC: A solution of (+,−)-2-(4-bromophenyl)cyclopentanol (250.5 g, 1.04 moles) in 250 ml MTBE is added to 16 grams immobilized *Candida antarctica* B lipase (Roche Molecular Biochemicals CHIRAZYME® L-2, c.-f. C2, lyo, >3200 units). With stirring, vinyl acetate (51.7 g, 0.60 mole) is added. This mixture is stirred under nitrogen at ambient temperature with periodic HPLC analysis (Zorbax SB-Phenyl, 250×46 mm, 35% 0.1% $H_3PO_4$:65% acetonitrile, 1.0 ml/min, λ=220 nm). Acylation is complete in 180 minutes. Immobilized enzyme is removed by gravity filtration, and the filtrate is evaporated in vacuo to provide 247.6 g (90.9%) of a 1:1 mixture of (1S,2R)-2-(4-bromophenyl)cyclopentanol (compound A) and (1R,2S)-1-acetoxy-2-(4-bromophenyl)cyclopentane (compound B).

Compound A; $^1$H NMR ($CDCl_3$) δ 1.19–1.25 (m, 2H), 1.68–1.71 (m, 1H), 1.72–1.80 (m, 1H), 1.98–2.06 (m, 3H), 2.95–2.99 (m, 1H), 4.24–4.26 (m, 1H), 7.16–7.18 (d, 2H, J=8.54 Hz), 7.44–7.46 (d, 2H, J=8.30 Hz); $^{13}$C NMR ($CDCl_3$) δ 22.56, 27.84, 34.25, 51.62, 75.81, 120.65, 128.70, 128.76, 128.95, 130.62, 131.72, 133.89, 134.05, 139.33.

Compound B; $^1$H NMR ($CDCl_3$) δ 1.61–1.70 (m, 2H), 1.71–1.81 (m, 2H), 1.82–1.84 (m, 2H), 2.03 (s, 3H), 2.11–2.21 (m, 2H), 3.08–3.11 (m, 1H), 5.05–5.08 (m, 1H), 7.08–7.12 (d, 2H, J=8.24 Hz), 7.39–7.42 (d, 2H, J=8.54 Hz); $^{13}$C NMR ($CDCl_3$) δ 21.35, 22.78, 31.95, 32.05, 50.59, 81.67, 120.07, 128.42, 128.93, 131.40, 131.92, 141.62, 170.65.

EXAMPLE 1

Preparation of (+,−) Trans-propane-2-sulfonic Acid (2-phenyl-cyclopentyl)-amide

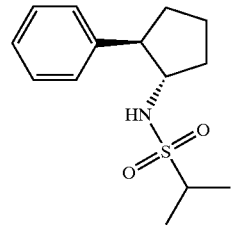

Scheme II, step A: (+,−) Trans-2-phenylcyclopentylamine (5.95 g, 37.0 mmol, preparation 3) was dissolved in dry methylene chloride and cooled to 0° C. under a nitrogen atmosphere. 6.1 mL (40.7 mmol) of DBU was added followed by dropwise addition of 2-propanesulfonyl chloride (4.6 mL, 40.7 mmol). The reaction was allowed to warm to room temperature and stirred overnight. The reaction was judged incomplete by TLC and an additional 20% of DBU and 2-propanesulfonyl chloride were added. Stirring at room temperature was continued for 3 days. The reaction was diluted with methylene chloride and washed (1×100 mL) with 1N HCl. The organic phase was dried over sodium sulfate, filtered and concentrated in vacuo to 9.3 g. The product was purified on silica by Chromatotron® eluting with 99:1 methylene chloride:ethyl acetate to yield 5.7 g (31%) of the title compound as a white solid. The NMR was consistent with the assigned structure.

Analysis calculated for $C_{14}H_{21}NO_2S$: % C, 62.88; % H, 7.92; % N, 5.24. Found: % C, 62.38; % H, 7.77; % N, 4.93. Mass Spectrum (ES MS): M−1=266. Exact Mass calculated for (M+$NH_4$) $C_{14}H_{25}N_2O_2S$=285.1637; found 285.1629.

EXAMPLE 2

Preparation of (+,−) Trans Propane-2-sulfonic Acid [2-(4-iodo-phenyl)-cyclopentyl]-amide

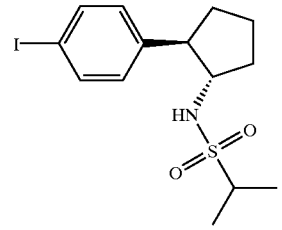

Scheme II, step B: (+,−) Trans-propane-2-sulfonic acid (2-phenyl-cyclopentyl)-amide (0.52 g, 1.47 mmol, prepared in example 1) was dissolved in 30 mL of glacial acetic acid. To this solution was added concentrated sulfuric acid (0.16 mL, 1.61 mmol) at room temperature followed by iodine (0.19 g, 0.74 mmol), and diiodine pentoxide (0.20 g, 0.59 mmol). The reaction was then protected from light and heated to 90° C. and stirred for 22 hours. To the dark brown reaction mixture was slowly added 10% aqueous sodium bisulfite. The mixture was cooled to 0° C. for 1 hour and a light brown solid collected by filtration. The solid was dissolved in warm diethyl ether and washed with water (2x), then saturated sodium bicarbonate (1x). The organic layer was separated, dried ($Na_2SO_4$), filtered and concentrated in vacuo to give 435 mg (75%) of the title compound. The NMR was consistent with the assigned structure.

Analysis calculated for $C_{14}H_{20}INO_2S$: % C, 42.76; % H, 5.13; % N, 3.56. Found: % C, 42.73; % H, 5.00; % N, 3.29. Mass Spectrum (ES MS): M−1=392. Exact Mass calculated for (M+$NH_4$) $C_{14}H_{24}IN_2O_2S$=411.0603; found 411.0611.

EXAMPLE 2A

Preparation of (1R,2S) Trans Propane-2-sulfonic Acid [2-(4-iodo-phenyl)-cyclopentyl]-amide

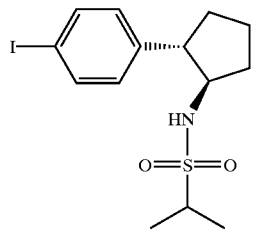

The racemic trans compound (400.0 mg) from example 2 was separated into individual enantiomers by chiral chromatography. The semiprep column used was 1x25 cm Chiralcel OD eluting with 90% Heptane/10% IPA containing 0.2% dimethylethylamine at a flow of 4.0 ml/min monitoring at a UV wavelength of 260 nm. The analytical column was 0.46x25 cm Chiralcel OD eluting with 90% Heptane/10% IPA containing 0.2% dimethylethylamine at a flow of 1.0 ml/min monitoring at a UV wavelength of 220 nm. The early eluting compound had a retention time of 9.32 min. The yield was 200 mg. Enantiomeric excess was estimated to be 99% by HPLC.

Mass Spectrum (ES MS): M−1=302.

EXAMPLE 2B

Preparation of (1S,2R) Trans Propane-2-sulfonic Acid [2-(4-iodo-phenyl)-cyclopentyl]-amide

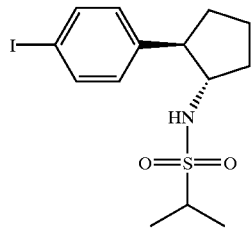

The racemic trans compound (400.0 mg) from example 2 was separated into individual enantiomers by chiral chromatography. The semiprep column used was 1x25 cm Chiralcel OD eluting with 90% Heptane/10% IPA containing 0.2% dimethylethylamine at a flow of 4.0 ml/min monitoring at a UV wavelength of 260 nm. The analytical column was 0.46x25 cm Chiralcel OD eluting with 90% Heptane/10% IPA containing 0.2% dimethylethylamine at a flow of 1.0 ml/min monitoring at a UV wavelength of 220 nm. The late eluting compound had a retention time of 12.28 min. The yield was 172 mg. Enantiomeric excess was estimated to be 98% by HPLC.

Mass Spectrum (ES MS): M−1=302.

EXAMPLE 3

Preparation of (+,−) Trans Propane-2-sulfonic Acid (2-biphenyl-4-yl-cyclopentyl)-amide

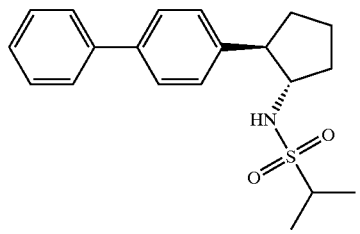

Scheme II, step C: (+,−) Trans propane-2-sulfonic acid [2-(4-iodo-phenyl)-cyclopentyl]-amide (58 mg, 0.15 mmol, prepared in example 2) and phenylboronic acid (22 mg, 0.18 mmol) were dissolved in 20 mL of n-propanol and 25 mg (0.18 mmol)of potassium carbonate in 5 mL of water added. A catalytic amount of palladium acetate is added (2 mg) and the mixture refluxed at 90° C. for 4 hours. The reaction is filtered, rinsed with ethyl acetate. The filtrate is diluted with ethyl acetate and washed with saturated sodium bicarbonate (3x30 mL) and brine (1x30 mL). The organic phase is dried over sodium sulfate, filtered and concentrated in vacuo to a crude solid which is purified by reverse phase chromatography (Vydac C18 column with a $CH_3CN$ gradient of 5→55% over 2 hours with a flow rate of 20 mL/min). The fractions were freeze-dried to give 34 mg (68%) of the title compound. The NMR was consistent with. the assigned structure.

Mass Spectrum (ES MS): M−1=342. Exact Mass calculated for (M+$NH_4$) $C_{20}H_{29}N_2O_2S$=361.1950; found 361.1962.

EXAMPLE 4

Preparation of (+,−) Trans Propane-2-sulfonic Acid [2-(4'-cyano-biphenyl-4-yl)-cyclopentyl]-amide

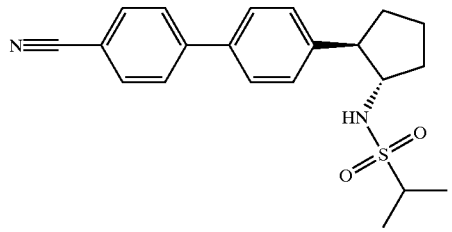

Scheme II, step C: (+,−) Trans propane-2-sulfonic acid [2-(4-iodo-phenyl)-cyclopentyl]-amide (375 mg, 0.95 mmol, prepared in example 2) and 4-cyanophenylboronic acid (168 mg, 1.14 mmol) were dissolved in 20 mL of n-propanol and 25 mg (0.18 mmol)of potassium carbonate in 5 mL of water added. A catalytic amount of palladium acetate is added (11 mg) and the mixture refluxed at 90° C. for 7 hours. The reaction is worked up as in preparation 6. The combined organics were dried ($Na_2SO_4$), filtered and concentrated in vacuo. Purification by silica chromatography using a Chromatotron® was achieved eluting with 99:1 methylene chloride:methanol to afford 307 mg (87%) of the title compound. The NMR was consistent with the assigned structure.

Mass Spectrum (ES MS): M−1=367. Exact Mass calculated for (M+NH$_4$) C$_{21}$H$_{28}$N$_3$O$_2$S=386.1902; found 386.1889.

EXAMPLE 5

Preparation of (+,−) Trans Propane-2-sulfonic acid {2-[4'-(2-methanesulfonylamino-ethyl)-biphenyl-4-yl]-cyclopentyl}-amide

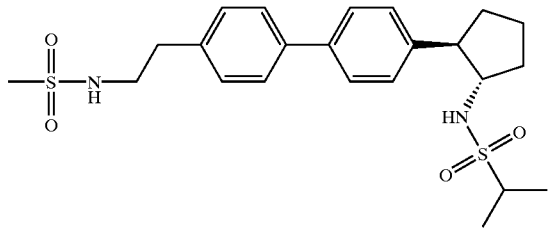

Scheme II, step C: (+,−) Trans propane-2-sulfonic acid [2-(4-iodo-phenyl)-cyclopentyl]-amide (300 mg, 0.76 mmol, prepared in example 2) and N-carbamic acid tert-butyl ester-N-methanesulfonamide-N-phenethyl-4-boronic acid (316 mg, 0.92 mmol) were dissolved in 20 mL of n-propanol and 25 mg (0.18 mmol) of potassium carbonate in 5 mL of water added. A catalytic amount of palladium acetate is added (9 mg) and the mixture refluxed at 90° C. for 4 hours. The reaction is worked up as in preparation 6. Dissolved the residue in methylene chloride and added 5 mL neat TFA and stirred overnight at room temperature. The TLC indicated the Boc protecting group had been removed and the reaction was concentrated in vacuo. Purification by silica chromatography using a Chromatotron® was achieved eluting with 95:5 methylene chloride:ethyl acetate to afford 225 mg (64%) of the title compound. The NMR was consistent with the assigned structure.

Mass Spectrum (ES MS): M−1=463. Analysis calculated for C$_{23}$H$_{32}$N$_2$O$_4$S$_2$: % C, 59.45; % H, 6.94; % N, 6.03. Found: % C, 59.44; % H, 6.84; % N, 6.29.

EXAMPLE 6

Preparation of (+,−) Trans Propane-2-sulfonic acid [2-(3'-methanesulfonylamino-biphenyl-4-yl)-cyclopentyl]-amide

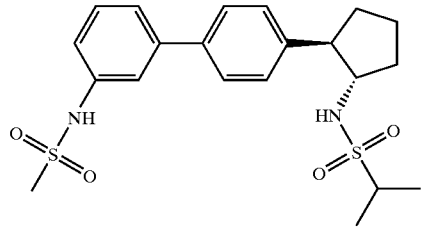

Scheme II, step C: (+,−) Trans propane-2-sulfonic acid [2-(4-iodo-phenyl)-cyclopentyl]-amide (235 mg, 0.60 mmol, prepared in example 2) and N-[3-(4,4,5,5-Tetramethyl-[1,3,2]dioxaborolan-2-yl)-phenyl]-methanesulfonamide (213 mg, 0.72 mmol) were dissolved in 25 mL of n-propanol and 25 mg (0.18 mmol) of potassium carbonate in 5 mL of water added. A catalytic amount of palladium acetate is added (7 mg) and the mixture refluxed at 90° C. for 4 hours. The reaction is worked up as in preparation 6. Purification by silica chromatography using a Chromatotron® was achieved eluting with 90:10 methylene chloride:ethyl acetate to afford 225 mg (86%) of the title compound as a white solid. The NMR was consistent with the assigned structure.

Mass Spectrum (ES MS): M−1=435. Exact Mass calculated for (M+NH$_4$) C$_{21}$H$_{32}$N$_3$O$_4$S$_2$=454.1834; found 454.1817.

EXAMPLE 6A

Preparation of (1R,2S) Trans Propane-2-sulfonic Acid [2-(3'-methanesulfonylamino-biphenyl-4-yl)-cyclopentyl]-amide

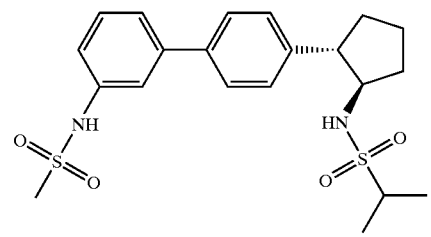

The racemic trans compound (145 mg) from example 6 was separated into individual enantiomers by chiral chromatography. The semiprep column used was 1×25 cm Chiralpak AD eluting with 30% Heptane/50% 3A alcohol/20% CO$_2$ at a flow of 5.0 ml/min, 35° C., 2000 psi, monitoring at a UV wavelength of 290 nm. The analytical column was 0.46×25 cm Chirose Cl eluting with 40% 3A alcohol/heptane at a flow of 1.0 ml/min monitoring at a UV wavelength of 230 nm. The early eluting compound had a retention time of 14.3 min. The yield was 43 mg. Enantiomeric excess was estimated to be 99% by HPLC.

Mass Spectrum (ES MS): M−1=435.

EXAMPLE 6B

Preparation of (1S,2R) Trans Propane-2-sulfonic Acid [2-(3'-methanesulfonylamino-biphenyl-4-yl)-cyclopentyl]-amide

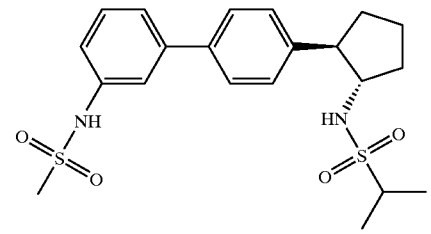

The racemic trans compound (145 mg) from example 6 was separated into individual enantiomers by chiral chromatography. The semiprep column used was 1×25 cm Chiralpak AD eluting with 30% Heptane/50% 3A alcohol/20% CO$_2$ at a flow of 5.0 ml/min, 35° C., 2000 psi, monitoring at a UV wavelength of 290 nm. The analytical column was 0.46×25 cm Chirose Cl eluting with 40% 3A alcohol/heptane at a flow of 1.0 ml/min monitoring at a UV

43 wavelength of 230 nm. The late eluting compound had a retention time of 15.5 min. The yield was 46 mg. Enantiomeric excess was estimated to be 99% by HPLC.

Mass Spectrum (ES MS): M−1=435.

EXAMPLE 7

Preparation of (+,−) Trans Propane-2-sulfonic Acid [2-(2',4'-difluoro-biphenyl-4-yl)-cyclopentyl]-amide

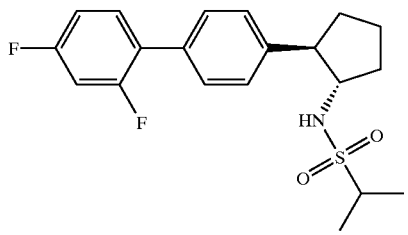

Scheme II, step C: (+,−) Trans propane-2-sulfonic acid [2-(4-iodo-phenyl)-cyclopentyl]-amide (120 mg, 0.31 mmol, prepared in example 2) and 2,4-difluorophenylboronic acid (60 mg, 0.38 mmol) were treated as described in example 6 to afford 103 mg (89%) of the title compound as a white solid. The NMR was consistent with the assigned structure.

Mass Spectrum (ES MS): M−1=378. Exact Mass calculated for (M+NH$_4$) C$_{20}$H$_{27}$F$_2$N$_2$O$_2$S=397.1761; found 397.1753.

EXAMPLE 7A

Preparation of (1R,2S) Trans Propane-2-sulfonic Acid [2-(2',4'-difluoro-biphenyl-4-yl)-cyclopentyl]-amide

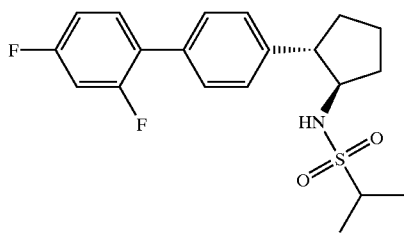

The racemic trans compound (230 mg) from example 7 was separated into individual enantiomers by chiral chromatography. The semiprep column used was 1×25 cm Chiralcel AD eluting with a gradient of 5%-50% IPA/Heptane over 30 min at a flow of 5.0 ml/min monitoring at a uv wavelength of 260 nm. The analytical column was 0.46×25 cm Chiralcel AD eluting with a gradient of 5%–50% IPA/Heptane over 30 min at a flow of 1.0 ml/min monitoring at a uv wavelength of 220 nm. The early eluting compound had a retention time of 10.5 min. The yield was 85 mg. Enantiomeric excess was estimated to be 98% by HPLC.

Mass Spectrum (ES MS): M−1=378.

44

EXAMPLE 7B

Preparation of (1S,2R) Trans Propane-2-sulfonic Acid (2-(2',4'-difluoro-biphenyl-4-yl)-cyclopentyl]-amide

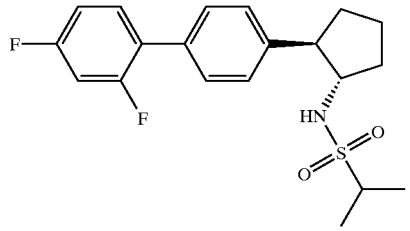

The racemic trans compound (230 mg) from example 7 was separated into individual enantiomers by chiral chromatography. The semiprep column used was 1×25 cm Chiralcel AD eluting with a gradient of 5%–50% IPA/Heptane over 30 min at a flow of 5.0 ml/min monitoring at a uv wavelength of 260 nm. The analytical column was 0.46×25 cm Chiralcel AD eluting with a gradient of 5%–50% IPA/Heptane over 30 min at a flow of 1.0 ml/min monitoring at a uv wavelength of 220 nm. The late eluting compound had a retention time of 12.9 min. The yield was 103 mg. Enantiomeric excess was estimated to be 91% by HPLC.

Mass Spectrum (ES MS): M−1=378.

EXAMPLE 8

Preparation of (+,−) Trans Propane-2-sulfonic Acid [2-(4'-cyanomethyl-biphenyl-4-yl)-cyclopentyl]-amide

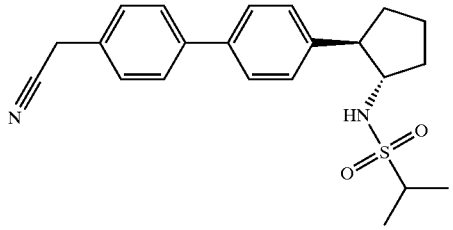

Scheme II, step C: (+,−) Trans propane-2-sulfonic acid [2-(4-iodo-phenyl)-cyclopentyl]-amide (356 mg, 0.91 mmol, prepared in example 2) and [4-(4,4,5,5-Tetramethyl-[1,3,2]dioxaborolan-2-yl)-phenyl]-acetonitrile (275 mg, 1.13 mmol) were treated as described in example 6. The product was chromatographed on Chromatotron® eluting with 99.5:0.5 methylene chloride:ethyl acetate to afford 237 mg (68%) of the title compound as a white solid. The NMR was consistent with the assigned structure.

Mass Spectrum (ES MS): M−1=381.

EXAMPLE 9

Preparation of (+,−) Trans Propane-2-sulfonic Acid {2-[4'-(2-amino-ethyl)-biphenyl-4-yl]-cyclopentyl}-amide

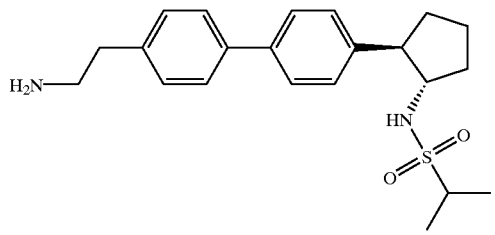

Scheme III, step A: (+,−) Trans propane-2-sulfonic acid [2-(4'-cyanomethyl-biphenyl-4-yl)-cyclopentyl]-amide (210 mg, 0.55 mmol, prepared in example 8) was dissolved in 20 mL dry THF. To this solution was added 0.83 mL (1.65 mmol) of a 2.0 M solution of borane dimethyl sulfide in THF. The reaction was heated to reflux for 4 hours then concentrated in vacuo. To this solid was added 30 mL of diethyl ether, 15 mL of concentrated HCl, 10 mL of water, and 5 mL of methanol and stirred at room temperature for 30 minutes. The aqueous layer was separated, and the organic phase washed 1× with water. The combined aqueous phases were made basic with sodium hydroxide at 0° C. and extracted into diethyl ether (2×50 mL) followed by ethyl acetate (1×50 mL). The combined organic phases were dried over sodium sulfate, filtered, and concentrated to a crude oil which was used without further purification.

Mass Spectrum (ES MS): M−1=385.

EXAMPLE 10

Preparation of (+,−) Trans N-(2-{4'-[2-(Propane-2-sulfonylamino)-cyclopentyl]-biphenyl-4-yl}-ethyl)-acetamide

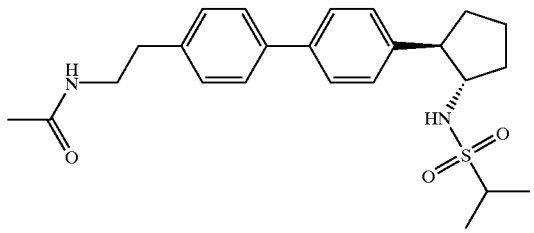

Scheme III, step B: (+,−) Trans propane-2-sulfonic acid {2-[4'-(2-amino-ethyl)-biphenyl-4-yl]-cyclopentyl}-amide (prepared in example 9) was dissolved in 20 mL of dry methylene chloride and triethylamine added (0.275 mL, 1.98 mmol). To this stirred mixture was added acetyl chloride (0.084 mL, 1.19 mmol). The reaction was stirred at room temperature for 3 days. The reaction was concentrated in vacuo and chromatographed on a Chromatotron® eluting with 98:2 methylene chloride:methanol which afforded 150 mg (64% 2 steps) of the title compound. The NMR was consistent with the assigned structure.

Mass Spectrum (ES MS): M−1=427. Exact Mass calculated for (M+NH$_4$) C$_{24}$H$_{36}$N$_3$O$_3$S=446.2477; found 446.2477.

EXAMPLE 11

Preparation of (+,−) Trans 2,2,2-Trifluoro-N-(2-{4'-[2-(propane-2-sulfonylamino)-cyclopentyl]-biphenyl-4-yl}-ethyl)-acetamide

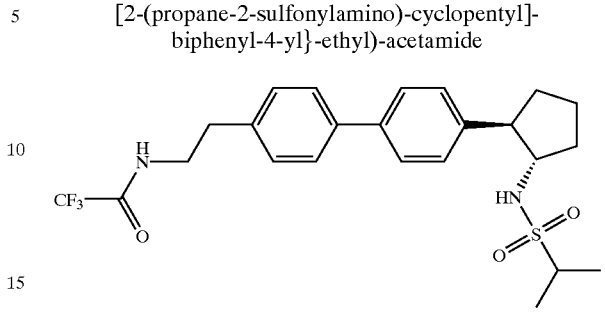

Scheme III, step B: (+,−) Trans propane-2-sulfonic acid [2-(4-iodo-phenyl)-cyclopentyl]-amide (100 mg, 0.25 mmol, prepared in example 2) and 2,2,2-Trifluoro-N-{2-[4-(4,4,5,5-tetramethyl-[1,3,2]dioxaborolan-2-yl)-phenyl]-ethyl}-acetamide (105 mg, 0.31 mmol) were treated as described in example 6. The reaction was purified by radial chromatography eluting with 70:30 hexanes:ethyl acetate to afford 48 mg (39%) of the title compound as a white solid. The NMR was consistent with the assigned structure.

Mass Spectrum (ES MS): M−1=481. Exact Mass calculated for (M+NH$_4$) C$_{24}$H$_{33}$F$_3$N$_3$O$_3$S=500.2195; found 500.2183.

EXAMPLE 12

Preparation of (1R,2S)-Trans Propane-2-sulfonic Acid (2-phenyl-cyclopentyl)-amide

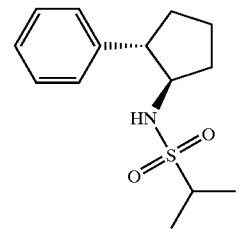

The racemic trans compound from example 1 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The early eluting compound had a retention time of 6.82 min. Enantiomeric excess was estimated to be 99% by HPLC.

Mass Spectrum (ES MS): M−1=266. Analysis calculated for C$_{14}$H$_{21}$NO$_2$S: % C, 62.89; % H, 7.92; % N, 5.24. Found: % C, 62.46; % H, 7.81; % N, 5.18.

EXAMPLE 13

Preparation of (1S,2R)-Trans Propane-2-sulfonic Acid (2-phenyl-cyclopentyl)-amide

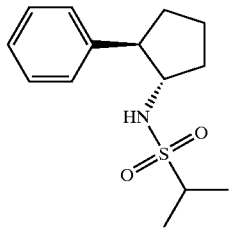

The racemic trans compound from example 1 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The later eluting compound had a retention time of 8.97 min. Enantiomeric excess was estimated to be 99% by HPLC.

Mass Spectrum (ES MS): M−1=266. Analysis calculated for $C_{14}H_{21}NO_2S$: % C, 62.89; % H, 7.92; % N, 5.24. Found: % C, 62.95; % H, 7.71; % N, 5.18.

EXAMPLE 14

Preparation of (1R,2S)-Trans Propane-2-sulfonic Acid [2-(4'-cyano-biphenyl-4-yl)-cyclopentyl]-amide

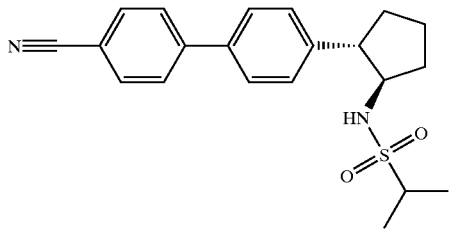

The racemic trans compound from example 4 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The early eluting compound had a retention time of 12.64 min. Enantiomeric excess was estimated to be 88% by HPLC.

Exact Mass calculated for (M+NH$_4$) $C_{21}H_{28}N_3O_2S$= 386.1902; found 386.1878; Mass Spectrum (ES MS): M−1= 367.

EXAMPLE 15

Preparation of (1S,2R)-Trans Propane-2-sulfonic Acid [2-(4'-cyano-biphenyl-4-yl)-cyclopentyl]-amide

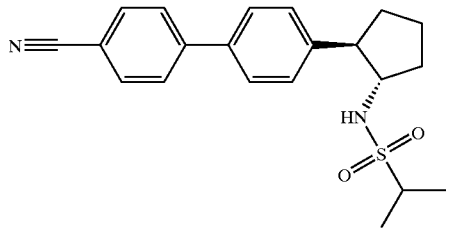

The racemic trans compound from example 4 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The later eluting compound had a retention time of 14.89 min. Enantiomeric excess was estimated to be 88% by HPLC.

Exact Mass calculated for (M+NH$_4$) $C_{21}H_{28}N_3O_2S$= 386.1902; found 386.1915; Mass Spectrum (ES MS): M−1= 367.

EXAMPLE 16

Preparation of (+,−) Cis-propane-2-sulfonic Acid (2-phenyl-cyclopentyl)-amide

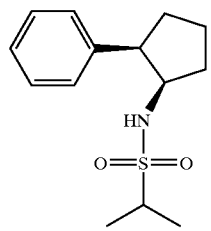

Scheme II, step A: (+,−) Cis-2-Phenyl-cyclopentylamine (0.43 g, 2.7 mmol, from preparations 5 or 7) was dissolved in 15 mL of methylene chloride and cooled to 0° C. under nitrogen. 0.52 mL (3.5 mmol) of DBU was added followed by 0.39 mL (3.5 mmol) of isopropylsulfonyl chloride. Stirring was allowed to continue for 3 days while warming to room temperature. The reaction was washed with 1N HCl and the organic phase dried over sodium sulfate. Filtered, and concentrated in vacuo to a crude brown solid which was a 4:1 mixture of cis:trans by NMR. The isomers were purified by radial chromatography eluting with methylene chloride. 195 mg (27%) of the title compound (cis isomer) was isolated as a white solid as well as 15 mg of the more polar trans isomer. The NMR was consistent with the assigned structure.

Analysis calculated for $C_{14}H_{21}NO_2S$: % C, 62.89; % H, 7.92; % N, 5.24. Found: % C, 62.74; % H, 7.70; % N, 5.30. Mass Spectrum (ES MS): M−1=266.

Alternative Synthesis of (+,−) Cis-propane-2-sulfonic Acid (2-phenyl-cyclopentyl)-amide Scheme II, step A: A 250 mL three necked round bottom flask equipped with a magnetic stirrer is charged with the amine (8.72 g, 54.16 mmol, prepared in preparation 8), methylene chloride (80.0 mL), triethylamine (14.79 mL, 106.15 mmol) and dimethylaminopyridine (0.33 g, 2.71 mmol) with stirring. Reaction solution was then cooled to 0° C. (ice/water bath), then added dropwise isopropylsulfonyl chloride (5.96 mL, 53.07 mmol) dissolved in methylene chloride (20.0 mL) over a period of 30.0 minutes. Reaction was then stirred at 0° C. for 60.0 minutes and brought to room temperature. Stirred for 1.5 hours and quenched with 1N HCl (150.0 mL). Separated lower organic layer and back extracted aqueous layer with methylene chloride (50.0 mL). The combined organic layer was then dried with anhydrous magnesium sulfate, filtered and concentrated to a tan solid (mass=9.06 g);

$^1$H nmr (CDCl$_3$) δ 0.9–1.0 (d, 3H), 1.1–1.2 (d, 3H), 1.7–2.15 (m, 6H), 2.8–2.95 (m, 1H) 2.25–3.2 (m, 1H), 3.6–3.75 (m, 1H), 3.9–4.0 (m, 1H); $^{13}$C (CDCl$_3$) δ 16.56, 21.79, 28.62, 33.76, 48.70, 53.78, 59.10, 127.23, 128.81, 128.90, 140.28).

EXAMPLE 17

Preparation of (+,−) Cis Propane-2-sulfonic Acid [2-(4-iodo-phenyl)-cyclopentyl]-amide

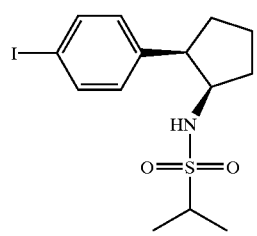

Scheme II, step B: (+,−) Cis-propane-2-sulfonic acid (2-phenyl-cyclopentyl)-amide (1.8 g, 6.7 mmol, prepared in example 16) was dissolved in 20 mL of glacial acetic acid and 0.7 mL (7.1 mmol) of concentrated sulfuric acid added followed by 2 mL of water. To this solution was added periodic acid (0.35 g, 1.6 mmol) and iodine (0.77 g, 3.0 mmol). The resulting mixture was heated to 60° C. for 3 hours. The reaction was cooled to room temperature and 20 mL of a 10% aqueous solution of sodium bisulfite was added. The product was extracted into ethyl acetate then washed with water, dilute sodium bicarbonate, and dried over magnesium sulfate. Filtered and concentrated in vacuo to 2.2 g of crude yellow oil. This oil was purified by reverse phase chromatography to give 341 mg (13%) of the title compound as a white solid. The NMR was consistent with the assigned structure.

Analysis calculated for C$_{14}$H$_{20}$INO$_2$S: % C, 42.76; % H, 5.13; % N, 3.56. Found: % C, 43.23; % H, 5.05; % N, 3.61. Mass Spectrum (ES MS): M−1=392.

EXAMPLE 17A

Preparation of (1S,2S) Cis Propane-2-sulfonic Acid [2-(4-iodo-phenyl)-cyclopentyl]-amide

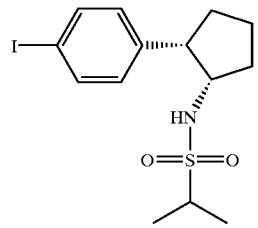

The racemic cis compound from example 17 was separated into individual enantiomers by chiral chromatography. The prep column used was 8×28 cm Chiralcel AD eluting with 100% 3A alcohol at a flow of 300.0 mL/min monitoring at a UV wavelength of 275 nm. The analytical column was 0.46×25 cm Chiralcel AD eluting with 100% 3A alcohol at a flow of 1.0 mL/min monitoring at uv of 220 nm. The early eluting compound had a retention time of 4.69 min. Enantiomeric excess was estimated to be 99% by HPLC.

Mass Spectrum (ES MS): M−1=392.

EXAMPLE 17B

Preparation of (1R,2R) Cis Propane-2-sulfonic Acid [2-(4-iodo-phenyl)-cyclopentyl]-amide

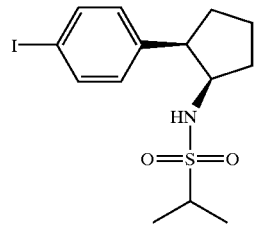

The racemic cis compound from example 17 was separated into individual enantiomers by chiral chromatography. The prep column used was 8×28 cm Chiralcel AD eluting with 100% 3A alcohol at a flow of 300.0 mL/min monitoring at a UV wavelength of 275 nm. The analytical column was 0.46×25 cm Chiralcel AD eluting with 100% 3A alcohol at a flow of 1.0 mL/min monitoring at uv of 220 nm. The late eluting compound had a retention time of 5.91 min. Enantiomeric excess was estimated to be 99% by HPLC.

Mass Spectrum (ES MS): M−1=392.

EXAMPLE 18

(+,−) Cis Propane-2-sulfonic Acid [2-(4'-cyano-biphenyl-4-yl)-cyclopentyl]-amide

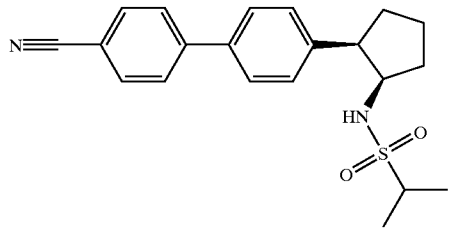

Scheme II, step C: (+,−) Cis propane-2-sulfonic acid [2-(4-iodo-phenyl)-cyclopentyl]-amide (150 mg, 0.38 mmol, prepared in example 17) was treated with 4-cyanophenyl boronic acid (56 mg, 0.38 mmol), palladium tetrakis triphenylphosphine (22 mg, 0.02 mmol) and cesium carbonate (150 mg, 0.46) under nitrogen in 10 mL of degassed dioxane. The reaction was heated to 85° C. and stirred overnight. The reaction was concentrated in vacuo and purified by radial chromatography eluting with 30:70 ethyl acetate:hexanes to give 12 mg (9%) of the title compound as a white solid. The NMR was consistent with the assigned structure.

Mass Spectrum (ES MS): M−1=367.

EXAMPLE 18A (1R,2R) Cis Propane-2-sulfonic Acid [2-(4'-cyano-biphenyl-4-yl)-cyclopentyl]-amide

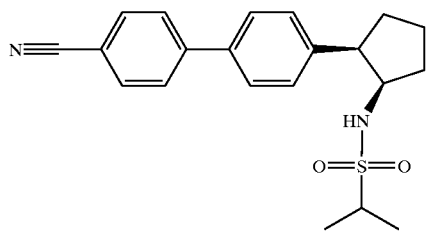

The Suzuki coupling of the chiral compound from example 17B (225 mg, 0.57 mmol) and 4-cyanophenylboronic acid (101 mg, 0.69 mmol) was accomplished in a manner analogous to that described in example 27. The reaction was worked up in a manner analogous to example 3. Purification by silica chromatography using a chromatotron was achieved eluting with 0.3% methanol/methylene chloride to afford 186 mg (88%) of the title compound as a white solid when concentrated from ether. The nmr was consistent with the assigned structure.

Mass Spectrum (ES MS): M−1=367. Analysis calculated for $C_{21}H_{24}N_2O_2S \times 0.5\ H_2O$: % C, 66.82; % H, 6.67; % N, 7.42. Found: % C, 66.54; % H, 6.29; % N, 7.31.

EXAMPLE 19

Preparation of (+,−) Cis Propane-2-sulfonic Acid {2-[4'-(2-methanesulfonylamino-ethyl)-biphenyl-4-yl]-cyclopentyl}-amide

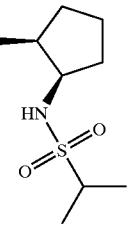

Scheme II, step C: (+,−) Cis propane-2-sulfonic acid [2-(4-iodo-phenyl)-cyclopentyl]-amide (134 mg, 0.34 mmol, prepared in example 17 was treated as described for the trans isomer in example 5. The product was purified by radial chromatography eluting first with methylene chloride then ethyl acetate was added (→20%) until all bands were removed to give 83 mg (53%) of the title compound as a white solid. The NMR was consistent with the assigned structure. Analysis calculated for $C_{23}H_{32}N_2O_4S_2 \ast 0.4\ CH_2Cl_2$: % C, 56.37; % H, 6.63; % N, 5.62. Found: % C, 56.76; % H, 6.26; % N, 5.71. Mass Spectrum (ES MS): M−1=463.

EXAMPLE 20

Preparation of (S,S)-Propane-2-sulfonic acid (2-phenyl-cyclopentyl)-amide

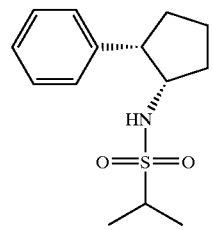

The racemic cis compound from example 16 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The early eluting compound had a retention time of 7.03 min. Enantiomeric excess was estimated to be 99% by HPLC.

Mass Spectrum (ES MS): M−1=266. Analysis calculated for $C_{14}H_{21}NO_2S$: % C, 62.89; % H, 7.92; % N, 5.24. Found: % C, 62.98; % H, 7.94; % N, 5.24.

EXAMPLE 21

Preparation of (R,R)-Propane-2-sulfonic acid (2-phenyl-cyclopentyl)-amide

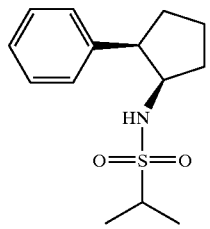

The racemic cis compound from example 16 was separated into individual enantiomers by chiral chromatography. The semiprep column used was 1×25 cm Chiralcel OD eluting with 10% IPA in heptane containing 0.2% dimethylethylamine at a flow of 4.0 mL/min monitoring at uv of 250 nm. The analytical column was 0.46×25 cm Chiralcel OD eluting with 10% IPA in heptane containing 0.2% dimethylethylamine at a flow of 1.0 mL/min monitoring at uv of 250 nm. The later eluting compound had a retention time of 7.84 min. Enantiomeric excess was estimated to be 98% by HPLC.

Mass Spectrum (ES MS): M−1=266. Analysis calculated for $C_{14}H_{21}NO_2S$: % C, 62.89; % H, 7.92; % N, 5.24. Found: % C, 63.23; % H, 7.93; % N, 5.23.

EXAMPLE 22

Preparation of (+,−) Cis Propane-2-sulfonic Acid [2-(4-nitro-phenyl)-cyclopentyl]-amide

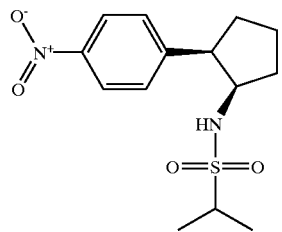

Scheme IV, step A: (+,−) Cis-propane-2-sulfonic acid (2-phenyl-cyclopentyl)-amide (560 mg, 2.1 mmol, prepared in example 16) was dissolved in 10 mL of trifluoroacetic acid and 534 mg (6.3 mmol) of sodium nitrate was added. The reaction was stirred 5 hours at room temperature. The reaction was diluted with methylene chloride and washed with water and dilute sodium bicarbonate. The organic layer was dried over sodium sulfate and concentrated in vacuo to 620 mg of a crude yellow oil. This oil was purified by radial chromatography eluting with 98:2 methylene chloride:ethyl acetate to give 120 mg (18%) of the title compound as a white solid and also 400 mg (62%) which contained a small amount of ortho nitrated product. The NMR was consistent with the assigned structure.

Analysis calculated for $C_{14}H_{20}N_2O_4S$: % C, 53.83; % H, 6.45; % N, 8.97. Found: % C, 53.58; % H, 6.36; % N, 8.78. Mass Spectrum (ES MS): M−1=311.

EXAMPLE 23

Preparation of (+,−) Cis Propane-2-sulfonic Acid [2-(4-amino-phenyl)-cyclopentyl]-amide

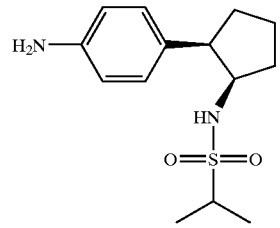

Scheme IV, step B: (+,−) Cis propane-2-sulfonic acid [2-(4-nitro-phenyl)-cyclopentyl]-amide (200 mg, 0.64 mmol, prepared in example 22) was dissolved in 25 mL of ethanol and hydrogenated over 25 mg of 5% Pd/C at room temperature overnight at 413.69 kPa (60 psi). The solution was filtered through celite and concentrated in vacuo to 142 mg (78%) of a colorless oil which was used directly.

Mass Spectrum (ES MS): M−1=281.

EXAMPLE 24

Preparation of (+,−) Cis N-{4-[2-(Propane-2-sulfonylamino)-cyclopentyl]-phenyl}-benzamide

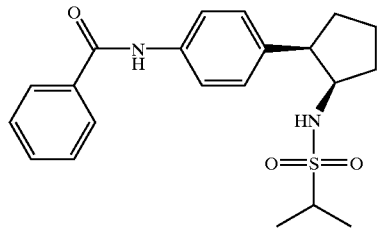

Scheme IV, step C: (+,−) Cis propane-2-sulfonic acid [2-(4-amino-phenyl)-cyclopentyl]-amide (265 mg, 0.94 mmol, prepared in example 23) was dissolved in 10 mL of methylene chloride and cooled to 0° C. under nitrogen. Benzoyl chloride was added (120 uL, 1.03 mmol) and after stirring 15 min the ice bath was removed and stirring continued for 2 hours. The reaction was diluted with methylene chloride and washed with water, then 0.1 N HCl and dried over sodium sulfate. The organic phase was concentrated in vacuo to 360 mg crude oil. The product was purified by radial chromatography eluting first with 70:30 methylene chloride:hexanes then ethyl acetate was added (→20%) until all bands were removed to give 120 mg (33%) of the title compound as a white solid. The NMR was consistent with the assigned structure.

Analysis calculated for $C_{21}H_{26}N_2O_3S$: % C, 65.26; % H, 6.78; % N, 7.25. Found: % C, 64.78; % H, 6.65; % N, 7.05. Mass Spectrum (ES MS): M+1=387.

EXAMPLE 25

Preparation of (+,−) Cis Propane-2-sulfonic Acid [2-(4-methanesulfonylamino-phenyl)-cyclopentyl]-amide

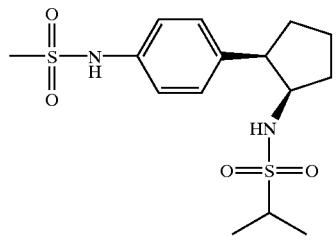

Scheme IV, step D: (+,−) Cis propane-2-sulfonic acid [2-(4-amino-phenyl)-cyclopentyl]-amide (73 mg, 0.26 mmol, prepared in example 23) was dissolved in 10 mL of methylene chloride and cooled to 0° C. under nitrogen. Triethylamine was added (40 uL, 0.28 mmol) followed by methanesulfonyl chloride (22 uL, 0.28 mmol) and after stirring 15 min the ice bath was removed and stirring continued. After 4 hours an additional 10 uL of methanesulfonyl chloride was added and stirring continued overnight. The reaction was concentrated in vacuo and purified by radial chromatography eluting with 99:1 methylene chloride:methanol and slowly increasing the percentage of methanol. The appropriate fractions were dried to 25 mg (27%) of the title compound as an off-white solid. The NMR was consistent with the assigned structure.

Mass Spectrum (ES MS): M−1=359.

EXAMPLE 26

Preparation of (+,−) Cis Propane-2-sulfonic Acid [2-(4-tert-butyl-phenyl)-cyclopentyl]-amide and (+,−) Trans Propane-2-sulfonic Acid [2-(4-tert-butyl-phenyl)-cyclopentyl]-amide

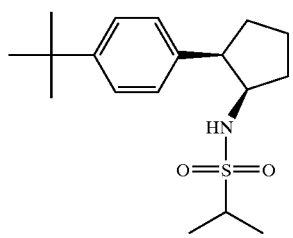

Cis

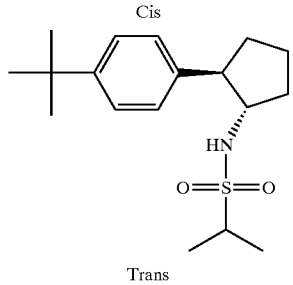

Trans

Preparation of Intermediate (+,−) Trans-2-(4-tert-Butyl-phenyl)-cyclopentanol

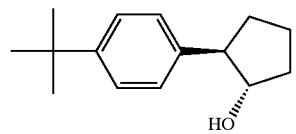

A 1000 mL round bottom flask equipped with addition funnel and reflux condenser containing $Et_2O$ (160 mL) maintained under an atmosphere of argon was charged with small pieces of lithium wire (3.52 g, 0.507 g atom). A solution of 4-t-butylbromobenzene (50.00 g, 0.235 mol) in $Et_2O$ (50 mL) was added dropwise such that a gentle reflux was maintained. The mixture was allowed to stir for 2 h before addition of 1,2-cyclopentene oxide (9.88 g, 0.117 mol). The mixture was stirred at room temperature for approximately 4 h, then stored in the freezer overnight before quenching with 1N HCl, and extracting with $Et_2O$. The $Et_2O$ extracts were washed with $H_2O$ and brine, dried over $Na_2SO_4$, filtered, and evaporated to give 34.5 g of crude. An analytical sample was recrystallized from petroleum ether to yield white crystals: mp 67–69. . . .

Calcd for $C_{15}H_{22}O$: C, 82.52; H, 10.16. Found: C, 82.70; H, 10.29.

Preparation of Intermediate 2-(4-tert-Butyl-phenyl)-cyclopentanone

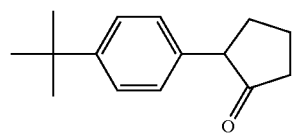

Scheme IB, step D: The alcohol (14.59 g, 66.8 mmol) was added dropwise in $CH_2Cl_2$ (100 mL) to a suspension of pyridinium chlorochromate (28.81 g, 134 mmol) in $CH_2Cl_2$ (300 mL.) The mixture was stirred at room temperature under $N_2$ for 48 h. $Et_2O$ (500 mL) was added, and the reaction mixture filtered through a pad of silica before concentrating in vacuo to give 9.60 g of a yellow oil. Flash chromatography on silica was conducted using 10% EtOAc/hexanes as eluent. Obtained 5.0 g (35%) of a clear oil.

Calcd. for $C_{15}H_{20}O$: C, 83.29; H, 9.32. Found: C, 83.24; H, 9.07.

Preparation of Intermediate 2-(4-tert-Butyl-phenyl)-cyclopentanone Oxime

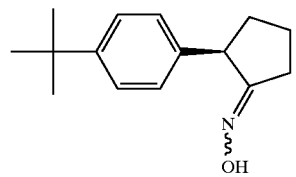

Scheme IA, step A: The ketone (5.30 g, 24.5 mmol) was dissolved in abs EtOH (100 mL) and treated with NaOH (1.96 g, 49.0 mmol) in $H_2O$ (15 mL) followed by hydroxylamine hydrochloride (2.55 g, 36.7 mmol.) The mixture was allowed to stir at 23 . . . for 5 h. The resultant thick precipitate was diluted with $H_2O$, and collected by filtration to afford 5.5 g (97%) of white crystals after air-drying. An analytical sample was prepared by recrystallization from hexanes: mp 127–130. . . .

Calcd. for $C_{15}H_{21}NO$: C, 77.88; H, 9.15; N, 6.05; Found: C, 78.18; H, 9.13; N, 5.96.

Preparation of Intermediate 2-(4-tert-Butyl-phenyl)-cyclopentylamine.

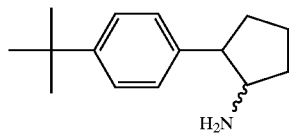

Scheme IA, step B: The oxime (0.40 g, 1.7 mmol) was placed on a Parr shaker at 241.32 kPa (35 psi) $H_2$ over $PtO_2$ (60 mg) for 42 h. The mixture was filtered through Celite® to remove catalyst and concentrated in vacuo. The resulting oil was taken up in $H_2O$ and washed with $Et_2O$ before making the aqueous solution basic pH with 2N NaOH and extracting with EtOAc. The EtOAc extracts were washed with brine, dried over $Na_2SO_4$, and evaporated to give 0.36 g (97%) of a clear oil which was used as the cis/trans mixture.

Preparation of Final Title Compound.

Scheme II, step A: The mixture of cis and trans amines (0.30 g, 1.4 mmol) prepared above were dissolved in $CH_2Cl_2$ (10 mL), cooled in an ice water bath, and treated with 1,8-diazobicyclo[5.4.0]undec-7-ene (0.23 mL, 1.5 mmol) and isopropylsulfonylchloride (0.17 mL, 1.5 mmol). The mixture was stirred under $N_2$ for 18 h. Additional DBU (0.23 mL, 1.5 mmol) and isopropylsulfonylchloride (0.17 mL, 1.5 mmol) were added, and the mixture stirred for 24 h longer before pouring onto $H_2O$ and extracting with $CH_2Cl_2$. The organic extracts were washed with 1N HCl, 10% $Na_2CO_3$, $H_2O$, and brine before drying over $Na_2SO_4$, and concentrating in vacuo to afford 0.20 g of a yellow oil. Flash chromatography on silica eluting with 10% EtOAc/hexanes was carried out to allow separation of the isomers. Obtained 30 mg (7%) of the cis isomer as a white solid (faster eluting component.) Obtained 15 mg (3%) of the trans isomer as an oil (slower eluting component.)

Cis isomer: $^1$H-NMR ... ($CDCl_3$) 0.98 (d, 3H), 1.19 (d, 3H), 1.38 (s, 9H), 1.70–2.15 (m, 6H), 2.85 (m, 1H), 3.30 (q, 1H), 3.59 (d, 1H, NH), 3.94 (m, 1H), 7.16 (d, 2H), 7.36 (d, 2H). Trans isomer: $^1$H-NMR ... ($CDCl_3$) 0.87 (d, 3H), 1.13 (d, 3H), 1.30 (s, 9H), 1.62 (m, 1H), 1.70–1.90 (m, 2H), 2.04–2.17 (m, 2H), 2.35 (m, 1H), 2.54 (m, 1H), 2.71 (m, 1H), 3.66 (m, 1H), 3.95 (d, 1H, NH), 7.18 (d, 2H), 7.34 (d, 2H).

EXAMPLE 27

Preparation of (+,-) Cis Propane-2-sulfonic Acid [2-(3'-methanesulfonylamino-biphenyl-4-yl)-cyclopentyl]-amide

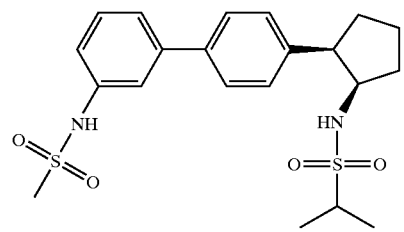

Scheme II, step C: (+,-) Cis propane-2-sulfonic acid [2-(4-iodo-phenyl)-cyclopentyl]-amide (185 mg, 0.47 mmol, prepared in example 17) and N-[3-(4,4,5,5-Tetramethyl-[1,3,2]dioxaborolan-2-yl)-phenyl]-methanesulfonamide (168 mg, 0.56 mmol) were dissolved in 25 mL of n-propanol and 78 mg (0.56 mmol) of potassium carbonate in 5 mL of water added. A catalytic amount of palladium acetate is added (5 mg) and the mixture refluxed at 90° C. for 4 hours. The reaction is worked up in a manner analogous to example 3. Purification by silica chromatography using a Chromatotron® was achieved eluting with 99:1 methylene chloride:methanol to afford 135 mg (66%) of the title compound as a white solid. The NMR was consistent with the assigned structure.

Mass Spectrum (ES MS): M-1=435. Analysis calculated for $C_{21}H_{28}N_2O_4S_2 \times 0.3\ H_2O$: % C, 57.07; % H, 6.52; % N, 6.34. Found: % C, 57.20; % H, 6.07; % N, 6.32.

EXAMPLE 28

Preparation of (+,-) Cis-propane-2-sulfonic Acid (2-p-tolyl-cyclopentyl)-amide

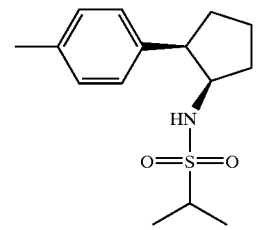

Scheme II, step A: A 100 mL round bottom flask equipped with a magnetic stirrer is charged with (+,-) cis-2-p-tolyl-cyclopentylamine (313 mg, 1.79 mmol, from preparation 9), methylene chloride (5.0 mL) and the solution cooled to 0° C. DBU (0.32 mL, 2.14 mmol) and isopropylsulfonyl chloride (0.24 mL, 2.14 mmol) were added. The reaction was then stirred at 0° C. for 60.0 minutes and brought to room temperature with stirring overnight. The reaction was diluted with methylene chloride and washed with aqueous ammonium chloride, brine and the organic layer dried over sodium sulfate. The title compound was purified by radial chromatography eluting with methylene chloride to give 250 mg (50%) of the purified title compound.

$^1$H nmr ($CDCl_3$) δ 1.02 (d, 3H, J=8 Hz), 1.20 (d, 3H, J=8 Hz), 1.7–2.1 (m, 6H), 2.30 (s, 3H), 2.83–2.95 (m, 1H) 3.25–3.30 (m, 1H), 3.50 (d, 1H, J=8 Hz), 3.90 (m, 1H), 7.05–7.13 (m, 4H). Mass Spectrum (ES MS): M-1=280. Analysis calculated for $C_{15}H_{23}NO_2S$: % C, 64.02; % H, 8.24; % N, 4.98. Found: % C, 63.84; % H, 8.27; % N, 4.99.

EXAMPLE 29

Preparation of (+,-) Trans-3-{4-[2-(Propane-2-sulfonylamino)-cyclopentyl]-phenyl}-acrylic Acid Ethyl Ester

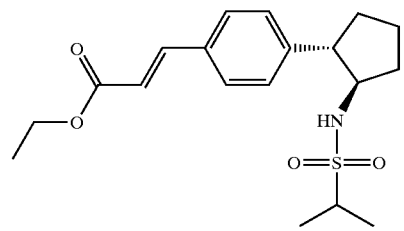

Scheme V, step A : (+,-) Trans propane-2-sulfonic acid [2-(4-iodo-phenyl)-cyclopentyl]-amide (150 mg, 0.38 mmol, prepared in example 2) was dissolved in DMF (5.0 mL) and ethyl acrylate (103 uL, 0.95 mmol), triethylamine (186 uL, 1.3 mmol), palladium acetate (4 mg, 0.02 mmol), and triphenylphosphine (10 mg, 0.04 mmol) were added. The reaction was heated to 80° C. and stirred overnight under nitrogen. Allowed the reaction to cool and diluted with 75 mL of 10% aqueous sodium bisulfate and extracted into methylene chloride (2×50 mL). Dried the organics over sodium sulfate, filtered and concentrated in vacuo to a crude brown oil. The desired compound was purified by radial chromatography eluting with methylene chloride followed by the addition of 2% MeOH. The appropriate fractions were concentrated to provide 63 mg (45%) of a near-colorless oil of the title compound.

Mass Spectrum (ES MS): M−1=364.

EXAMPLE 30

Preparation of (+,−) Cis-propane-2-sulfonic Acid (2-p-bromophenyl-cyclopentyl)-amide

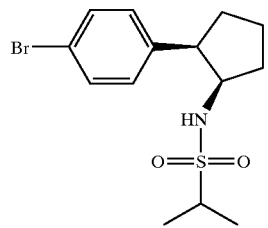

Scheme II, step A: A 100 mL round bottom flask equipped with a magnetic stirrer was charged with (+,−) cis-[2-(4-bromo-phenyl)-cyclopentylamine oxalate salt (500 mg, 1.51 mmol), methylene chloride (5.0 mL) and the solution was cooled to 0° C. DBU (1.8 mL, 12.1 mmol) and isopropyl-sulfonyl chloride (1.02 mL, 9.06 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound was purified by radial chromatography eluting with methylene chloride to give 233 mg (45%) of the purified title compound. The nmr was consistent with the assigned structure.

Mass Spectrum (ES MS): M−1=344, 346.

EXAMPLE 30A

Preparation of (S,S) Cis-propane-2-sulfonic Acid (2-p-bromophenyl-cyclopentyl)-amide

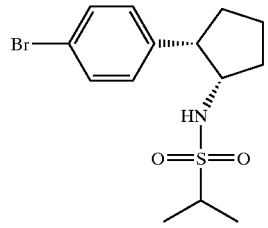

The racemic cis compound (233 mg) from example 30 was separated into individual enantiomers by chiral chromatography. The semiprep column used was 1×25 cm Chiralcel AD eluting with a gradient of 5%–50% IPA/Heptane over 30 min at a flow of 5.0 ml/min monitoring at a uv wavelength of 260 nm. The analytical column was 0.46×25 cm Chiralcel AD eluting with a gradient of 5%–50% IPA/Heptane over 30 min at a flow of 1.0 ml/min monitoring at a uv wavelength of 220 nm. The early eluting compound had a retention time of 9.1 min. The yield was 109 mg. Enantiomeric excess was estimated to be 97% by HPLC.

Mass Spectrum (ES MS): M−1=346.

EXAMPLE 30B

Preparation of (R,R) Cis-propane-2-sulfonic Acid (2-p-bromophenyl-cyclopentyl)-amide

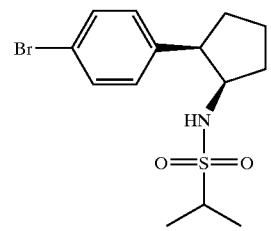

The racemic cis compound (233 mg) from example 30 was separated into individual enantiomers by chiral chromatography. The semiprep column used was 1×25 cm Chiralcel AD eluting with a gradient of 5%–50% IPA/Heptane over 30 min at a flow of 5.0 ml/min monitoring at a uv wavelength of 260 nm. The analytical column was 0.46×25 cm Chiralcel AD eluting with a gradient of 5%–50% IPA/Heptane over 30 min at a flow of 1.0 ml/min monitoring at a uv wavelength of 220 nm. The late eluting compound had a retention time of 10.4 min. The yield was 109 mg. Enantiomeric excess was estimated to be 88% by HPLC.

Mass Spectrum (ES MS): M−1=346.

EXAMPLE 31

Preparation of (+,−) Cis-propane-2-sulfonic Acid (2-p-chlorophenyl-cyclopentyl)-amide

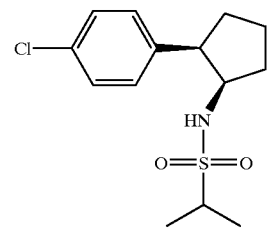

Scheme II, step A: A 100 mL round bottom flask equipped with a magnetic stirrer was charged with (+,−) cis-[2-(4-chloro-phenyl)-cyclopentylamine oxalate salt (200 mg, 0.70 mmol), methylene chloride (5.0 mL) and the solution was cooled to 0° C. DBU (0.84 mL, 5.60 mmol) and isopropyl-sulfonyl chloride (0.47 mL, 4.20 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound was purified by radial chromatography eluting with methylene chloride to give 116 mg (55%) of the purified title compound. The nmr was consistent with the assigned structure.

Mass Spectrum (ES MS): M−1=300, 302. Analysis calculated for $C_{14}H_{20}ClNO_2S$: % C, 55.71; % H, 6.68; % N, 4.64. Found: % C, 55.39; % H, 6.57; % N, 4.57.

EXAMPLE 32

Preparation of (+,−) Cis-propane-2-sulfonic Acid (2-(2,4-difluorophenyl)-cyclopentyl)-amide

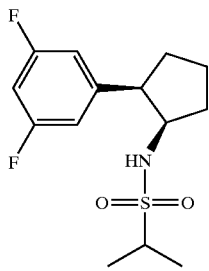

Scheme II, step A: A 100 mL round bottom flask equipped with a magnetic stirrer was charged with (+,−) cis-[2-(3,5-difluoro-phenyl)-cyclopentylamine (83 mg, 0.42 mmol), methylene chloride (5.0 mL) and the solution cooled to 0° C. DBU (0.08 mL, 0.51 mmol) and isopropylsulfonyl chloride (0.06 mL, 0.51 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound was purified by radial chromatography eluting with methylene chloride to give 83 mg (65%) of the purified title compound. The nmr was consistent with the assigned structure.

Mass Spectrum (ES MS): M−1=302. Analysis calculated for $C_{14}H_{19}F_2NO_2S$: % C, 55.43; % H, 6.31; % N, 4.62. Found: % C, 55.25; % H, 6.13; % N, 4.60.

EXAMPLE 32-A

Preparation of (1S,2S) Cis-propane-2-sulfonic Acid (2-(2,4-difluorophenyl)-cyclopentyl)-amide

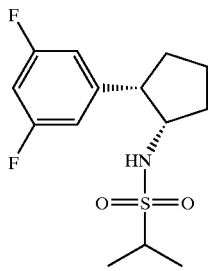

The racemic cis compound (570 mg) from example 32 was separated into individual enantiomers by chiral chromatography. The prep column used was 8×27 cm Chiralcel OD eluting with 90% Heptane/10% IPA at a flow of 330.0 mL/min monitoring at a UV wavelength of 255 nm. The analytical column was 0.46×25 cm Chiralcel OD-H eluting with 90% Heptane/10% IPA at a flow of 1.0 mL/min monitoring at a UV wavelength of 220 nm. The early eluting compound had a retention time of 6.9 min. The yield was 263 mg. Enantiomeric excess was estimated to be 99% by HPLC.

Mass Spectrum (ES MS): M+1=304.

EXAMPLE 32-B

Preparation of (1R,2R) Cis-propane-2-sulfonic Acid (2-(2,4-difluorophenyl)-cyclopentyl)-amide

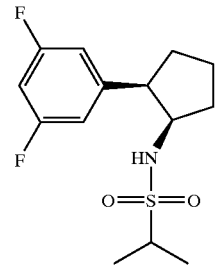

The racemic cis compound (570 mg) from example 32 was separated into individual enantiomers by chiral chromatography. The prep column used was 8×27 cm Chiralcel OD eluting with 90% Heptane/10% IPA at a flow of 330.0 mL/min monitoring at a UV wavelength of 255 nm. The analytical column was 0.46×25 cm Chiralcel OD-H eluting with 90% Heptane/10% IPA at a flow of 1.0 mL/min monitoring at a UV wavelength of 220 nm. The late eluting compound had a retention time of 11.1 min. The yield was 265 mg. Enantiomeric excess was estimated to be 99% by HPLC.

Mass Spectrum (ES MS): M+1=304.

EXAMPLE 33

Preparation of (+,−) Cis-Propane-2-sulfonic Acid [2-(3-fluoro-phenyl)-cyclopentyl]-amide

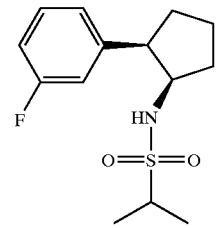

Scheme II, step A: A 100 mL round bottom flask equipped with a magnetic stirrer was charged with (+,−) cis-[2-(3-fluoro-phenyl)-cyclopentylamine (650 mg, 3.63 mmol) from preparation 14, methylene chloride (15.0 mL) and the solution cooled to 0° C. DBU (0.65 mL, 4.35 mmol) and isopropylsulfonyl chloride (0.49 mL, 4.35 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound.was purified by radial chromatography eluting with methylene chloride to give 573 mg (55%) of the purified title compound as a white solid. The nmr was consistent with the assigned structure.

Mass Spectrum (ES MS): M−1=284. Analysis calculated for $C_{14}H_{20}FNO_2S$: % C, 58.92; % H, 7.06; % N, 4.91. Found: % C, 58.90; % H, 6.96; % N, 4.94.

EXAMPLE 34

Preparation of (+,−) Cis-Propane-2-sulfonic Acid [2-(3,4-difluoro-phenyl)-cyclopentyl]-amide

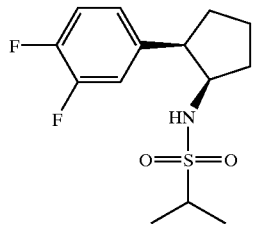

Scheme II, step A: A 100 mL round bottom flask equipped with a magnetic stirrer was charged with (+,−) cis-[2-(3,4-difluoro-phenyl)-cyclopentylamine (1.40 g, 7.10 mmol) from preparation 15, methylene chloride (20.0 mL) and the solution cooled to 0° C. DBU (1.27 mL, 8.52 mmol) and isopropylsulfonyl chloride (0.96 mL, 8.52 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound was purified by radial chromatography eluting with methylene chloride to give 910 mg (42%) of the purified title compound. The nmr was consistent with the assigned structure.

Mass Spectrum (ES MS): M−1=302. Analysis calculated for $C_{14}H_{19}F_2NO_2S$: % C, 55.43; % H, 6.31; % N, 4.62. Found: % C, 55.16; % H, 6.20; % N, 4.51.

EXAMPLE 35

Preparation of (1S,2S) Cis-Propane-2-sulfonic Acid [2-(4-cyano-phenyl)-cyclopentyl]-amide

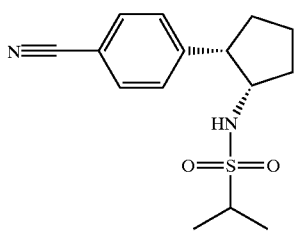

The chiral product from example 17A (128 mg, 0.33 mmol) was dissolved in 4 mL DMF and degassed. Zinc cyanide (23 mg, 0.20 mmol) and [1,1'-Bis(diphenylphosphino)-ferrocene]dichloropalladium(II), complex with dichloromethane 1:1 (21 mg, 0.03 mmol) was added and the reaction heated to 125° C. with stirring overnight. The reaction had not progressed far and so 0.5 mL of water, Tris(dibenzylideneacetone)-dipalladium(0) (8 mg), and zinc cyanide (20 mg) were added and the reaction heated to 130° C. with stirring overnight. The reaction was diluted with methylene chloride and washed with dilute sodium bicarbonate. The organic layer was dried over sodium sulfate and concentrated to a crude brown oil. The title compound was purified by radial chromatography eluting with methylene chloride to 2% MeOH/methylene chloride to give 21 mg (22%) of the purified title compound as a colorless oil. The nmr was consistent with the assigned structure.

Mass Spectrum (ES MS): M−1=291.

EXAMPLE 36

Preparation of (1R,2R) Cis-Propane-2-sulfonic Acid (2-(4-cyano-phenyl)-cyclopentyl]-amide

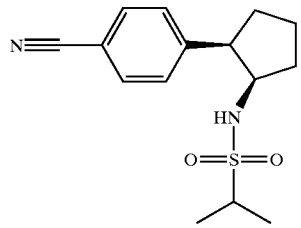

The chiral product from example 17B (131 mg, 0.33 mmol) was dissolved in 4 mL DMF, 0.5 mL water and degassed. Zinc cyanide (70 mg, 0.60 mmol), Tris (dibenzylideneacetone)-dipalladium(0) (15 mg, 0.02 mmol) and 1,1'-Bis(diphenylphosphino)-ferrocene (22 mg, 0.04 mmol) were added and the reaction heated to 135° C. with stirring overnight. The reaction was diluted with methylene chloride and washed with dilute sodium bicarbonate. The organic layer was dried over sodium sulfate and concentrated to a crude brown oil. The title compound was purified by radial chromatography eluting with 0.2% MeOH/methylene chloride to 2% MeOH/methylene chloride to give 75 mg (77%) of the purified title compound as a light yellow oil.

Mass Spectrum (ES MS): M−1=291.

EXAMPLE 37

Preparation of (+,−) Cis Propane-2-sulfonic Acid [2-(2',4'-difluoro-biphenyl-4-yl)-cyclopentyl]-amide

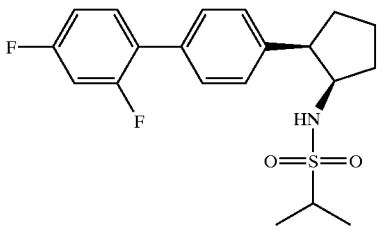

Scheme II, step C: The Suzuki coupling of (+,−) Cis propane-2-sulfonic acid [2-(4-iodo-phenyl)-cyclopentyl]-amide (710 mg, 1.81 mmol, prepared in example 17) and 2,4-difluorophenylboronic acid (285 mg, 1.81 mmol) was accomplished in a manner analogous to that described in example 27. The reaction was worked up in a manner analogous to example 3. Purification by silica chromatography using a Chromatotron® was achieved eluting with methylene chloride. Further purification was achieved by reverse phase C18 chromatography to afford 213 mg (31%) of the title compound as a white solid.

Mass Spectrum (ES MS): M−1=378. Analysis calculated for $C_{20}H_{23}F_2NO_2S$: % C, 63.30; % H, 6.11; % N, 3.69. Found: % C, 62.95; % H, 6.05; % N, 3.75.

EXAMPLE 38

Preparation of (+,−) Cis Propane-2-sulfonic Acid [2-(3',5'-difluoro-biphenyl-4-yl)-cyclopentyl]-amide

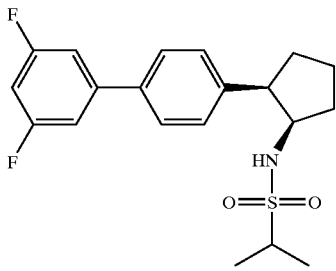

Scheme II, step C: The Suzuki coupling of (+,−) Cis propane-2-sulfonic acid [2-(4-iodo-phenyl)-cyclopentyl]-amide (225 mg, 0.57 mmol, prepared in example 17) and 3,5-difluorophenylboronic acid (108 mg, 0.69 mmol) was accomplished in a manner analogous to the procedure described in example 27. The reaction was worked up in a manner analogous to example 3. Purification by silica chromatography using a Chromatotron® was achieved eluting with methylene chloride to afford 110 mg (51%) of the title compound as a colorless oil.

Mass Spectrum (ES MS): M−1=378. Analysis calculated for $C_{20}H_{23}F_2NO_2S \times 0.4 H_2O$: % C, 62.12; % H, 6.20; % N, 3.62. Found: % C, 61.92; % H, 5.82; % N, 3.71.

EXAMPLE 39

Preparation of (+,−) Cis Propane-2-sulfonic Acid [2-(4'-methoxy-biphenyl-4-yl)-cyclopentyl)-amide

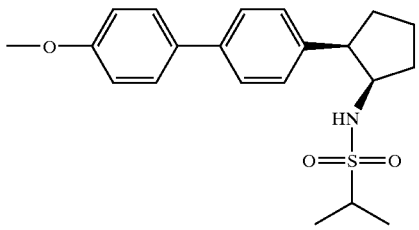

Scheme II, step C: The Suzuki coupling of (+,−) Cis propane-2-sulfonic acid [2-(4-iodo-phenyl)-cyclopentyl]-amide (200 mg, 0.51 mmol, prepared in example 17) and 4-methoxyphenylboronic acid (93 mg, 0.61 mmol) was accomplished in a manner analogous to the procedure described in example 27. The reaction was worked up in a manner analogous to example 3. Purification by silica chromatography using a Chromatotron® was achieved eluting with methylene chloride to afford 170 mg (89%) of the title compound.

Mass Spectrum (ES MS): M−1=372. Analysis calculated for $C_{21}H_{27}NO_3S \times 0.5 H_2O$: % C, 65.94; % H, 7.38; % N, 3.66. Found: % C, 65.65; % H, 7.06; % N, 3.81.

EXAMPLE 40

Preparation of (+,−) Cis Propane-2-sulfonic Acid [2-(3'-acetamido-biphenyl-4-yl)-cyclopentyl]-amide

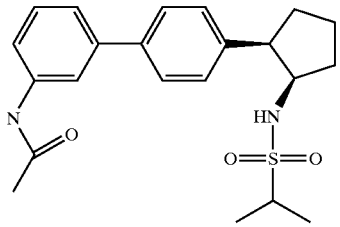

Scheme II, step C: The Suzuki coupling of (+,−) Cis propane-2-sulfonic acid [2-(4-iodo-phenyl)-cyclopentyl]-amide (200 mg, 0.51 mmol, prepared in example 17) and 3-acetamidophenylboronic acid (109 mg, 0.61 mmol) was accomplished in a manner analogous to the procedure described in example 27. The reaction was worked up in a manner analogous to example 3. Purification by silica chromatography using a Chromatotron® was achieved eluting with 2% methanol/methylene chloride to afford 85 mg (42%) of the title compound as a white solid when concentrated from ether.

Mass Spectrum (FD MS): M=400. Analysis calculated for $C_{22}H_{28}N_2O_3S \times 0.3 H_2O$: % C, 65.09; % H, 7.10; % N, 6.90. Found: % C, 64.86; % H, 6.94; % N, 6.75.

EXAMPLE 41

Preparation of (+,−) Cis Propane-2-sulfonic Acid [2-(4'-trifluoromethoxy-biphenyl-4-yl)-cyclopentyl]-amide

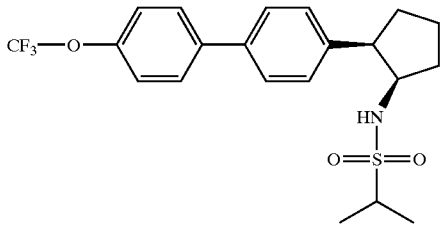

Scheme II, step C: The Suzuki coupling of (+,−) Cis propane-2-sulfonic acid [2-(4-iodo-phenyl)-cyclopentyl]-amide (203 mg, 0.52 mmol, prepared in example 17) and 4-trifluoromethoxyphenylboronic acid (128 mg, 0.62 mmol) was accomplished in a manner analogous to the procedure described in example 27. The reaction was worked up in a manner analogous to example 3. Purification by silica chromatography using a Chromatotron® was achieved eluting with methylene chloride, followed by a second chromatography eluting with 0.2% MeOH/methylene chloride to afford 97 mg (44%) of the title compound.

Mass Spectrum (ES MS): M−1=426. Analysis calculated for $C_{21}H_{24}F_3NO_3S$: % C, 59.00; % H, 5.66; % N, 3.28. Found: % C, 58.94; % H, 5.65; % N, 3.32.

EXAMPLE 42

Preparation of (S,S) Cis-4'-[2-(Propane-2-sulfonylamino)-cyclopentyl]-biphenyl-4-carboxylic Acid Methylamide

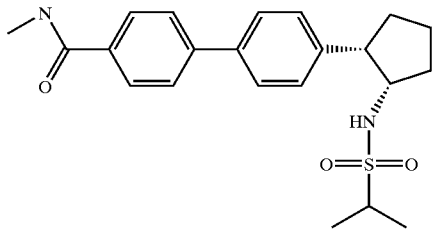

Scheme II, step C: The Suzuki coupling of (S,S) Cis propane-2-sulfonic acid (2-(4-iodo-phenyl)-cyclopentyl]-amide (62 mg, 0.16 mmol, prepared in example 17A) and N-Methyl-4-(4,4,5,5-tetramethyl-[1,3,2]dioxaborolan-2-yl)-benzamide (49 mg, 0.19 mmol, prepared in preparation 17) was accomplished in a manner analogous to the procedure described in example 27. The reaction was worked up in a manner analogous to example 3. Purification by silica chromatography using a Chromatotron® was achieved eluting with 2% methanol/methylene chloride to afford 44 mg (70%) of the title compound.

Mass Spectrum (ES MS): M+1=401. Analysis calculated for $C_{22}H_{28}N_2O_3S \times 0.4\ H_2O$: % C, 64.81; % H, 7.12; % N, 6.87. Found: % C, 64.70; % H, 6.72; % N, 6.80.

EXAMPLE 43

Preparation of (R,R) Cis-4'-[2-(Propane-2-sulfonylamino)-cyclopentyl]-biphenyl-4-carboxylic Acid Methylamide

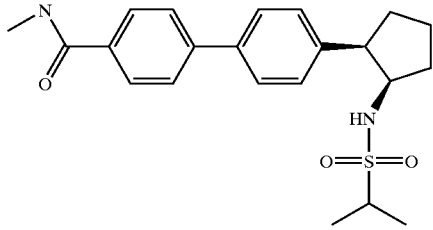

Scheme II, step C: The Suzuki coupling of (R,R) Cis propane-2-sulfonic acid [2-(4-iodo-phenyl)-cyclopentyl]-amide (200 mg, 0.51 mmol, prepared in example 17B) and N-methyl-4-(4,4,5,5-tetramethyl-[1,3,2]dioxaborolan-2-yl)-benzamide (159 mg, 0.61 mmol, prepared in preparation 17) was accomplished in a manner analogous to the procedure described in example 27. The reaction was worked up in a manner analogous to example 3. Purification by silica chromatography using a Chromatotron® was achieved eluting with 2% methanol/methylene chloride to afford 128 mg (63%) of the title compound as a white solid.

Mass Spectrum (ES MS): M+1=401. Analysis calculated for $C_{22}H_{28}N_2O_3S \times 0.2\ H_2O$: % C, 65.38; % H, 7.08; % N, 6.93. Found: % C, 65.14; % H, 6.91; % N, 6.62.

EXAMPLE 44

Preparation of (+,−) Cis-Propane-2-sulfonic Acid (2-[4-(1-oxo-indan-5-yl)-phenyl]-cyclopentyl)-amide

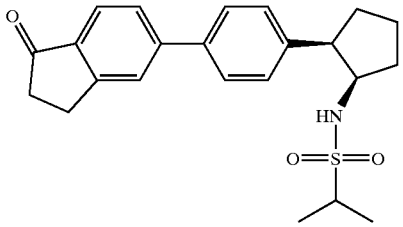

Scheme IIA: The compound from example 17 (200 mg, 0.51 mmol) was dissolved in 6 mL DMSO, potassium acetate (150 mg, 1.53 mmol) and the solution degassed. Add bis(pinacolato)diboron (142 mg, 0.56 mmol) followed by [1,1'-bis(diphenylphosphino)-ferrocene] dichloropalladium (II), complex with dichloromethane 1:1 (50 mg) and heated to 80° C. under nitrogen with stirring for 2 h. The reaction was allowed to cool and 5-bromo-1-indanone (107 mg, 0.51 mmol) added, followed by sodium carbonate (162 mg, 1.53 mmol) in 2 mL water and 50 mg additional catalyst. The reaction was heated overnight (18 h) at 105° C. The reaction was diluted with methylene chloride (100 mL) and washed with water (1×50 mL), brine (1×50 mL) and the organics dried over magnesium sulfate. The drying agent was rinsed thoroughly with methylene chloride. The filtrate was concentrated to a brown oil which was purified by radial chromatography eluting with 1% methanol/methylene chloride to afford 116 mg (57%) of the title compound as a white solid when concentrated from ether.

Mass Spectrum (ES MS): M−1=396. Analysis calculated for $C_{23}H_{27}NO_3S \times 0.7\ H_2O$: % C, 67.35; % H, 6.98; % N, 3.41. Found: % C, 66.98; % H, 6.53; % N, 3.49.

EXAMPLE 45

Preparation of (+,−) Cis-4'-[2-(Propane-2-sulfonylamino)-cyclopentyl]-biphenyl-4-sulfonic Acid Amide

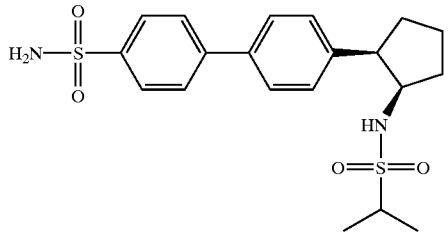

Scheme IIA: The compound from example 17 (250 mg, 0.64 mmol) was dissolved in 6 mL DMSO, potassium acetate (187 mg, 1.91 mmol) and the solution degassed. Add bis(pinacolato)diboron (178 mg, 0.70 mmol) followed by [1,1'-bis(diphenylphosphino)-ferrocene] dichloropalladium (II), complex with dichloromethane 1:1 (50 mg) and heated to 80° C. under nitrogen with stirring for 1 h. The reaction was allowed to cool and 4-bromobenzenesulphonamide (150 mg, 0.64 mmol) added, followed by sodium carbonate (202 mg, 1.91 mmol) in 2 mL water and 50 mg additional catalyst. The reaction was heated overnight (18 h) at 105° C. The reaction was diluted with methylene chloride (100 mL) and washed with water (1×50 mL), brine (1×50 mL) and the organics dried over magnesium sulfate. The drying agent was rinsed thoroughly with methylene chloride. The filtrate was concentrated to a yellow oil which was purified by radial chromatography eluting with 2% methanol/methylene chloride to afford 120 mg (45%) of the title compound as a white solid.

Mass Spectrum (ES MS): M+1=423. Analysis calculated for $C_{20}H_{26}N_2O_4S_2 \times 1.5\ H_2O$: % C, 53.43; % H, 6.50; % N, 6.23. Found: % C, 53.13; % H, 5.93; % N, 6.01.

EXAMPLE 45A

Preparation of (S,S) Cis-4'-[2-(Propane-2-sulfonylamino)-cyclopentyl]-biphenyl-4-sulfonic Acid Amide

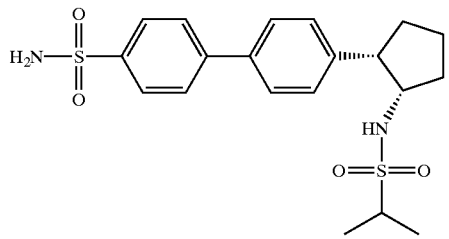

The racemic cis compound (110 mg) from example 45 was separated into individual enantiomers by chiral chromatography. The semiprep column used was 1×25 cm Chiralpak AD eluting with 30% Heptane/50% 3A alcohol/20% $CO_2$ at a flow of 5.0 mL/min, 35° C., 13,789 kPa (2000 psi), monitoring at a UV wavelength of 290 nm. The analytical column was 0.46×25 cm Chiralpak AD eluting with 100% 3A alcohol at a flow of 1.0 mL/min monitoring at a uv wavelength of 250 nm. The early eluting compound had a retention time of 5.2 min. The yield was 32 mg. Enantiomeric excess was estimated to be 99% by HPLC.

Mass Spectrum (ES MS): M−1=421.

EXAMPLE 45B

Preparation of (R,R) Cis-4'-[2-(Propane-2-sulfonylamino)-cyclopentyl]-biphenyl-4-sulfonic Acid Amide

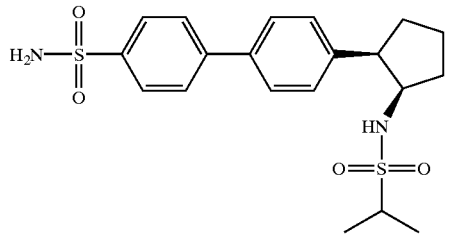

The racemic cis compound (110 mg) from example 45 was separated into individual enantiomers by chiral chromatography. The semiprep column used was 1×25 cm Chiralpak AD eluting with 30% Heptane/50% 3A alcohol/20% $CO_2$ at a flow of 5.0 mL/min, 35° C., 13,789 kPa (2000 psi), monitoring at a UV wavelength of 290 nm. The analytical column was 0.46×25 cm Chiralpak AD eluting with 100% 3A alcohol at a flow of 1.0 mL/min monitoring at a uv wavelength of 250 nm. The late eluting compound had a retention time of 6.8 min. The yield was 21 mg. Enantiomeric excess was estimated to be 90% by HPLC.

Mass Spectrum (ES MS): M−1=421.

EXAMPLE 46

Preparation of (+,−)-Cis-4'-[2-(Propane-2-sulfonylamino)-cyclopentyl]-biphenyl-4-carboxylic Acid

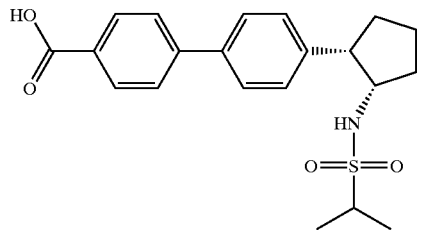

Scheme II, step C: The Suzuki coupling of (+,−) Cis propane-2-sulfonic acid [2-(4-iodo-phenyl)-cyclopentyl]-amide (245 mg, 0.62 mmol, prepared in example 17) and 4-carboxybenzeneboronic acid (114 mg, 0.69 mmol) was accomplished in a manner analogous to the procedure described in example 27. The reaction was worked up in a manner analogous to example 3. Purification by silica chromatography using a Chromatotron® was achieved eluting with 4% methanol/methylene chloride to afford 260 mg of the title compound which was further purified by semiprep C18 reverse phase HPLC to give 96 mg (40%) of the title compound as a white solid.

Mass Spectrum (ES MS): M+NH$_4$=405. Analysis calculated for $C_{21}H_{25}NO_4S \times 0.2\ H_2O$: % C, 64.49; % H, 6.55; % N, 3.58. Found: % C, 64.25; % H, 6.40; % N, 4.21*.

EXAMPLE 47

Preparation of (+,−) Cis-4'-[2-(Propane-2-sulfonylamino)-cyclopentyl]-biphenyl-4-carboxylic Acid Methylamide

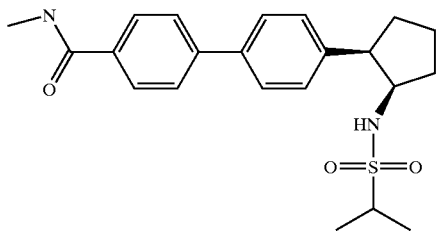

The compound from example 46 (60 mg, 0.16 mmol) was suspended in 4 mL of methylene chloride and dissolved upon addition of 4-methylmorpholine (0.05 mL, 0.48 mmol) while cooling to 0° C. Isobutylchloroformate (0.05 mL, 0.40 mnol) was slowly added and stirred for 30 min. To this mixture was added 0.9 mL (9.6 mmol) of 40% aqueous methylamine and stirred at 0° C. for 30 min. The reaction was allowed to warm to room temperature and washed with 1N HCl (1×50 mL). The organic layer was dried over sodium sulfate, filtered, and concentrated in vacuo to 120 mg of a colorless oil. Purification by silica chromatography using a Chromatotron® was achieved eluting with 2% methanol/methylene chloride to afford 49 mg (79%) of the title compound as a white solid.

Mass Spectrum (ES MS): M+1=401. Analysis calculated for $C_{22}H_{28}N_2O_3S\times 0.5\ H_2O$: % C, 64.52; % H, 7.14; % N, 6.84. Found: % C, 64.35; % H, 6.61; % N, 6.91.

EXAMPLE 48

Preparation of (+,−) Trans Propane-2-sulfonic Acid [2-(4-bromo-phenyl)-cyclopentyl]-amide

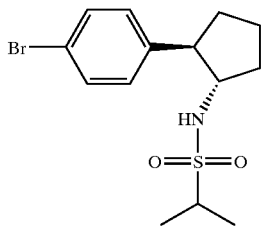

Scheme II, step A: Into a 250 mL 3 neck flask fitted with a stirrer and thermometer, 3.73 g (15.4 mmol) of 2-propanesulfonyl chloride was added dropwise to 3.30 g (14 mmol) of the compound from preparation 19 and 4.23 g (16.8 mmol) DBU in methylene chloride (90 mL) while stirring at 0° C. under a nitrogen atmosphere. The reaction was then allowed to warm to room temperature and stirred overnight. In the morning, the mixture was diluted with methylene chloride (100 mL), washed once with water, dried over potassium carbonate, and concentrated under reduced vacuum to yield 5.63 g of a solid. This material was purified via silica gel chromatography employing the Water's prep. 2000 and eluting with an isocratic solvent of hexane/ethyl acetate 7:3 to yield 3.54 g (73%) of a white solid. M.P. 128°–130° C.: Ion spray M.S. 346 (M*): Calculated for: $C_{14}H_{20}NO_2SBr$ Theory: C 48.56, H 5.82, N 4.04 Found: C 48.88, H 5.83, N 4.12.

EXAMPLES 49 AND 50

Preparation of (+,−) Trans 4'-[2-(Propane-2-sulfonylamino)-cyclopentyl]-biphenyl-4-sulfonic acid amide (A) and (+,−) Trans Propane-2-sulfonic Acid (2-{4'-[2-(propane-2-sulfonylamino)-cyclopentyl]-biphenyl-4-yl}-cyclopentyl)-amide (B)

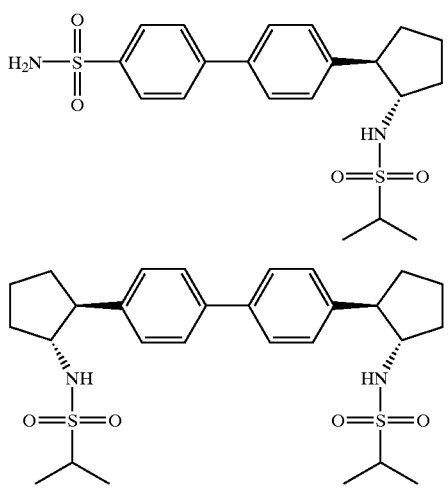

Scheme II, step C: Into a 100 mL single neck flask fitted with a stirrer was placed 400 mg (1.16 mmol) of the compound from example 48, 308 mg (1.21 mmol) of pinacolatodiboron, and 331 mg (3.37 mmol) potassium acetate in DMF (25 mL). This mixture was stirred at room temperature and de-gassed with argon for 10 minutes. Then 23 mg of $PdCl_2$(dppf) was added portion wise and the reaction was stirred at 80° C. under a nitrogen atmosphere for 2 hours. The dark mixture was allowed to cool to room temperature and 510 mg (2.10 mmol) of 4-bromosulfonamide and an additional 23 mg of $PdCl_2$ (dppf) was added portion wise. This was followed by the addition of 2.78 mL of 2.0 M sodium carbonate/water syringe wise. The mixture was then heated to 80° C. and stirred overnight. In the morning, the reaction was let cool to room temperature and poured into water. The desired material was extracted into ethyl acetate. The organic layer was washed once with water, dried over potassium carbonate, and concentrated under reduced vacuum to yield 731 mg of 2 spot material as a dark oil. This material was separated and purified via silica gel chromatography employing the Chromatotron® with a 4000 micron rotor and eluting with an isocratic solvent of methylene chloride/ethyl acetate 9:1 to yield 264 mg of compound B as a white solid. Ion spray M.S. 533 (M*+1):

Elution of the bottom spot yielded 100 mg (20%) of A as a slowly crystallizing oil. NMR was consistent with proposed structure. Ion spray M.S. 421.2 (M*−1): Calculated for: $C_{20}H_{26}N_2O_4S_2$ Theory: C 56.85, H 6.20, N 6.63 Found: C 56.18, H 5.88, N 6.95.

EXAMPLE 51

Preparation of (+,−) Trans 4'-[2-(Propane-2-sulfonylamino)-cyclopentyl]-biphenyl-4-carboxylic Acid

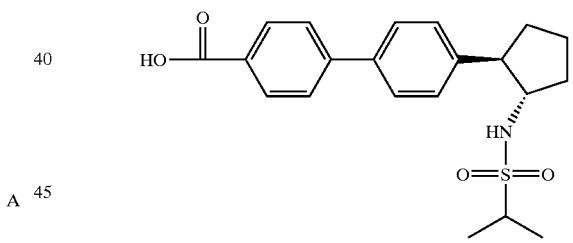

Scheme II, step C: Into a 50 mL single neck flask the compound from example 48 (500 mg, 1.45 mmol), 4-carboxybenzeneboronic Acid (271 mg, 1.61 mmol), palladium tetrakistriphenylphosphine 112 mg, 0.10 mmol), and 2.0 M sodium carbonate 2.5 mL (excess) were mixed together in 1,4-dioxane (15 mL) and stirred overnight at 80° C. In the morning the reaction was allowed to cool to room temperature and poured into 2N sodium hydroxide. This basic media was washed once with ethyl acetate. The basic media was then taken to pH 3 with 6N HCl and the desired material was extracted into ethyl acetate. The organic layer was washed once with water, dried over magnesium sulfate, and concentrated under reduced vacuum to yield 691 mg of a tan solid. This material was purified via silica gel chromatography employing the Chromatotron® with a 4000 micron rotor and eluting with an isocratic solvent of methylene chloride/methanol 9:1 to yield 300 mg as a white solid. Ion spray M.S. 387.2 (M*):

EXAMPLE 52

Preparation of (1R,2S) Trans Propane-2-sulfonic Acid [2-(4-bromo-phenyl)-cyclopentyl]-amide

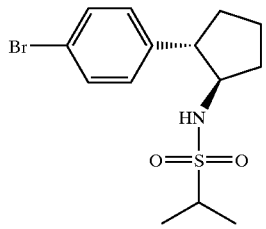

The racemic trans compound (11.2 g) from example 48 was separated into individual enantiomers by chiral chromatography. The prep column used was 8×29 cm Chiralcel OD eluting with 90% Heptane/10% IPA at a flow of 330.0 mL/min monitoring at a UV wavelength of 250 nm. The analytical column was 0.46×25 cm Chiralcel OD-H eluting with 90% Heptane/10% IPA at a flow of 1.0 mL/min monitoring at a UV wavelength of 240 nm. The early eluting compound had a retention time of 6.7 min. The yield was 4.6 g. Enantiomeric excess was estimated to be 99% by HPLC.

Mass Spectrum (ES MS): M−1=346. Calculated for: $C_{14}H_{20}BrNO_2S$ Theory: C 48.56, H 5.82, N 30 4.04 Found: C 48.76, H 5.82, N 4.13.

EXAMPLE 53

Preparation of (1S,2R) Trans Propane-2-sulfonic Acid [2-(4-bromo-phenyl)-cyclopentyl]-amide

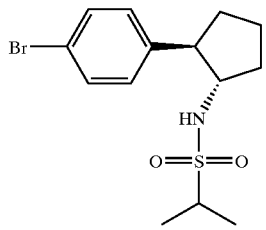

The racemic trans compound (11.2 g) from example 48 was separated into individual enantiomers by chiral chromatography. The prep column used was 8×29 cm Chiralcel OD eluting with 90% Heptane/10% IPA at a flow of 330.0 mL/min monitoring at a UV wavelength of 250 nm. The analytical column was 0.46×25 cm Chiralcel OD-H eluting with 90% Heptane/10% IPA at a flow of 1.0 mL/min monitoring at a UV wavelength of 240 nm. The late eluting compound had a retention time of 8.5 min. The yield was 4.9 g. Enantiomeric excess was estimated to be 98% by HPLC.

Mass Spectrum (ES MS): M−1=346.

EXAMPLE 54

Preparation of (1R,2S) Trans 4'-[2-(Propane-2-sulfonylamino)-cyclopentyl]-biphenyl-4-sulfonic Acid Amide

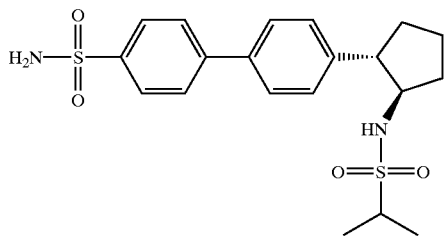

Scheme II, step C: Into a 50 mL single neck flask fitted with a stirrer was placed 400 mg (1.16 mmol) of the compound from example 52, 323 mg (1.27 mmol) of pinacolatodiboron, and 340 mg (3.47 mmol) potassium acetate in DMSO (20 mL). This mixture was stirred at room temperature and de-gassed with nitrogen for 2 minutes. Then, 75 mg of $PdCl_2$(dppf) was added portion wise and the reaction was stirred at 80° C. under a nitrogen atmosphere for 3 h. The dark mixture was allowed to cool to room temperature and 273 mg (1.16 mmol) of 4-bromobenzenesulfonamide and an additional 75 mg of PdCl2(dppf) was added portion wise. This was followed by the addition of 367 mg (3.47 mmol) of aqueous (5 mL) sodium carbonate syringe wise. The mixture was then heated to 90° C. and stirred overnight. In the morning the reaction was let cool to room temperature and poured into water. The desired material was extracted into methylene chloride. The organic layer was washed once with water, dried over sodium sulfate, and concentrated under reduced vacuum to yield 830 mg of 2 spot material as a dark oil. The slower eluting material was separated and purified via silica gel chromatography employing the Chromatotron® with a 4000 micron rotor and eluting with an isocratic solvent of 2% methanol/methylene chloride to yield 225 mg of a tan foam which was triturated with 1:1 EtOAc:Hexanes to give 135 mg (28%) of the desired product as a tan solid.

ES M.S. 421.2 (M*−1): Calculated for: $C_{20}H_{26}N_2O_4S_2$: Theory: C 56.85, H 6.20, N 6.63 Found: C 56.62, H 5.99, N 6.48.

EXAMPLE 55

Preparation of (1S,2R) Trans 4'-[2-(Propane-2-sulfonylamino)-cyclopentyl]-biphenyl-4-sulfonic Acid Amide

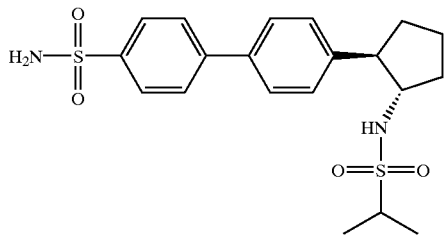

Scheme II, step C: Into a 50 mL single neck flask fitted with a stirrer was placed 250 mg (0.73 mmol) of the compound from example 53, 200 mg (0.79 mmol) of pinacolatodiboron, and 215 mg (2.19 mmol) potassium acetate in DMF (20 mL). This mixture was stirred at room temperature and de-gassed with argon for 10 minutes. Then, 15 mg of PdCl$_2$(dppf) was added portion wise and the reaction was stirred at 80° C. under a nitrogen atmosphere for 2 hours. The dark mixture was allowed to cool to room temperature and 327 mg (1.20 mmol) of 4-bromobenzenesulfonamide and an additional 15 mg of PdCl$_2$(dppf) was added portion wise. This was followed by the addition of 1.80 mL of 2.0 M sodium carbonate/water syringe wise. The mixture was then heated to 80° C. and stirred overnight. In the morning the reaction was let cool to room temperature and poured into water. The desired material was extracted into ethyl acetate. The organic layer was washed once with water, dried over potassium carbonate, and concentrated under reduced vacuum to yield 417 mg of 2 spot material as a dark oil. This material was separated and purified via silica gel chromatography employing the Chromatotron® with a 4000 micron rotor and eluting with an isocratic solvent of methylene chloride/ethyl acetate 7:3 to yield 35 mg (11%) of the bottom spot as an oil. Ion spray M.S. 421.2 (M*–1):

EXAMPLE 56

Preparation of (1R,2S) Trans 4'-[2-(Propane-2-sulfonylamino)-cyclopentyl]-biphenyl-4-carboxylic Acid Methylamide

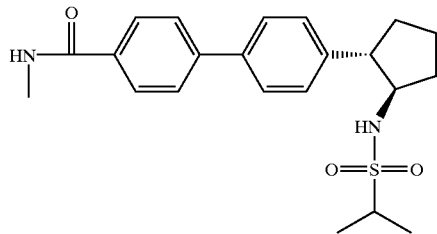

Scheme II, step C: The Suzuki coupling of the chiral compound from example 52 (313 mg, 0.90 mmol) and the boronic ester from preparation 17 (236 mg, 0.90 mmol) was accomplished in a manner analogous to the procedure described in example 27. The reaction was worked up in a manner analogous to example 3. Purification by silica chromatography using a Chromatotron® was achieved eluting with 2% methanol/methylene chloride to afford 200 mg (55%) of the title compound as a white solid.

Mass Spectrum (ES MS): M–1=399. Analysis calculated for C$_{22}$H$_{28}$N$_2$O$_3$S×0.1 H$_2$O: % C, 65.68; % H, 7.06; % N, 6.96. Found: % C, 65.43; % H, 6.73; % N, 6.87.

EXAMPLE 57

Preparation of (1S,2R) Trans 4'-[2-(Propane-2-sulfonylamino)-cyclopentyl]-biphenyl-4-carboxylic Acid Methylamide

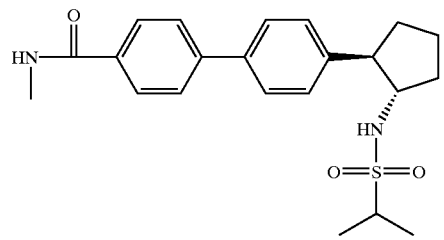

Scheme II, step C: Into a 50 mL single neck flask the compound from example 53 (200 mg, 0.58 mmol), the boronic ester from preparation 17 (170 mg, 0.63 mmol), palladium tetrakistriphenylphosphine (50 mg, 0.10 mmol), and 1.0 mL of 2M sodium carbonate were mixed together in 10 mL of 1,4-dioxane and stirred overnight at 80° C. In the morning, the reaction was let cool to room temperature and poured into water. The desired material was extracted into ethyl acetate. The organic layer was washed once with water, dried over potassium carbonate, and concentrated under reduced vacuum to yield 370 mg of a dark oil. This material was purified via silica gel chromatography employing the Chromatotron® with a 4000 micron rotor and eluting with an isocratic solvent of methylene chloride/ethyl acetate 7:3 to yield 110 mg (47%) as a semi-solid. Ion spray M.S. 399.2 (M*–1): Calculated for: C$_{22}$H$_{28}$N$_2$O$_3$S Theory: C 65.97, H 7.04, N 6.99 Found: C 66.26, H 6.81, N 6.84.

EXAMPLE 58

Preparation of (+,–) Trans 4'-[2-(Propane-2-sulfonylamino)-cyclopentyl]-biphenyl-4-carboxylic Acid Methylamide

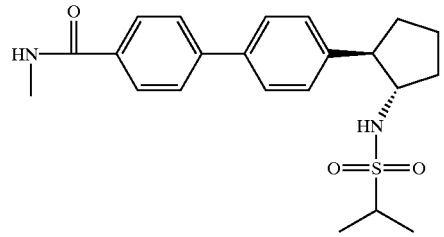

Into a 50 mL single neck flask fitted with a stirrer, 2 mL of oxalyl chloride was added syringe wise to 290 mg (0.75 mmol) of the compound from example 51 in methylene chloride (20 mL) while stirring at room temperature under nitrogen. Immediately after addition, 1 drop of DMF was added by pipette initiating a foaming of the mixture. The reaction was stirred for 1 hour at this temperature and then concentrated under reduced vacuum to yield a tan solid. This material was placed into 1,4 dioxane (25 mL) and added dropwise to a stirred solution of 40% methylamine (3 mL) at room temperature. After addition, this mixture was stirred overnight. In the morning, the solution was concentrated under reduced vacuum. The resulting oil was taken into methylene chloride and the organic layer was washed once with water, dried over potassium carbonate, and concentrated under reduced vacuum to yield 311 mg of an oil. This material was purified via silica gel chromatography employing the Chromatotron® with a 4000 micron rotor and eluting with an isocratic solvent of methylene chloride/ethyl acetate 7:3 to yield 117 mg (39%) as a white foam. Ion spray M.S. 399.1 (M*−1) and 401.2 (M*+1):

EXAMPLE 59

Preparation of (+,−) Cis-Propane-2-sulfonic Acid [2-(4-fluoro-phenyl)-cyclopentyl]-amide

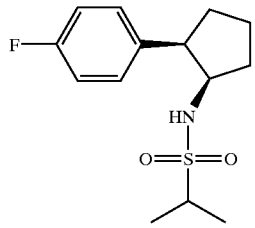

Scheme II, step A: A 100 mL round bottom flask equipped with a magnetic stirrer was charged with (+,−) cis-[2-(4-fluoro-phenyl)-cyclopentylamine (131 mg, 0.73 mmol), methylene chloride (5.0 mL) and the solution cooled to 0° C. DBU (0.13 mL, 0.88 mmol) and isopropylsulfonyl chloride (0.10 mL, 0.88 mmol) were added. The reaction was then stirred at 0° C. for 60.0 minutes and brought to room temperature with stirring overnight. The reaction was diluted with methylene chloride and washed with 1N HCl, brine and the organic layer dried over sodium sulfate. The title compound was purified by radial chromatography eluting with methylene chloride to give 135 mg (65%) of the purified title compound as a colorless oil.

Mass Spectrum (ES MS): M−1=284. Analysis calculated for $C_{14}H_{20}FNO_2S \times 0.1\ H_2O$: % C, 58.55; % H, 7.09; % N, 4.88. Found: % C, 58.37; % H, 6.88; % N, 4.89.

EXAMPLE 60

Preparation of (+,−) Cis Propane-2-sulfonic Acid (2-biphenyl-4-yl-cyclopentyl)-amide

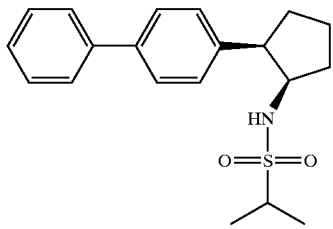

Scheme II, step C: The Suzuki coupling of (+,−) Cis propane-2-sulfonic acid [2-(4-iodo-phenyl)-cyclopentyl]-amide (167 mg, 0.43 mmol, prepared in example 17) and phenylboronic acid (62 mg, 0.51 mmol) was accomplished in a manner analogous to the procedure described in example 27. The reaction was worked up in a manner analogous to example 3. Purification by silica chromatography using a Chromatotron® was achieved eluting with methylene chloride. Further purification was achieved by reverse phase C18 chromatography to afford 77 mg (53%) of the title compound as a solid.

Mass Spectrum (ES MS): M−1=342. Analysis calculated for $C_{20}H_{25}NO_2S \times 0.2\ H_2O$: % C, 69.21; % H, 7.38; % N, 4.04. Found: % C, 68.79; % H, 7.02; % N, 4.41.

EXAMPLE 61

Preparation of (+,−) Cis-4-Chloro-N-{4-[2-(propane-2-sulfonylamino)-cyclopentyl]-phenyl}-benzamide

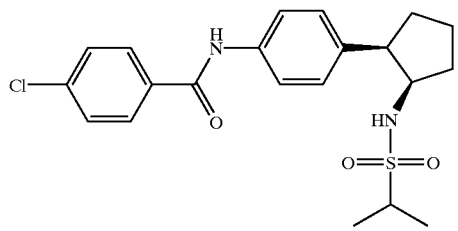

Scheme IV, step C: The amine (70 mg, 0.247 mmol, prepared in example 23), triethylamine (0.04 mL, 0.272 mmol), and methylene chloride (1.7 mL) were combined in a 15 mL round bottomed flask, fitted with a y-tube, capped by a rubber stopper, and nitrogen gas, and stirbar. Next, by syringe, 4-chlorobenzoyl chloride (0.03 mL, 0.272 mmol) in methylene chloride (1.5 mL), was added, and stirred at room temperature for one hour. Next the reaction mixture was quenched with water, and extracted with methylene chloride (25 mL×3). The organic layer was dried (MgSO$_4$), filtered, and concentrated under reduced vacuum, yielding 410 mg yellow viscous oil. This material was purified via silica gel chromatography, utilizing a Chromatotron® with a 4000 uM rotor in a 1:1 hexane:ethyl acetate solvent system, yielding the title compound (30 mg, 29%) as off-white crystals.

Electrospray-MS 422.0 (M*+1); Analysis; Theory: C 59.92; H 5.99; N 6.65; Found: C 59.85; H 5.98; N 6.50.

EXAMPLE 62

Preparation of (+,−) Cis-3,5-Difluoro-N-{4-[2-(propane-2-sulfonylamino)-cyclopentyl]-phenyl}-benzamide

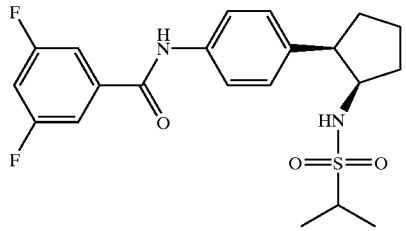

Scheme IV, step C: The amine (200 mg, 0.706 mmol, prepared in example 23), triethylamine (0.11 mL, 0.776 mmol), 3,5-difluorobenzoyl chloride (0.1 mL, 0.776 mmol) and methylene chloride (4.7 mL) were reacted in a manner analogous to the procedure described in Example 61. The title compound was isolated as a white solid (220 mg, 74%).

Electrospray-MS 423.0 (M*+1); Analysis; Theory: C 59.70; H 5.72; N 6.63; Found: C 59.57; H 5.72; N 6.55.

EXAMPLE 63

Preparation of (+,−) Cis-2,4-Difluoro-N-{4-[2-(propane-2-sulfonylamino)-cyclopentyl]-phenyl}-benzamide

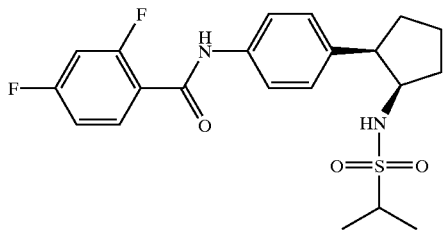

Scheme IV, step C: The amine (200 mg, 0.706 mmol, prepared in example 23), triethylamine (0.11 mL, 0.776 mmol), 2,4-difluorobenzoyl chloride (0.1 mL, 0.776 mmol) and methylene chloride (4.7 mL) were reacted in a manner analogous to the procedure described in Example 61. The title compound (470 mg, 100%) was isolated as a white solid.

Electrospray-MS 423.0 (M*+1); Analysis; Theory: C 59.70; H 5.72; N 6.63; Found: C 59.39; H 5.68; N 6.51.

EXAMPLE 64

Preparation of (+,−) Cis-3-Cyano-N-{4-[2-(propane-2-sulfonylamino)-cyclopentyl]-phenyl}-benzamide

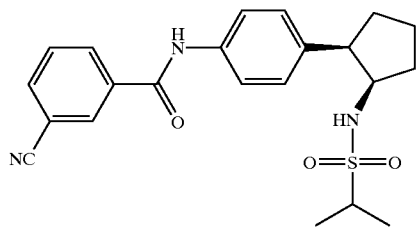

Scheme IV, step C: The amine (200 mg, 0.706 mmol, prepared in example 23), triethylamine (0.11 mL, 0.776 mmol), 3-cyanobenzoyl chloride (0.1 mL, 0.776 mmol) and methylene chloride (4.7 mL) were reacted in a manner analogous to the procedure described in Example 61. The title compound (165 mg, 57%) was isolated as a white solid.

Electrospray-MS 412.0 (M*+1); Analysis; Theory: C 64.21; H 6.12; N 10.21; Found: C 63.71; H 6.19; N 9.92.

EXAMPLE 65

Preparation of (+,−) Cis-4-Cyano-N-{4-[2-(propane-2-sulfonylamino)-cyclopentyl]-phenyl}-benzamide

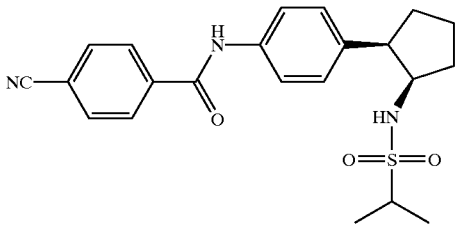

Scheme IV, step C: The amine (200 mg, 0.706 mmol, prepared in example 23), triethylamine (0.11 mL, 0.776 mmol), 4-cyanobenzoyl chloride (0.1 mL, 0.776mmol) and methylene chloride (4.7 mL) were reacted in a manner analogous to the procedure described in Example 61. The title compound (278 mg, 96%) was isolated as a white solid.

Electrospray-MS 412.0 (M*+1); Analysis; Theory: C 64.21; H 6.12; N 10.21; Found: C 63.69; H 6.16; N 9.93.

EXAMPLE 66

Preparation of (+,−) Cis-N-{4-[2-(Propane-2-sulfonylamino)-cyclopentyl]-phenyl}-terephthalamic Acid Methyl Ester

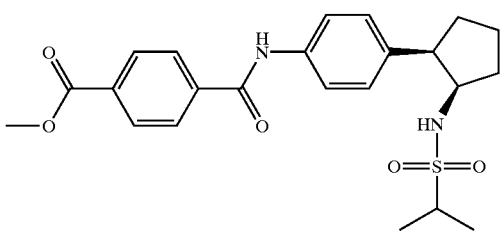

Scheme IV, step C: The amine (400 mg, 1.41 mmol, prepared in example 23), triethylamine (0.22 mL, 1.552 mmol), terephthalic acid monomethyl ester chloride (0.2 mL, 1.55 mmol) and methylene chloride (9.4 mL) were reacted in a manner analogous to the procedure described in Example 61. The title compound (535 mg, 85%) was isolated as a white solid.

Electrospray-MS 446.0 (M*+1); Analysis; Theory: C 62.14; H 6.35; N 6.30; Found: C 61.74; H 6.26; N 6.25.

EXAMPLE 67

Preparation of (+,−) Cis-4-Nitro-N-{4-[2-(propane-2-sulfonylamino)-cyclopentyl]-phenyl}-benzamide

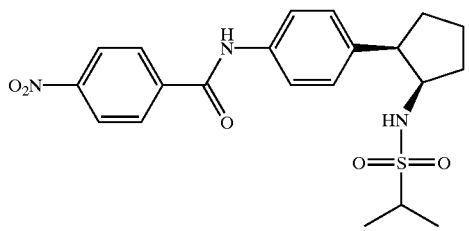

Scheme IV, step C: The amine (200 mg, 0.706 rnmol, prepared in example 23), triethylamine (0.11 mL, 0.776 mmol), 4-nitrobenzoyl chloride (0.1 mL, 0.776 mmol) and methylene chloride (4.7 mL) were reacted in a manner analogous to the procedure described in Example 61. The title compound (111 mg, 36%) was isolated as orange crystals.

Electrospray-MS 433.0 (M*+1); Analysis; Theory: C 58.45; H 5.84; N 9.74; Found: C 58.07; H 5.91; N 9.22.

EXAMPLE 68

Preparation of (+,−) Cis-3-Nitro-N-{4-[2-(propane-2-sulfonylamino)-cyclopentyl]-phenyl}-benzamide

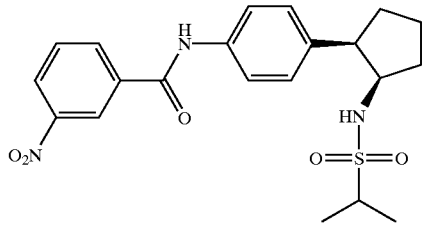

Scheme IV, step C: The amine (200 mg, 0.706 mmol, prepared in example 23), triethylamine (0.11 mL, 0.776 mmol), 3-nitrobenzoyl chloride (0.1 mL, 0.776 mmol) and methylene chloride (4.7 mL) were reacted in a manner analogous to the procedure described in Example 61. The title compound (27 mg, 9%) was isolated as orange crystals.

Electrospray-MS 433.0 (M*+1); Analysis; Theory: C 58.45; H 5.84; N 9.74; Found: C 56.63; H 5.51; N 9.50.

EXAMPLE 69

Preparation of (+,−) Cis-4'-[2-(Propane-2-sulfonylamino)-cyclopentyl]-biphenyl-3-carboxylic Acid Methyl Ester

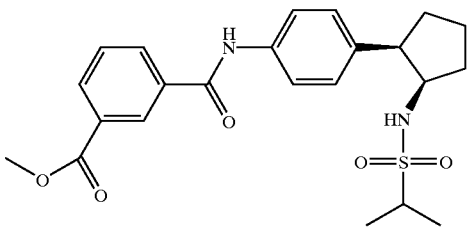

Scheme IV, step C: Monomethyl isophthalate (140 mg, 0.78 mmol) and methylene chloride (4.7 mL) were combined in a 15 mL round bottomed flask, fitted with a y-tube, capped by a rubber stopper, and nitrogen gas, and stirbar. Next, by syringe, oxalyl chloride (0.2 mL, 3.106 mmol) was added, and stirred at room temperature for one hour. After one hour the reaction mixture was reduced under vacuum and to it was added the amine from example 23 (200 mg, 0.706 mmol), triethylamine (0.11 mL, 0.776 mmol), and anhydrous tetrahydrofuran (4.7 mL). The reaction mixture was then stirred under same conditions for an additional hour. Next the reaction mixture was quenched with water, and extracted with methylene chloride (25 mL×3). The organic layer was dried (MgSO$_4$), filtered, and concentrated under reduced vacuum, yielding 385 mg of a brown foam. This material was purified via silica gel chromatography, utilizing a Chromatotron® with a 4000 uM rotor in a 3:1 hexane:ethyl acetate solvent system, yielding the title compound (277 mg, 80%) as white crystals.

Electrospray-MS 446.0 (M*+1); Analysis; Theory: C 62.14; H 6.35; N 6.30; Found: C 61.80; H 6.22; N 6.32.

EXAMPLE 70

Preparation of (+,−) Cis N-{4'-[2-(Propane-2-sulfonylamino)-cyclopentyl]-biphenyl-4-yl}-acetamide

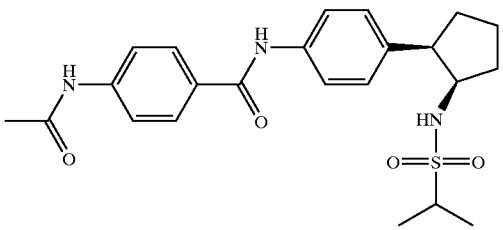

The amine prepared in example 23 (300 mg, 1.0585 mmol,), triethylamine (0.4 mL 2.646 mmol), dimethylaminopyridine (5 mg, 0.04 mmol), 4-acetamidobenzoic acid (190 mg, 1.0585 mmol), 1-(3-dimethylaminopropyl)-3-ethylcarbodiimide hydrochloride (255 mg, 1.323 mmol), and anhydrous tetrahydrofuran (7 mL), were combined in a 15 mL round bottomed flask, fitted with a stirbar, and under a nitrogen atmosphere. The mixture was stirred vigorously at room temperature for 88 hours, then was quenched with water (15 mL), and extracted with methylene chloride (25 mL×3). Organic layer was next dried (MgSO$_4$), filtered, and concentrated under vacuum, yielding 400 mg of brown foam. The material was purified with silica gel chromatography, utilizing a Chromatotron® with a 6000 uM rotor, in a 1:1 hexanes:ethyl acetate solvent system, yielding the title compound (340 mg, 72%) as yellow solid.

Electrospray-MS 446.0 (M*+1); Analysis; Theory: C 62.28; H 6.59; N 9.47; Found: C 61.08; H 6.81; N 8.57.

EXAMPLE 71

Preparation of (+,−) Cis N-{4'-[2-(Propane-2-sulfonylamino)-cyclopentyl]-biphenyl-3-yl}-acetamide

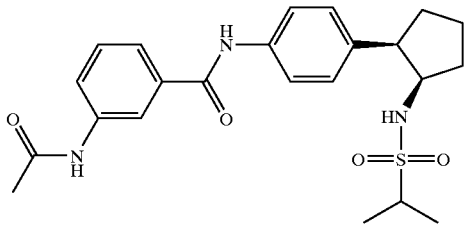

Scheme IV, step C: The amine prepared in example 23 (300 mg, 1.0585 mmol), triethylamine (0.4 mL 2.646 mmol), dimethylaminopyridine (5 mg, 0.04 mmol), 4-acetamidobenzoic acid (190 mg, 1.0585 mmol), 1-(3-dimethylaminopropyl)-3-ethylcarbodiimide hydrochloride (255 mg, 1.323 mmol), and anhydrous tetrahydrofuran (7 mL), were reacted in a manner analogous to the procedure described in Example 70. The title compound (110 mg, 23%) was isolated as a yellow solid.

Electrospray-MS 433.0 (M*+1).

EXAMPLE 72

Preparation of (+,−) Cis- N-{4'-[2-(Propane-2-sulfonylamino)-cyclopentyl]-biphenyl-3-yl}-acetamide

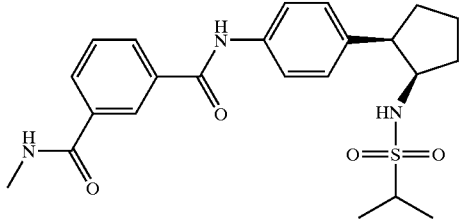

The ester prepared in example 69 (600 mg, 1.35 mmol,), lithium hydroxide (200 mg, 4.725 mmol), methanol (6.75 mL), water (6.75 mL), and tetrahydrofuran (20.25 mL), were combined in a 100 mL round bottomed flask, fitted with a stirbar, and under a nitrogen atmosphere. The mixture was stirred vigorously at room temperature for 16 hours, then was concentrated under vacuum, dissolved in 1N HCl, and extracted with methylene chloride (50 mL×3). Organic layer was next dried (MgSO$_4$), filtered, and concentrated under vacuum, yielding 305 mg of white solid. Transferred this material to a 25 mL round bottomed flask and combined with triethylamine (0.36 mL 2.585 mmol), dimethylaminopyridine (5 mg, 0.04 mmol), methyl amine (0.036 mL, 1.03 mmol), 1-(3-dimethylaminopropyl)-3-ethylcarbodiimide hydrochloride (248 mg, 1.29 mmol), and anhydrous tetrahydrofuran (6.9 mL). The flask was fitted with a stirbar, and under a nitrogen atmosphere and was stirred vigorously at room temperature for 88 hours, then was quenched with water (15 mL), and extracted with methylene chloride (25 mL×3). Organic layer was next dried (MgSO$_4$), filtered, and concentrated under vacuum, yielding 210 mg of yellow foam. The material was purified with silica gel chromatography, utilizing a Chromatotron® with a 2000 uM rotor, in a 9:1 ethyl acetate:methanol solvent system, yielding the title compound (42 mg, 9%) as a yellow solid.

Electrospray-MS 446.0 (M*+1).

EXAMPLE 73

Preparation of (+,−) Cis- N-{4'-[2-(Propane-2-sulfonylamino)-cyclopentyl]-biphenyl-4-yl}-acetamide

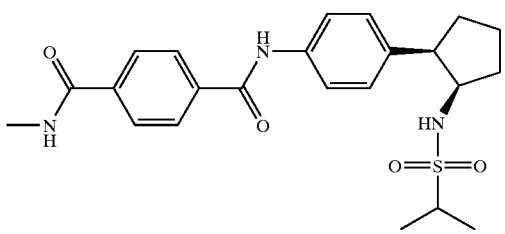

The ester prepared in example 66 (363 mg, 0.817 mmol), lithium hydroxide (120 mg, 2.86 mmol), methanol (4 mL), water (4 mL), and tetrahydrofuran (12 mL), were combined in a 100 mL round bottomed flask, fitted with a stirbar, and under a nitrogen atmosphere. The mixture was stirred vigorously at room temperature for 16 hours, then was concentrated under vacuum, dissolved in 1N HCl, and extracted with methylene chloride (50 mL×3). Organic layer was next dried (MgSO$_4$), filtered, and concentrated under vacuum, yielding 305 mg of a white solid. Transferred this material to a 25 mL round bottomed flask and combined with triethylamine (0.25 mL 1.77 mmol), dimethylaminopyridine (3 mg, 0.03 mmol), methylamine (0.025 mL, 0.71 mmol), 1-(3-dimethylaminopropyl)-3-ethylcarbodiimide hydrochloride (171 mg, 0.89 mmol), and anhydrous tetrahydrofuran (4.75 mL). The flask was fitted with a stirbar, and under a nitrogen atmosphere and was stirred vigorously at room temperature for 88 hours, then was quenched with water (15 mL), and extracted with methylene chloride (25 mL×3). Organic layer was next dried (MgSO$_4$), filtered, and concentrated under vacuum, yielding 75 mg of a yellow foam. The material was purified with silica gel chromatography, utilizing a Chromatotron® with a 1000 uM rotor, in a 9:1 ethyl acetate:methanol solvent system, yielding the title compound (40 mg, 9%) as a yellow solid.

Electrospray-MS 446.0 (M*+1).

EXAMPLE 74

Preparation of (+,−)-Cis-(4-{4-[2-(Propane-2-sulfonylamino)-cyclopentyl]-phenylcarbamoyl}-phenyl)-carbamic Acid tert-butyl Ester

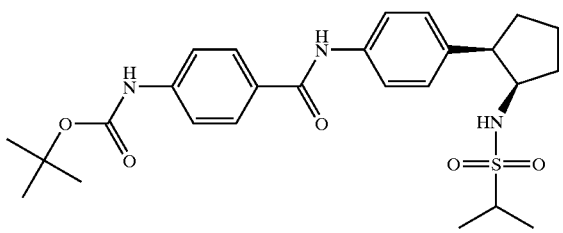

The acid prepared in preparation 26 (315 mg, 1.33 mmol), triethylamine (0.45 mL 3.33 mmol), dimethylaminopyridine (6.5 mg, 0.05 mmol), 1-(3-dimethylaminopropyl)-3-ethylcarbodiimide hydrochloride (320 mg, 1.66 mmol), the amine prepared in example 23 (377 mg, 1.33 mmol), and anhydrous tetrahydrofuran (9 mL) were combined in a 25 mL round bottomed flask fitted with a stirbar, and under a nitrogen atmosphere and was stirred vigorously at room temperature for 88 hours, then was quenched with water (15 mL), and extracted with methylene chloride (25 mL×3). Organic layer was next dried (MgSO$_4$), filtered, and concentrated under vacuum, yielding 400 mg of brown foam. The material was purified with silica gel chromatography, utilizing a Chromatotron® with a 6000 uM rotor, in a 1:1 hexanes:ethyl acetate solvent system, yielding the title compound (285 mg, 43%) as white solid. Electrospray-MS 446.0 (M*+1).

EXAMPLE 75

Preparation of (+,−)-Cis-(4-{4-[2-(Propane-2-sulfonylamino)-cyclopentyl]-phenylcarbamoyl}-phenyl)-carbamic Acid tert-butyl Ester

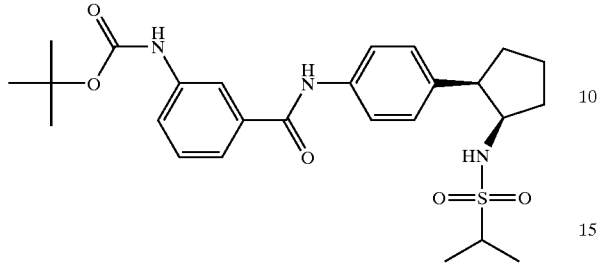

The acid prepared in preparation 27 (335 mg, 1.41 mmol), triethylamine (0.5 mL 3.52 mmol), dimethylaminopyridine (7 mg, 0.06 mmol), 1-(3-dimethylaminopropyl)-3-ethylcarbodiimide hydrochloride (340 mg, 1.76 mmol), the amine prepared in example 23 (400 mg, 1.41 mmol), and anhydrous tetrahydrofuran (9 mL) were combined in a 25 mL round bottomed flask fitted with a stirbar, and under a nitrogen atmosphere and was stirred vigorously at room temperature for 88 hours, then was quenched with water (15 mL), and extracted with methylene chloride (25 mL×3). Organic layer was dried (MgSO$_4$), filtered, and concentrated under vacuum, yielding 1.2 g of brown liquid. The material was purified with silica gel chromatography, utilizing a Chromatotron® with a 6000 uM rotor, in a 1:1 hexanes:ethyl acetate solvent system, yielding the title compound (180 mg, 25%) as a yellow foam.

Electrospray-MS 503.0 (M*+1).

EXAMPLE 76

Preparation of (+,−)-Cis 4-Amino-N-{4-[2-(propane-2-sulfonylamino)-cyclopentyl]-phenyl}-benzamide

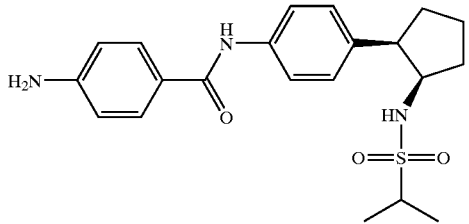

The compound prepared in example 74 (150 mg, 0.299 mmol), trifluoroacetic acid (0.3 mL), and anhydrous methylene chloride (2 mL), were combined in a 10 mL round bottomed flask, fitted with a stirbar, under a nitrogen atmosphere, was stirred at room temperature for two hours, then vacuumed under reduced pressure. This material was dissolved in 5N sodium hydroxide, and extracted (3×15 mL) with methylene chloride, dried (MgSO$_4$), filtered and concentrated under vacuum, to yield 25 mg of yellow oil. This material was purified by silica gel chromatography using a Chromatotron® with a 1000 uM rotor, and a 1:1 hexanes:ethyl acetate solvent system, yielding the title compound as 14 mg (12%) white solid.

Electrospray-MS 503.0 (M*+1); Analysis; Theory: C 62.82; H 6.78; N 10.47; Found: C 58.87; H 6.36; N 9.34.

EXAMPLE 77

Preparation of (+,−)-Cis-3-Amino-N-{4-[2-(propane-2-sulfonylamino)-cyclopentyl]-phenyl}-benzamide

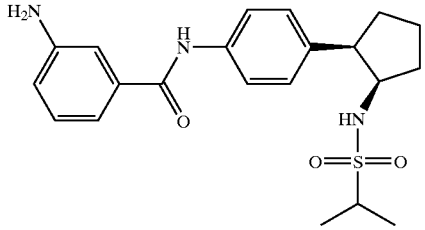

The compound prepared in example 75 (180 mg, 0.36 mmol), trifluoroacetic acid (0.35 mL), and anhydrous methylene chloride (2.5 mL), were combined in a 10 mL round bottomed flask, fitted with a stirbar, under a nitrogen atmosphere, was stirred at room temperature for two hours, then vacuumed under reduced pressure. This material was dissolved in 5N sodium hydroxide, and extracted (3×15 mL) with methylene chloride, dried (MgSO$_4$), filtered and concentrated under vacuum, to yield 600 mg of orange liquid. This material was purified by silica gel chromatography using a Chromatotron® with a 1000 uM rotor, and a 1:1 hexanes:ethyl acetate solvent system, yielding the title compound as 35 mg (24%) white solid.

Electrospray-MS 503.0 (M*+1); Analysis; Theory: C 62.82; H 6.78; N 10.47; Found: C 59.12; H 6.29; N 9.29.

EXAMPLE 78

Preparation of (+,−) Cis-N-[2-(phenyl)-cyclopentyl]-dimethylaminosulfonamide

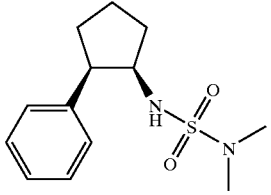

Scheme II, step A: The amine from Preparation 8 (180 mg, 0.36 mmol), 1,8-diazabicyclo[5.4.0]undec-7-ene (1.86 mL, 12.4 mmol), and anhydrous methylene chloride (85 mL), were combined in a 250 mL round bottomed flask, fitted with a stirbar, under a nitrogen atmosphere, was cooled to 0° C., then added N-dimethylsulfonyl chloride (1.33 mL, 12.4 mmol), by syringe, dropwise. The reaction was then mixed and allowed to come to room temperature overnight. The reaction was quenched with water (100 mL), and extracted (3×75 mL) with methylene chloride, dried (MgSO$_4$), filtered and concentrated under vacuum, to yield 4.96 g of yellow oil. This material was purified by silica gel chromatography using a Waters HPLC Prep 2000, with one Prep-Pak, and a 3:1 hexanes:ethyl acetate solvent system, yielding the title compound as 2.1 g (63%) white crystals.

Electrospray-MS 269.0 (M*+1); Analysis; Theory: C 58.18; H 7.51; N 10.44; Found: C 58.33; H 7.48; N 10.34.

EXAMPLE 79

Preparation of (+,−) Cis-N-[2-(4-Bromo-phenyl)-cyclopentyl]-dimethylaminosulfonamide

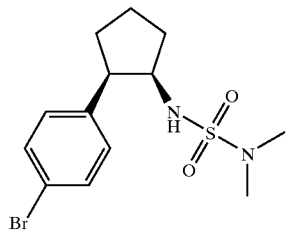

Scheme II, step A: Into a 250 mL 3n flask fitted with a stirrer and thermometer, 876 mg (6.1 mmol) of dimethylaminosulfamyl chloride was added dropwise to 1.40 gm (5.8 mmol) of the compound from preparation 10 and 927 mg (6.1 mmol) DBU in tetrahydrofuran (75 mL) while stirring at 0° C. under a nitrogen atmosphere. The reaction was then allowed to warm to room temperature and stirred overnight. In the morning, the mixture was concentrated under reduced vacuum. The resulting semi-solid was taken into methylene chloride (200 mL), washed once with water, dried over sodium sulfate, and concentrated under reduced vacuum to yield two spot material as an oil. This material was separated and purified via silica gel chromatography employing the Chromatotron® using a 4000 micron rotor and eluting with an gradient solvent of hexane/ethyl acetate 19:1 to hexane/ethyl acetate 15:1 to yield 513 mg (26%) of the top spot as a white solid. Ion spray M.S. 346 (M*−1):

Calculated for: $C_{13}H_{19}N_2O_2SBr$ Theory: C 44.96, H 5.51, N 8.06 Found: C 44.60, H 5.71, N 8.30.

EXAMPLE 80

Preparation of (+,−) Cis-N-[2-(3'-Methanesulfonylamino-biphenyl-4-yl)-cyclopentyl]-dimethylaminosulfonamide

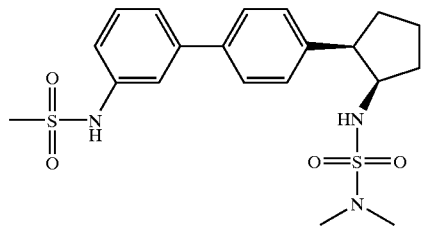

Scheme II, step C: Into a 100 mL single neck flask the compound from the above example 79 (233 mg, 0.67 mmol) and N-[3-(4,4,5,5-tetramethyl-[1,3,2]dioxaborolan-2-yl)-phenyl]-methanesulfonamide.(208 mg, 0.70 mmol), palladium(0)tetrakistriphenylphosphine (35 mg, 0.03 mmol), and potassium carbonate (97 mg, 0.70 mmol) were mixed together in 1,4-dioxane/water 3:1 (50 mL) and stirred overnight at 80° C. In the morning, the reaction was let cool to room temperature and poured into water. The desired material was extracted into ethyl acetate. The organic layer was washed once with water, dried over sodium sulfate, and concentrated under reduced vacuum to yield a dark oil. This material was purified via silica gel chromatography employing the Chromatotron® with a 2000 micron rotor and eluting with a gradient solvent of hexane/ethyl acetate 7:3 to hexane/ethyl acetate 1:1 to yield 104 mg (35%) as a semi-solid. Ion spray M.S. 436 (M*−1):

Calculated for: $C_{20}H_{27}N_3O_4S_2$: Theory: C 54.89, H 6.22, N 9.60; Found: C 55.00, H 6.42, N 9.12.

EXAMPLE 81

Preparation of (+,−) Cis-N-[2-(4-cyano-biphenyl-4-yl)-cyclopentyl]-dimethylaminosulfonamide

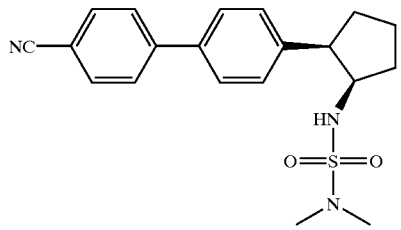

Scheme II, step C: Into a 100 mL single neck flask the compound from example 79 (233 mg, 0.67 mmol) and 4-cyanophenylboronic acid (103 mg, 0.70 mmol), palladium (0)tetrakistriphenylphosphine (33 mg, 0.03 mmol), and potassium carbonate (97 mg, 0.70 mmol) were mixed together in 1,4-dioxane/water 3:1 (50 mL) and stirred overnight at 80° C. In the morning, the reaction was let cool to room temperature and poured into water. The desired material was extracted into ethyl acetate. The organic layer was washed once with water, dried over sodium sulfate, and concentrated under reduced vacuum to yield a dark oil as a 2 spot material. This material was separated and purified via silica gel chromatography employing the Chromatotron® with a 2000 micron rotor and eluting with a gradient solvent of hexane/ethyl acetate 4:1 to hexane/ethyl acetate 1:1 to yield 53 mg (21%) of the bottom spot as a semi-solid. Ion spray M.S. 368 (M*−1): Calculated for $C_{20}H_{23}N_3O_2S \times 0.75 H_2O$: Theory: C 62.74, H 6.27, N 10–98 Found: C 62.82, H 6.04, N 10.05.

The ability of compounds of formula I to potentiate glutamate receptor-mediated response may be determined using fluorescent calcium indicator dyes (Molecular Probes, Eugene, Oregon, Fluo-3) and by measuring glutamate-evoked reflux of calcium into GluR4 transfected HEK293 cells, as described in more detail below.

In one test, 96 well plates containing confluent monolayers of HEK 293 cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes.

Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared by adding 3 μl of 100 mM cyclothiazide to 3 mL of buffer. Control buffer solution is prepared by adding 1.5 μl DMSO to 498.5 μl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 µM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

FORMULATION 1

Hard gelatin capsules are prepared using the following ingredients:

|  | Quantify (mg/capsule) |
|---|---|
| Active Ingredient | 250 |
| Starch, dried | 200 |
| Magnesium Stearate | 10 |
| Total | 460 |

The above ingredients are mixed and filled into hard gelatin capsules in 460 mg quantities.

FORMULATION 2

Tablets each containing 60 mg of active ingredient are made as follows:

|  | Quantity (mg/tablet) |
|---|---|
| Active Ingredient | 60 |
| Starch | 45 |
| Microcrystalline Cellulose | 35 |
| Polyvinylpyrrolidone | 4 |
| Sodium Carboxymethyl Starch | 4.5 |
| Magnesium Stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of formula I which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds can be administered by a variety of routes including oral, rectal, transdermal, subcutaneous, intravenous, intramuscular, bucal or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

As with any group of structurally related compounds which possess a particular generic utility, certain groups and configurations are preferred for compounds of formula I. With respect to substituent $R^4$, compounds wherein $R^4$ is methyl, ethyl, n-propyl and isopropyl are preferred, with isopropyl being especially preferred.

With respect to substituent $R^1$, compounds wherein $R^1$ is hydrogen, fluoro,. chloro, bromo, iodo, amino, nitro, —$NHSO_2CH_3$, and (1–6C)alkyl are preferred.

With respect to substituent $R^2$, compounds wherein $R^2$ is hydrogen, fluoro, chloro, bromo, iodo, amino, nitro, —$NHSO_2CH_3$, and (1–6C)alkyl are preferred.

With respect to substituent $R^3$, compounds wherein $R^3$ is hydrogen, fluoro, chloro, bromo, iodo, amino, nitro, —$NHSO_2CH_3$, and (1–6C)alkyl are preferred.

More specifically, with respect to $R^1$, $R^2$, and $R^3$, compounds wherein $R^1$ is hydrogen and $R^2$ and $R^3$ are fluoro are preferred, and compounds wherein $R^1$ and $R^2$ are hydrogen and $R^3$ is (1–6C)alkyl, amino, nitro, —$NHSO_2CH_3$, fluoro, chloro, bromo and iodo are especially preferred.

With respect to substituents $R^1$, $R^{1'}$, $R^2$, $R^3$, and $R^{3'}$ compounds wherein $R^1$, $R^{1'}$, $R^3$, and $R^{3'}$ are hydrogen, and $R^2$ is in the para-position and is as listed in table 1, are preferred:

TABLE 1

| | $R^2$ |
|---|---|
| a | phenyl |
| b | 4-cyanophenyl (N≡C—C₆H₄—) |
| c | 4-(2-(methylsulfonylamino)ethyl)phenyl (CH₃SO₂NH–CH₂CH₂–C₆H₄–) |
| d | 3-(methylsulfonylamino)phenyl |
| e | 2,6-difluorophenyl |
| f | 4-(cyanomethyl)phenyl (N≡C–CH₂–C₆H₄–) |
| g | 4-(2-aminoethyl)phenyl (H₂N–CH₂CH₂–C₆H₄–) |
| h | 4-(2-acetamidoethyl)phenyl (CH₃C(O)NH–CH₂CH₂–C₆H₄–) |
| j | 4-(2-(trifluoroacetamido)ethyl)phenyl (CF₃C(O)NH–CH₂CH₂–C₆H₄–) |
| k | benzamido (C₆H₅–C(O)–NH–) |

TABLE 1-continued

R$^2$

| | |
|---|---|
| l | (ethyl ester of but-2-enoic acid group) |
| m | (4-benzamido group, -NH-C(=O)-C6H4-) |
| n | (4-sulfamoylphenyl group, H2N-SO2-C6H4-) |

With respect to substituents R$^{10}$, R$^{10'}$, R$^{11}$, R$^{11'}$, R$^{12}$, and R$^{12'}$ compounds wherein R$^{10}$, R$^{10'}$, R$^{12}$, and R$^{12'}$ are hydrogen and R$^{11}$ are —NHC(=O)R$^5$, —NHSO$_2$R$^5$, —CH$_2$NHSO$_2$R$^5$, —CH$_2$CH$_2$NHSO$_2$R$^5$ are preferred.

With respect to substituent R$^5$, compounds wherein R$^5$ are methyl, ethyl, n-propyl, isopropyl, phenyl are preferred, with methyl being most preferred.

With respect to substituent R$^6$, compounds wherein R$^6$ are methyl, ethyl, propyl, isopropyl, tert-butyl or phenyl are preferred.

With respect to substituent R$^7$, compounds wherein R$^7$ are hydrogen, methyl, ethyl or propyl are preferred.

With respect to substituent R$^8$, compounds wherein R$^8$ are hydrogen, methyl, ethyl or propyl are preferred.

With respect to substituent R$^9$, compounds wherein R$^9$ are hydrogen, methyl, ethyl or propyl are preferred.

With respect to n, compounds wherein n is 0, 1, or 2 are preferred.

What is claimed is:

1. A compound of the formula:

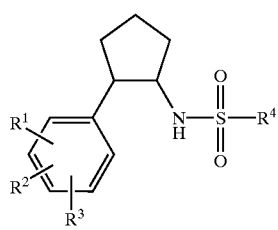

wherein

R$^1$, R$^2$, and R$^3$ each independently represent hydrogen, halogen, CF$_3$, OCF$_3$, CN, NO$_2$, NH$_2$, (1–6C)alkyl, (1–6C)alkoxy, —(CH$_2$)$_n$NHSO$_2$R$^5$, —(CH$_2$)$_n$NHC(=O)R$^5$, —SO$_2$R$^5$, —C(=O)R$^6$, —CH=CHCO$_2$R$^7$, heterocycle, or phenyl which is unsubstituted or substituted by one, two, or three substituents selected from the group consisting of halogen, CF$_3$, OCF$_3$, CN, NO$_2$, NH$_2$, (1–6C)alkyl, (1–6C)alkoxy, —(CH$_2$)$_n$NHSO$_2$R$^5$, —(CH$_2$)$_n$NHC(=O) R$^5$, —SO$_2$R$^5$, —C(=O)R$^6$, —C(=O)NR$^{10}$R$^{11}$, —SO$_2$NR$^{10}$R$^{11}$, or —CH=CHCO$_2$R$^7$;

R$^4$ represents (1–6C)alkyl, (2–6C)alkenyl, or NR$^8$R$^9$;

R$^5$ represents (1–6C)alkyl, CF$_3$, or phenyl which is unsubstituted or substituted by one, two, or three substituents selected from the group consisting of halogen, CF$_3$, CN, NO$_2$, NH$_2$, (1–6C)alkyl, or (1–6C)alkoxy;

R$^6$ represents (1–4C)alkyl or phenyl;

R$^7$ represents hydrogen or (1–4C)alkyl;

R$^8$ and R$^9$ each independently represent hydrogen or (1–4C)alkyl;

R$^{10}$ and R$^{11}$ each independently represent hydrogen or (1–4C)alkyl; and n is 0, 1, 2, 3, or 4;

or a pharmaceutically acceptable salt thereof.

2. A compound according to claim 1 wherein R$^4$ represents (1–6C)alkyl.

3. A compound according to claim 2 wherein R$^4$ represents methyl, ethyl or isopropyl.

4. A compound according to claim 3 wherein R$^4$ represents isopropyl.

5. A compound according to claim 4 wherein R$^1$ and R$^3$ represent hydrogen.

6. A compound according to claim 5 wherein R$^2$ represents phenyl which is unsubstituted or substituted by one, two, or three substituents selected from the group consisting of halogen, CF$_3$, OCF$_3$, CN, NO$_2$, NH$_2$, (1–6C)alkyl, (1–6C)alkoxy, —(CH$_2$)$_n$NHSO$_2$R$^5$, —(CH$_2$)$_n$NHC(=O) R$^5$, —SO$_2$R$^5$, —C(=O)R$^6$, —C(=O)NR$^{10}$R$^{11}$, —SO$_2$NR$^{10}$R$^{11}$, or —CH=CHCO$_2$R$^7$.

7. A compound according to claim 6 wherein phenyl is substituted with one substituent selected from the group consisting of halogen, CF$_3$, OCF$_3$, CN, NO$_2$, NH$_2$, (1–6C)alkyl, (1–6C)alkoxy, —(CH$_2$)$_n$NHSO$_2$R$^5$, —(CH$_2$)$_n$NHC(=O)R$^5$, —SO$_2$R$^5$, —C(=O)R$^6$, —C(=O)NR$^{10}$R$^{11}$, —SO$_2$NR$^{10}$R$^{11}$, or —CH=CHCO$_2$R$^7$.

8. A compound according to claim 7 wherein the phenyl is substituted with —(CH$_2$)$_n$NHSO$_2$R$^5$.

9. A compound according to claim 8 wherein n is 2.

10. A compound according to claim 9 wherein R$^5$ is methyl, ethyl or isopropyl.

11. A compound according to claim 10 wherein the phenyl is para-substituted with —(CH$_2$)$_n$NHSO$_2$R$^5$.

12. A compound according to claim 7 wherein phenyl is substituted with —SO$_2$R$^5$.

13. A compound according to claim 12 wherein R$^5$ is methyl, ethyl or isopropyl.

14. A compound according to claim 13 wherein the phenyl is meta-substituted with —SO$_2$R$^5$.

15. A compound according to claim 5 wherein R$^2$ is —(CH$_2$)$_n$NHC(=O)R$^5$.

16. A compound according to claim 15 wherein n is 0.

17. A compound according to claim 16 wherein R$^5$ represents phenyl which is unsubstituted or substituted by one, two, or three substituents selected from the group consisting of halogen, CF$_3$, CN, NO$_2$, NH$_2$, (1–6C)alkyl, or (1–6C)alkoxy.

18. A compound according to claim 17 wherein the phenyl is substituted by one or two substituents selected from the group consisting of halogen, CF$_3$, CN, NO$_2$, NH$_2$, (1–6C) alkyl, or (1–6C)alkoxy.

19. A compound according.to claim 18 wherein the phenyl is substituted by one or two substituents selected from the group consisting of halogen.

20. A compound according to claim 19 wherein the halogen is fluorine.

21. A compound according to claim 7 wherein phenyl is substituted with —C(=O)NR$^{10}$R$^{11}$.

22. A compound according to claim 21 wherein R$^{10}$ is hydrogen and R$^{11}$ is methyl.

23. A compound according to claim 7 wherein phenyl is substituted with —SO$_2$NR$^{10}$R$^{11}$.

24. A compound according to claim 23 wherein $R^{10}$ and $R^{11}$ are hydrogen.

25. A compound which is selected from the group consisting of:

(+,−) trans-propane-2-sulfonic acid (2-phenyl-cyclopentyl)-amide;

(+,−) trans propane-2-sulfonic acid [2-(4-iodo-phenyl)-cyclopentyl]-amide;

(+,−) trans propane-2-sulfonic acid (2-biphenyl-4-yl-cyclopentyl)-amide;

(+,−) trans propane-2-sulfonic acid [2-(4'-cyano-biphenyl-4-yl)-cyclopentyl]-amide;

(+,−) trans propane-2-sulfonic acid {2-[4'-(2-methanesulfonylamino-ethyl)-biphenyl-4-yl]-cyclopentyl}-amide;

(+,−) trans propane-2-sulfonic acid [2-(3'-methanesulfonylamino-biphenyl-4-yl)-cyclopentyl]-amide;

(+,−) trans propane-2-sulfonic acid [2-(2',4'-difluoro-biphenyl-4-yl)-cyclopentyl]-amide;

(+,−) trans propane-2-sulfonic acid [2-(4'-cyanomethyl-biphenyl-4-yl)-cyclopentyl]-amide;

(+,−) trans propane-2-sulfonic acid {2-[4'-(2-amino-ethyl)-biphenyl-4-yl}-cyclopentyl}-amide;

(+,−) trans N-(2-{4'-[2-(Propane-2-sulfonylamino)-cyclopentyl]-biphenyl-4-yl)-ethyl)-acetamide;

(+,−) trans 2,2,2-Trifluoro-N-(2-{4'-[2-(propane-2-sulfonylamino)-cyclopentyl]-biphenyl-4-yl}-ethyl)-acetamide;

(+) trans propane-2-sulfonic acid (2-phenyl-cyclopentyl)-amide;

(−) trans propane-2-sulfonic acid (2-phenyl-cyclopentyl)-amide;

(+) trans propane-2-sulfonic acid [2-(4'-cyano-biphenyl-4-yl)-cyclopentyl]-amide;

(−) trans propane-2-sulfonic acid [2-(4'-cyano-biphenyl-4-yl)-cyclopentyl]-amide;

(+,−) cis-propane-2-sulfonic acid (2-phenyl-cyclopentyl)-amide;

(+,−) cis propane-2-sulfonic acid [2-(4-iodo-phenyl)-cyclopentyl]-amide;

(+,−) cis propane-2-sulfonic acid [2-(4'-cyano-biphenyl-4-yl)-cyclopentyl]-amide;

(+,−) cis propane-2-sulfonic acid {2-[4'-(2-methanesulfonylamino-ethyl)-biphenyl-4-yl]-cyclopentyl}-amide;

(R,R)-propane-2-sulfonic acid (2-phenyl-cyclopentyl)-amide;

(S,S)-propane-2-sulfonic acid (2-phenyl-cyclopentyl)-amide;

(+,−) cis propane-2-sulfonic acid (2-(4-nitro-phenyl)-cyclopentyl]-amide;

(+,−) cis propane-2-sulfonic acid [2-(4-amino-phenyl)-cyclopentyl]-amide;

(+,−) cis N-{4-[2-(Propane-2-sulfonylamino)-cyclopentyl]-phenyl}-benzamide;

(+,−) cis propane-2-sulfonic acid [2-(4-methanesulfonylamino-phenyl)-cyclopentyl]-amide;

(+,−) cis propane-2-sulfonic acid [2-(4-tert-butyl-phenyl)-cyclopentyl]-amide;

(+,−) trans propane-2-sulfonic acid [2-(4-tert-butyl-phenyl)-cyclopentyl]-amide;

(+,−) cis propane-2-sulfonic acid [2-(3'-methanesulfonylamino-biphenyl-4-yl)-cyclopentyl]-amide;

(+,−) cis-propane-2-sulfonic acid (2-p-tolyl-cyclopentyl)-amide;

(+,−) trans-3-{4-[2-(propane-2-sulfonylamino)-cyclopentyl]-phenyl}-acrylic acid ethyl ester;

(+,−) cis-propane-2-sulfonic acid (2-p-bromophenyl-cyclopentyl)-amide;

(+,−) cis-propane-2-sulfonic acid (2-p-chlorophenyl-cyclopentyl)-amide;

(+,−) cis-propane-2-sulfonic acid (2-(2,4-difluorophenyl)-cyclopentyl)-amide;

(1S,2S) cis propane-2-sulfonic acid [2-(4-iodo-phenyl)-cyclopentyl]-amide;

(1R,2R) cis propane-2-sulfonic acid [2-(4-iodo-phenyl)-cyclopentyl]-amide;

(1S,2S) cis-propane-2-sulfonic acid (2-(2,4-difluorophenyl)-cyclopentyl)-amide;

(1R,2R) cis-propane-2-sulfonic acid (2-(2,4-difluorophenyl)-cyclopentyl)-amide;

(+,−) cis-propane-2-sulfonic acid [2-(3-fluoro-phenyl)-cyclopentyl]-amide;

(+,−) cis-propane-2-sulfonic acid [2-(3,4-difluoro-phenyl)-cyclopentyl]-amide;

(1S,2S) cis-propane-2-sulfonic acid [2-(4-cyano-phenyl)-cyclopentyl]-amide;

(1R,2R) cis-propane-2-sulfonic acid [2-(4-cyano-phenyl)-cyclopentyl]-amide;

(+,−) cis-propane-2-sulfonic acid [2-(2',4'-difluoro-biphenyl-4-yl)-cyclopentyl]-amide;

(+,−) cis propane-2-sulfonic acid [2-(3',5'-difluoro-biphenyl-4-yl)-cyclopentyl]-amide (+,−) cis propane-2-sulfonic acid [2-(4'-methoxy-biphenyl-4-yl)-cyclopentyl]-amide;

(+,−) cis propane-2-sulfonic acid [2-(3'-acetamido-biphenyl-4-yl)-cyclopentyl]-amide;

(+,−) cis propane-2-sulfonic acid [2-(4'-trifluoromethoxy-biphenyl-4-yl)-cyclopentyl]-amide;

(S,S) cis-4'-[2-(propane-2-sulfonylamino)-cyclopentyl]-biphenyl-4-carboxylic acid methylamide;

(R,R) cis-4'-[2-(propane-2-sulfonylamino)-cyclopentyl]-biphenyl-4-carboxylic acid methylamide;

(+,−) cis-propane-2-sulfonic acid {2-[4-(1-oxo-indan-5-yl)-phenyl]-cyclopentyl}-amide;

(+,−) cis-4'-[2-(propane-2-sulfonylamino)-cyclopentyl]-biphenyl-4-sulfonic acid amide;

(S,S) cis-4'-[2-(propane-2-sulfonylamino)-cyclopentyl]-biphenyl-4-sulfonic acid amide;

(R,R) cis-4$^1$-[2-(propane-2-sulfonylamino)-cyclopentyl]-biphenyl-4-sulfonic acid amide;

(+,−)-cis-4$^1$-[2-(propane-2-sulfonylamino)-cyclopentyl]-biphenyl-4-carboxylic acid;

(+,−) cis-4'-[2-(propane-2-sulfonylamino)-cyclopentyl]-biphenyl-4-carboxylic acid methylamide;

(+,−) trans propane-2-sulfonic acid (2-(4-bromo-phenyl)-cyclopentyl)-amide;

(+,−) trans 4'-[2-(propane-2-sulfonylamino)-cyclopentyl]-biphenyl-4-sulfonic acid amide;

(+,−) trans 4'-[2-(propane-2-sulfonylamino)-cyclopentyl]-biphenyl-4-carboxylic acid;

(1R,2S) trans propane-2-sulfonic acid [2-(4-bromo-phenyl)-cyclopentyl]-amide;

(1S,2R) trans propane-2-sulfonic acid (2-(4-bromo-phenyl)-cyclopentyl]-amide;

(1R,2S) trans 4'-[2-(propane-2-sulfonylamino)-cyclopentyl]-biphenyl-4-sulfonic acid amide;

(1S,2R) trans 4'-[2-(propane-2-sulfonylamino)-cyclopentyl]-biphenyl-4-sulfonic acid amide;

(1R,2S) trans 4'-[2-(propane-2-sulfonylamino)-cyclopentyl]-biphenyl-4-carboxylic acid methylamide;

(1S,2R) trans 4'-[2-(propane-2-sulfonylamino)-cyclopentyl]-biphenyl-4-carboxylic acid methylamide;

(+,−) trans 4'-[2-(propane-2-sulfonylamino)-cyclopentyl]-biphenyl-4-carboxylic acid methylamide;

(+,−) cis-propane-2-sulfonic acid [2-(4-fluoro-phenyl)-cyclopentyl]-amide;

(+,−) cis-propane-2-sulfonic acid (2-biphenyl-4-yl-cyclopentyl)-amide;

(+,−) cis-4-chloro-N-{4-[2-(propane-2-sulfonylamino)-cyclopentyl)-phenyl}-benzamide;

(+,−) cis-3,5-difluoro-N-{4-[2-(propane-2-sulfonylamino)-cyclopentyl]-phenyl}-benzamide;

(+,−) cis-2,4-difluoro-N-{4-[2-(propane-2-sulfonylamino)-cyclopentyl]-phenyl}-benzamide;

(+,−) cis-3-cyano-N-{4-[2-(propane-2-sulfonylamino)-cyclopentyl]-phenyl}-benzamide;

(+,−) cis-4-cyano-N-{4-[2-(propane-2-sulfonylamino)-cyclopentyl]-phenyl}-benzamide;

(+,−) cis-N-{4-[2-(propane-2-sulfonylamino)-cyclopentyl]-phenyl}-terephthalamic acid methyl ester;

(+,−) cis-4-nitro-N-{4-(2-(propane-2-sulfonylamino)-cyclopentyl]-phenyl}-benzamide;

(+,−) cis-3-nitro-N-{4-[2-(propane-2-sulfonylamino)-cyclopentyl]-phenyl}-benzamide;

(+,−) cis-4'-[2-(propane-2-sulfonylamino)-cyclopentyl]-biphenyl-3-carboxylic acid methyl ester;

(+,−) cis N-{4'-[2-(propane-2-sulfonylamino)-cyclopentyl]-biphenyl-4-yl}-acetamide;

(+,−) cis N-{4'-[2-(propane-2-sulfonylamino)-cyclopentyl]-biphenyl-3-yl}-acetamide;

(+,−) cis-N-{4'-[2-(propane-2-sulfonylamino)-cyclopentyl]-biphenyl-3-yl}-acetamide;

(+,−) cis- N-{4'-[2-(propane-2-sulfonylamino)-cyclopentyl]-biphenyl-4-yl}-acetamide;

(+,−)-cis-(4-{4-[2-(propane-2-sulfonylamino)-cyclopentyl]-phenylcarbamoyl}-phenyl)-carbamic acid tert-butyl ester;

(+,−)-cis-(4-{4-[2-(propane-2-sulfonylamino)-cyclopentyl]-phenylcarbamoyl}-phenyl)-carbamic acid tert-butyl ester;

(+,−)-cis 4-amino-N-(4-[2-(propane-2-sulfonylamino)-cyclopentyl]-phenyl}-benzamide;

(+,−)-cis-3-amino-N-{4-[2-(propane-2-sulfonylamino)-cyclopentyl]-phenyl}-benzamide;

(+,−) cis-N-[2-(phenyl)-cyclopentyl]-dimethylaminosulfonamide;

(+,−) cis- N-[2-(4-bromo-phenyl)-cyclopentyl]-dimethylaminosulfonamide;

(+,−) cis-N-[2-(3'-methanesulfonylamino-biphenyl-4-yl)-cyclopentyl]-dimethylaminosulfonamide; and (+,−) cis-N-[2-(4-cyano-biphenyl-4-yl)-cyclopentyl]-dimethylaminosulfonamide;

or a pharmaceutically acceptable salt thereof.

26. A pharmaceutical composition, which comprises a compound as claimed in claim 1 and a pharmaceutically acceptable diluent or carrier.

27. A method of treating a cognitive disorder; a neurogenerative disorder; age-related dementia; age-induced memory impairment; movement disorder; reversal of a drug-induced state; depression; attention deficit disorder; attention deficit hyperactivity disorder; psychosis; cognitive deficits associated with psychosis; drug-induced psychosis, or stroke in a patient, which comprises administering to the patient an effective amount of a compound according to claim 1.

28. A method for improving memory or learning ability in a patient, which comprises administering to the patient an effective amount of a compound according to claim 1.

29. A method of treating Alzheimer's disease in a patient, which comprises administering to the patient an effective amount of a compound according to claim 1.

* * * * *